US005861300A

United States Patent [19]
Silverman et al.

[11] Patent Number: 5,861,300
[45] Date of Patent: Jan. 19, 1999

[54] ANTIVIRAL TRANSGENIC PLANTS, VECTORS, CELLS AND METHODS

[75] Inventors: Robert H. Silverman; Dibyendu N. SenGupta, both of Shaker Heights, Ohio

[73] Assignee: The Cleveland Clinic Foundation, Cleveland, Ohio

[21] Appl. No.: 436,771

[22] Filed: May 8, 1995

Related U.S. Application Data

[60] Division of Ser. No. 198,973, Feb. 18, 1994, which is a continuation-in-part of Ser. No. 28,086, Mar. 8, 1993, abandoned.

[51] Int. Cl.$^6$ .............................. A01H 5/00; C12N 9/22; C12N 15/12; C12N 15/82
[52] U.S. Cl. .................. 435/240.4; 435/69.1; 435/172.3; 435/252.3; 435/320.1; 800/205; 536/23.2; 536/23.5
[58] Field of Search ........................... 800/205, DIG. 43; 435/69.1, 172.3, 240.4, 240.49, 320.1, 252.3; 536/23.2, 23.5

[56] References Cited

PUBLICATIONS

Gura: Science, 270:575–577 (Oct. 27, 1995).
Nejidat et al.: Physiologia Plantarum, 80:662–668 (1990).
Gergerich et al.: Phytopathology, 78(3):270–272 (1988).
Cuozzo et al.: Bio/Technology, 6:549–557 (May 1988).
Silverman et al.: J. Cell Biol. Supplement 16B, See Abstract G 520, p. 163 (1992).
Meurs, E. et al.: Cell, 62:379–390 (Jul. 27, 1990).
Meurs, E. et al.: J. Virology, 66(10):5805–5814 (1992).
Lee, S.B. et al.: Virology, 193:1037–1041 (1993).
Lomonossoff, G.P.: Virus Resistance Mediated by a Non-structural Viral Gene Sequence, Chapter 5, pp. 79–91 (1993) IN: Transgenic Plants, ed. Hiatt, A. Marcel Dekker, Inc. NY, NY.
Herrera–Estrella, L. et al.: Agrobacterium as a Vector System for the Introduction of Genes into Plants, Chapter 5 pp. 61–92, IN: Plant Genetic Engineering, ed. Dodds, J.H., Cambridge University Press, NY, NY (1985).
Mukherjee, A.B. et al.: Biochemical Pharmacology, 48(1):1–10 (1994).
Yang, N.S.: Critical Reviews in Biotechnology, 12(4):335–356 (1992).
Deng, T. et al.: Gene, 93:229–234 (1990).
Seilhamer, J.J. et al.: J. Cell Biochem., 39:327–337 (1989).
Bekkers, A.C.A.P.A. et al.: Biochimica et Biophysica Acta, 1089:345–351 (1991).
Luckow et al.: Biotechnology, 6:47–55 (1988).
Seidah et al.: DNA Cell Biol., 11:283–289 (1992).
Jacobsen, H. et al.: Virology, 125:496–501 (1983).
Jacobsen, H. et al.: Proc. Natl. Acad. Sci. USA, 80:4954–4958 (Aug. 1983).
Silverman, R.H. et al.: Local Organ. Comm. of 5th Ann. Meeting of Interf. Res. (The Biol. of Interf. Syst. 1988), 183–186 (1989).
Ferbus, D. et al.: Mol. & Cell. Biochem., 62:51–55 (1984).
Eppstein D.A. et al.: J. Biol. Chem., 257(22):13390–13397 (1982).
Hovanessian, A.G. et al.: J. Biol. Chem., 263(10):4945–4949 (1988).
Hovanessian, A.G. et al.: EMBO J., 6(5):1273–1280 (1987).
Hearl, W.G. et al.: J. Virol., 61(5):1586–1592 (1987).
Wreschner, D.H. et al.: Nature, 289(5796):414–417 (Jan. 29, 1981).
Debois, M.F. et al.: Ann. Inst. Pasteur/Virol., 1987.
Silverman, R.H. et al.: J. Biol. Chem., 263(15) 7336–7341 (May 25, 1988).
Yang–Feng, T.L. et al.: Genomics, 19:173–176 (1994).
Dong, B. et al.: J. Biol. Chem., 269(19):14153–14158 (May 13, 1994).
Hassel, H.A. et al.: EMBO J., 12(8):3297–3304 (1993).
Zhou, A. et al.: Cell, 72:753–765 (Mar. 12, 1993).
William. B.R.G. et al.: Local Org. Comm. of 5th Ann. Meet. of Interf. Res. (The Biol. of Interf. Syst.), 159–162 (1988).
Sawai, H. et al.: J. Biol. Chem., 288(3):171–1677 (Feb. 10, 1983).
Torrence, P.F. et al.: J. Biol. Chem., 263(3):1131–1139 (Jan. 25, 1988).
Lesiak, K. et al.: J. Biol. Chem., 258(21):13082–13088 (Nov. 10, 1983).
Black, R.J. et al.: FEBS Letters, 191(1):154–158 (Oct. 1985).
Sawai, H. et al.: J. Biol. Chem., 258(3):1671–1677 (Feb. 1, 1983).

(List continued on next page.)

*Primary Examiner*—Elizabeth McElwain
*Attorney, Agent, or Firm*—Holland & Knight

[57] ABSTRACT

Isolated 2-5A-dependent RNases, an interferon-induced enzyme which is activated by 5'-phosphorylated, 2',5'-linked oligoadenylates (2-5A) and implicated in both the molecular mechanisms of interferon action and in the fundamental control of RNA stability in mammalian cells, and encoding sequences therefor are disclosed. The expression cloning and analysis of murine and human 2-5A-dependent RNases is also disclosed. Recombinant human 2-5A-dependent RNase produced in vitro bound an activating affinity matrix, 2-5A-cellulose, resulting in ribonuclease activity. The 2-5A binding properties of the recombinant and naturally occurring forms of 2-5A-dependent RNase are basically identical. Interferon induction of 2-5A-dependent RNase expression is demonstrated by measuring the mRNA levels in cells treated with interferon and cycloheximide. Analysis of aligned murine and human 2-5A-dependent RNase sequences revealed several features, including similarity to RNase E which is implicated in the control of mRNA stability in E. coli. A duplicated phosphate-binding loop motif is determined by deletion analysis and site-directed mutagenesis to function in the binding of 2-5A. In addition, recombinant nucleotide sequences, recombinant vectors, recombinant cells and antiviral plants which express, for example, amino acid sequences which have activity that interfere with or inhibit viral replication are disclosed.

10 Claims, 27 Drawing Sheets

OTHER PUBLICATIONS

Torrence, P.F. et al.: *Proc. Natl. Acad. Sci. USA*, 78(1):5993–5997 (Oct. 1981).
Lesiak, K. et al.: *J. Biol. Chem.*, 262(5):1961–1965 (Feb. 15, 1987).
Lesiak, K. et al.: *Bioconjugate Chem.*, 467–472 (Nov./Dec., 1993).
Jacobsen, H.J. et al.: *Virology*, 125:496–501 (1983).
SenGupta, D.N. et al.: *Proc. Natl. Acad. Sic. USA*, 87:7492–7496 (Oct. 1990).
Silverman, R.H.: *Anal. Biochem.*, 144:450–460 (1985).
Krause, D. et al.: *J. Interf. Res.*, 13:13–16 (1993).
Krause, D. et al.: *J. Biol. Chem.*, 260(16):9501–9507 (Aug. 5, 1985).
Kraus, D. et al.: *J. Biol. Chem.*, 261(15):6836–6839 (May 25, 1986).
Maheshwari, R.K. et al.: *Science*, 219:1339–1341 (Mar. 18, 1983).
Nolan–Sorden, N.L.: *Anal. Biochem.*, 184:298–304 (1990).
SenGupta, D.N.: *Proc. Natl. Acad. Sci. USA*, 87:7492–7496 (Oct. 1990).
Silverman, R.H.: *Eur. J. Biochem.*, 126:333–341 (1982).
Ryseicki, G.: *J. Interf. Res.*, 9:649–657 (1989).
Wreschner, D.H. et al.: *Nucelic Acids Res.*, 9(7):1571–1581 (1981).
Cayley, P.J. et al.: *Cell. Resp. to Mol. Modul.*, 347–360.
Torrence, P.F. et al.: *Proc. Natl. Acad. Sci. USA*, 90:1300–1304 (Feb. 1993).
Silverman, R.H. et al.: *Biol. of Interf. System*, 189–200 (1983).
Silverman, R.H. et al.: *J. Virology*, 46(3):1051–1055 (Jun. 1983).
Grimley, P.M. et al.: *Cancer Res.*, 144:3480–3488 (Aug. 1984).
SenGupta, D.N. et al.: *Nucleic Acids Res.*, 17(3):969–978 (1989).
Silverman, R.H.: *J. Interf. Res.*, 14:101–104 (1994).
Kerr, I.M.: *Phil. Trans. R. Soc. Lond.*, B299:59–67 (1982).
Meurs, E. et al.: *Ann. Inst. Pasteur/Virol.*, 137E:251–272 (1986).
Schmidt, A. et al.: *Nat. Immun. Cell Growth Regul.*, 6:19–27 (1987).
Dieffenbach, C.W. et al.: *J. Biol. Chem.*, 264(22):13281–13288 (1989).
Suhadolnik, R.J. et al.: *Biochem.*, 27:8846–8851 (1988).
Wells, J.A. et al.: *J. Biol. Chem.*, 259(2):1363–1370 (Jan. 25, 1984).
Reid, T.R. et al.: *Anal. Biochem.*, 135:000–000 (1983).
Hersh, C.L. et al.: *J. Biol. Chem.*, 259(3):1727–1730 (Feb. 10, 1984).
Iwata, A. et al.: *J. Biochem.*, 104:247–250 (1988).
Shimizu, N. et al.: *J. Biochem.*, 94:1421–1428 (1983).
Orlic, D. et al.: *Exp. Hematol.*, 13:821–826 (1985).
Orlic, D. et al.: *Blood Cells*, 10:193–210 (1984).
Lewis, J.A. et al.: *Viology*, 133:464–469 (1984).
Mengheri, E. et al.: *FEBS*, 157(2):301–305 (Jul. 1983).
Lewis, J.A. et al.: *Eur. J. Biochem.*, 86:497–509 (1978).
Lewis, J.A. et al.: *Proc. Natl. Acad. Sci. USA*, 80:26–30 (Jan. 1983).
Schattner, A. et al.: *J. Interf. Res.*, 1(4):587–594 (1981).
Weissenbach, J. et al.: *Proc. natl. Acad. Sci. USA*, (77)(12):7152–7156 (Dec. 1980).
Revel, M. et al.: *Texas Reports on Biology and Medicine*, 41:452–462 (1981–82).
Revel, M.: "*Molecular Mechanisms Involved in the Intiviral Effects of Interferon*," 101–163.
Revel, M. et al.: *Cell. Resp. Mol. Modul.*, 361–384.
Wallach, D. et al.: *Nature*, 287:68–90 (Sep. 1980).
Revel, M. et al.: *Ann. Rev. Biochem.*, 47:1079–1126 (1978).
Chernajovsky, Y. et al.: *Eur. J. Biochem.*, 96:35–41 (1979).
Wallach, D. et al.: *Interferons*, 449–463 (1982).
Kimchi, A. et al.: *Proc. Natl. Acad. Sci. USA*, 76(7):3208–3212 (Jul. 1979).
Kimchi, A. et al.: *Anti–Mitogenic Func. of Interf.–Induced (2'—5')Oligo(adenylate. . .* 5–10 (1980).
Zilberstein, A. et al.: *Proc. natl. Acad. Sci. USA*, 75(1):4734–4738 (Oct. 1978).
Kimchi, A. et al.: *FEBS*, 134(2):212–216 (Nov. 1981).
Chebath, J. et al.: *J. Biol. Chem.*, 262(8)3852–3857 (Mar. 15, 1987).
Rappoport, S. et al.: *FEBS*, 149(1):47–50 (Nov. 1982).
Panet, A. et al.: *Virology*, 114:567–572 (1981).
Epstein, D.A. et al.: *Eur. J. Biochem.*, 118:9–15 (1981).
Sen, G.C.: *Pharmac. Ther.*, 24:235–257 (1984).
Kumar, R. et al.: *J. Virol.*, 62(2)641–643 (Feb. 1988).
Salzberg, S. et al.: *Mol. Cell. Biol.*, 3(10):1759–1765 (Oct. 1983).
Panet, A.: *Mol. Cell. Ciochem*, 52:153–160 (1983).
Lewis, J.A.: *Virology*, 162:118–127 (1988).
Neth, R. et al.: Reprint from *Modern Trends in Human Leukemia III* (Springer–Verlag Berlin Heidelberg Ny 1979).
Kemchi, A. et al.: *Nature*, 282:20–27 (Dec. 1979).
Sen, G.C. et al.: *J. Biol. Chem.*, 253(17):5915–5921 (Sep. 10, 1978).
Shimizu, N. et al.: *J. Biol. Chem.*, 254(23):12034–12037 (Dec. 10, 1979).
Schmidt, A. et al.: *Proc. natl. Acad. Sci. USA*, 76(10):4788–4792 (Oct. 1979).
Revel, M. et al.: "*Studies on Interef. Action: Synth., Degrad. & Biol. Act. of (2'—5')Oligo–Isoadenylate,*" 1–18.
Lengyel, P. et al.: *J. Interf. Res.*, 7:511–519 (1987).
Floyd–Smith, G. et al.: *J. Interf. Res.*, 8:517–525 (1988).
Kerr, I.M. et al.: *Proc. Natl. Acad. Sci. USA*, 75(1):256–260 (Jan. 1978).
Salehzada, T. et al.: *J. Biol. Chem.*, 266(9):5808–5813 (Mar. 25, 1991).
Hovanessian, A.G. et al.: *Nature*, 268:537–538 (Aug. 1977).
Salehzada, T. et al.: *Anal. Biochem.*, 196:410–414 (1991).
Williams, B.R.G. et al.: *Nature*, 276:88–90 (Nov. 1978).
Roberts, W.K. et al.: *Proc. Natl. Acad. Sci. USA*, 73(9):3136–3140 (Sep. 1976).
Kerr, I.M. et al.: *Nature*, 268:537–542.
Salehzada, T. et al.: *J. Biol. Chem.*, 268(11):7733–7740 (Apr. 15, 1993).
Lengyel, P.: *Proc. Natl. Acad. Sci. USA*, 90:5893–5895 (Jul. 1993).
Cayley, P.J. et al.: *Piochem. Biophys. Res. Comm.*, 108(3):1243–1250 (Oct. 15, 1982).
Kerr, I.M. et al.: *Eur. J. Biochem.*, 69:551–561 (1976).
Kumar, R. et al.: *J. Virol.*, 62(9):3175–3181 (Sep. 1988).
Shaila, S. et al.: *gen. Virol.*, 37:535–546 (1977).
Brown, G.E. et al.: *Biochem. Biophys. Res. Commun.*, 69(1):114–122 (1976).
Sen, G.C. et al. *Nature*, 264:370–373 (Nov. 25, 1976).
Hanks, S.K. et al.: *Science*, 241:42–52 (Jul. 1988).
Singh, H. et al.: *Cell*, 52:415–423 (Feb. 12, 1988).
Singh, H. et al.: *BioTech.*, 7(3):252–261 (1989).
Baglioni, C. et al.: *Nature*, 273:684–687 (Jun. 1978).

Apirion, D.: "Isolation, Genetic Mappern and Some Characerization of a Mutation in Escherichia coli . . .," 659–671 (Dec. 1978).
Goldblum, K. et al.: *J. Bacteriology*, 146:128–132 (Apr. 1981).
Slattery, E. et al.: *Proc. natl. Acad. Sci. USA*, 76(10):4778–4782 (Oct. 1979).
Nilsen, T.W. et al.: *J. Biol. Chem.*, 256(21):10751–10754 )Nov. 10, 1981).
Williams, B.R.G. et al.: *FEBS*, 105(1):47–52 (Sep. 1979).
Floyd–Smith, G.: *J. Cell. Biochem.*, 38:13–21 (1988).
Schmidt, A. et al.: *FEBS*, 95(2):257–264 (Nov. 1978).
Hovanessian, A.G. et al.: *Eur. J. Biochem.*, 84:149–159 (1978).
Clemens, M.J. et al. *Cell*, 13:565–572 (Mar. 1978).
Sen, G.C. et al.: *J. Biol. Chem.*, 267(8):5017–5020 (Mar. 15, 1992).
Nilsen, T.W. et al.: *Proc. Natl. Acad. Sci. USA*, 76(6):2600–2604 (Jun. 1979).
Ratner, L. et al.: *Eur. J. Biochem*, 79:565–577 (1977).
Baglioni, C. et al.: *J. Biol. Chem.*, 255(18):8390–8393 (Sep. 25, 1980).
Williams, B.R.G. et al.: *Nature*, 282(5739):582–586 (Dec. 6, 1979).
Williams, B.R.G. et al.: *"The 2–5A (pppA2'p5'A) System in Interferon–treated and Control Cells"*.
Floyd–Smith, G. et al.: *Science*, 212:1030–1032 (May 1981).
Ratner, L. et al.: *Biochem. Biophys. Res. Commun.*, 81(3):947–954 (Apr. 14, 1978).
Coccia, E.M. et al.: *Virology*, 179:228–233 (1990).
Berg, J.M.: *J. Biol. Chem.*, 265(12):6513–6516 (Apr. 25, 1990).
Evans, R.M. et al.: *Cell*, 52:1–3 (Jan. 15, 1988).
Belasco, J. et al.: *Gene*, 72:15–23 (1988).
Fry, D.C. et al.: *Proc. Natl. Acad. Sci. USA*, 83:907–911 (Feb. 1986).
Walker, J.E. et al.: *EMBO*, 1(8):945–951 (1982).
Krupinski, J. et al.: *Science*, 244:1558–1564 (1989).
Au, D.C. et al.: *Biochem.*, 28:2772–2776 (1989).
Glaser, P. et al.: *EMBO*, 8(3):967–972 (1989).
Imai, J. et al.: *J. Biol. Chem.*, 260(3):1390–1393 (Feb. 10, 1985).
Watling, D. et al.: *EMBO*, 4(2):431–436 (1985).
Pestka S. et al.: *Ann. Rev. Biochem.*, 56:727–777 (1987).
Lengyel, P.: *Ann. Rev. Biochem.*, 51:251–282 (1982).
Night, M. et al.: *Nature*, 288(5787):189–192 (Nov. 13, 1980).
Deutscher, M.P.: *J. Biol. Chem.*, 268(18):13011–13014 (Jun. 25, 1993).
Cedergren, R. et al.: *FEBS*, 226(1)63–66 (Dec. 1987).
Floyd–Smith, G. et al.: *Meth. Enzymology*, 119:489–499 (1986).
Farrell, P.J.: *Proc. Natl. Acad. Sci. USA*, 75(12):5893–5897 (Dec. 1978).
Bisbal, C. et al.: *Eur. J. Biochem.*, 179:595–602 (1989).
Brawerman, G.: *Cell*, 57:9–10 (Apr. 7, 1989).
Mackie, G.A.: *J. Bacteriology*, 178(8)2488–2497 (Apr. 1991).
Xia, Z. et al.: *J. Biol. Chem.*, 265(12):6517–6520 (Apr. 25, 1990).
Saraste, M. et al.: *TIBS*, 15 (Nov. 1990).
Deutscher, M.P. et al.: *Cell*, 40:731–732 (Apr. 1985).
Cormack, R.S. et al.: *Proc. natl. Acad. Sci. USA*, 90:9006–9010 (Oct. 1993).
Bouvet, P. et al.: *Nature*, 360:488–491 (Dec. 3, 1992).
Claverie–Martin, F. et al.: *J. Biol. Chem.*, 266(5):2843–2851 (Feb. 15, 1991).
Mudd, E.A. et al.: *EMBO*, 7(11):3601–3607 (1988).
Ehretsmann, C.P. et al.: *Genes & Develop.*, 6:149–159 (1992).
Tarasevicience, L. et al.: *Mol. Microbiol.*, 5(4):851–855 (1991).
Chauhan, A.K.: *Nucleic Acids Res.*, 19(1)125–129 (1991).
Babitzke, P. et al.: *Proc. Natl. Acad. Sci. USA*, 88:1–5 (Jan. 1991).
Mudd, E.A. et al.: *Mol. Microbiol.*, 4(12):2127–2135 (1990).
Silverman, R.H. et al.: *Eur. J. Biochem.*, 124:131–138 (1982).
Hovanessian, A.G. et al.: *Meth. Enzymol.*, 79:184–199 (1981).
Goswami, B.B. et al.: *J. Biol. Chem.*, 259(3):1371–1374 (Feb. 10, 1984).
Sharma, O.K. et al.: *Proc. Natl. Acad. Sci. USA*, 78(4):2221–2224 (Apr. 1981).
Goswami, B.B. et al.: *J. Biol. Chem.*, 257(12):6867–6870 (Jun. 25, 1982).
Sharma, O.K. et al.: *FEBS* 0601, 158(2):298–300 (Jul. 1983).
Sen, G.C. et al.: *J. Virology*, 45(3):1017–1027 (Mar. 1983).
Sen, G.C. et al.: *J. gen Virol.*, 64:2213–2220 (1983).
Sawai, H. et al.: *J. Biochem.*, 101:339–346 (1987).
Taira, H. et al.: *J. Interf. Res.*, 5:583–596 (1985).
David, S. et al.: *J. Virology*, 63(3):1116–1122 (Mar. 1989).
Affabris, E. et al.: *Virology*, 125:508–512 (1983).
Mechti, N. et al.: *J. Biol. Chem.*, 259(5)3261–3265 (Mar. 10, 1984).
Miyamoto, N.G. et al.: *Virology*, 107:461–475 (1980).
Miyamoto, N.G. et al.: *J. Biol. Chem.*, 258(24):15232–15237 (Dec. 25, 1983).
Eppstein, D.A. et al.: *Virology*, 98:9–19 (1979).
Benech, P. et al.: *Mol. Cell. Biol.*, 7(12):4498–4504 (Dec. 1987).
Cohen, B. et al.: *EMBO*, 7(5):1411–1419 (1988).
Mory, Y. et al.: *J. Interf. Res.*, 9:295–304 (1989).
Imai, J. et al.: *J. Biol. Chem.*, 257(21):12739–12745 (Nov. 10, 1982).
Krause, D. et al.: *Eur. J. Biochem.*, 146:611–618 (1985).
Silverman, R.H. et al.: *Eur. J. Biochem.*, 115:79–85 (1981).
Wreschner, D.H. et al.: *Eur. J. Biochem.*, 124:261–268 (1982).
Wreschner, D.H. et al.: *Eur. J. Biochem.*, 172:333–340 (1988).
Penn, L.J.Z. et al.: *J. Virology*, 49(3):748–753 (Mar. 1984).
Saunders, M.E. et al.: *EMBO*, 4(7):1761–1768 (1985).
Lesiak, K. et al.: *Biochem. Biophys. Res. Commun.*, 126(2):917–921 (Jan. 31, 1985).
Kitade, Y. et al.: *Nucl. Acids Res.*, 19(15):4103–4108 (1991).
Torrence, P.F. et al.: *FEB* 04463, 212(2):267–270 (Feb. 1987).
Alster, D. et al.: *Biochem. Biophys. Res. Commun.*, 141(2):555–561 (Dec. 15, 1986).
Lesiak, K. et al.: *J. Med. Chem.*, 1015–1022 (Jun. 1986).
Ilson, D.H. et al.: *J. Interf. Res.*, 6:05–12 (1986).
Torrence, P.F. et al.: *FEB* 04463, 212(2):267–270 (Feb. 1987).
Jamoulle, J.C. et al.: *Biochem.*, 23:3063–3069 (1984).
Imai, J. et al.: *Biochem.*, 23:766–774 (1984).

Eppstein, D.A. et al.: *J. Biol. Chem.,* 260(6):3666–3671 (Mar. 25, 1985).
Johnston, M.I. et al.: *Biochem. Biophys. Res. Commun.,* 97(2):375–383 (Nov. 28, 1980).
Torrence, P.F. et al.: *J. Med. Chem.,* 27:726–733 (1984).
Imai, J. et al.: *Org. Chem.,* 1418–1420 (May 3, 1985).
Silverman, R.H. et al.: *The Biology of the Interferon System* 1984, Kirchner et al., eds. 1985 Elsevier Science Publishers B.V., pp. 141–145.
Silverman, R. et al: In, *Inteferons as cell growth inhibitors & antitumor factors.* (Friedman et al, eds.) A.R. Liss, NY, NY pp. 143–150(1986).
Williams BRG, (1983). *The Biochemical action of interferon and Cancer,* K Sikora ed, Elsevier, Amsterdam, pp. 33–52.
Doetsch, P.W. et al.: *Proc. Natl. Acad. Sci. USA,* 78:1–9 (1981).
Henderson, E.E. et al.: *Virology,* 122:198–201 (1982).
Wu, J.M. et al.: *Biochem. & Biophys. Res. Comm.,* 86(3):648–653 (1979).
Lee, C. et al.: *FEBS.* 157(1):205–209 (Jun. 1983).
Doetsch, P. et al.: *Nature,* 291:355–358 (May 1981).
Suhadolnik, R.J. et al.: *Biochemistry,* 22:4153–4158 (1983).
Kariko, K. et al.: *Biochemistry,* 26:7127–7135 (1987).
Kariko, K. et al.: *Biochemistry,* 26:7136–7142 (1987).
Suhadolnik, R.J. et al.: *Biochemistry,* 26:7143–7149 (1987).
Suhadolnik, R.J. et al.: *Biochemistry,* 27:8840–8846 (1988).
Suhadolnik, R.J. et al.: *Biochem. & Biophys. Res. Comm.,* 111(1):205–212 (1983).
Black, P.L. et al.: *J. Immun.,* 135(5):2773–2777 (Nov. 1984).
Lee, C. et al.: *Biochemistry,* 24(3):551–555 (Jan. 1985).
Knight, M. et al.: *Meth. Enzymology,* 79:217–227 (1981).
Williams, B.R.G. et al.: *Meth. Enzymology,* 79:199–208 (1981).
Kerr, I.M. et al.: *Adv. Cyclic Nucleo. Res.,* 14:469–478.
Gribaudo, G. et al.: *J. Virol.,* 65(4):1478–1757 (Apr. 1991).
Suhadolnik, R.J. et al.: *Biochemistry,* 22(?):4153–4157 (1983).
Justesen, J. et al.: *Proc. Natl. Acad. Sci. USA,* 77:4618–4622 (1980).
Ono, M. et al.: *J. Mol. Biol.,* 129:343–357 (1979).
LeBleu, B. et al.: *Mechanisms of Interferon Action: Biochem. & Genetic Appr.,* 47–94.
Pai, E.F. et al.: *Nature,* 341:209–214 (Sep. 1989).
St. Laurent, G. et al.: *Cell,* 95–102 (1983).
Saraste, M. et al.: *TIBS,* 15:430–434 (Nov. 1990).
Rozen, F. et al.: *Mol. & Cell. Biol.* 9(9):4061–4063 (Sep. 1989).
Schroder, H.C. et al.: *FASEB J.,* 4:3124–3130 (Oct. 1990).
Suhadolnik, R.J. et al.: *Nucleotides, and their Biol. Appl.,* pp. 147–179 (Academic Press 1983).
Torrence, P.F. et al.: *J. Medicinal Chem.,* 27(6):726–733 (1984).
Torrence, P.F. et al.: *Proc. Natl. Acad. Sci. USA,* 78(10):5993–5997 (Oct. 1981).
Torrence, P.F. et al.: *FEBS,* 130(2):291–296 (Aug. 1981).
Imai, J. et al.: *J. Biol. Chem.,* 257(21):12739–12745 (Nov. 1982).
Morag, A. et al.: *Lancet,* p. 744 (Mar. 27, 1982).
Shulman, L. et al.: *Nature,* 288:98–100 (Nov. 1980).
Lesiak, K. et al.: *FEBS,* 151(2):291–296 (Jan. 1983).
de Clercq, E. et al.: *EUPHAR 9th Int'l Congress of Pharma.,* London 1984, Paton et al. eds. (vol. 1), pp. 307–317.
Williams, B.R.G. et al.: *Biol. of Interf. Syst.,* 1981 Elsevier, De Mayer et al. eds., pp. 111–114.
Silverman, R.H. et al.: In *Lymphokines & Interf.: A Practical Approach,* Clemens et al. eds., IRL Press, Wash. D.C. 1987, pp. 149–193.
Justesen, J. et al.: *Nucleic Acids Res.,* 8(14):? (1980).
Torrence, P.F. et al.: *Chemica Scripta,* 26:191–197 (1986).
Torrence, P.F. et al.: *Molec. Aspects Med.,* 5:129–171 (1982).
Chousterman, S. et al.: *J. Biol. Chem.,* 262(10):4806–4811 (Apr. 1987).
Chelbi–Alix, M.K. et al.: *J. Biol. Chem.,* 260(13):7960–7964 (Jul. 1985).
Besancon, F. et al.: *Biochem. & Biophys. Res. Comm.,* 103(1):16–24 (Nov. 1981).
Lab, M. et al.: *Biochem. & Biophys. Res. Comm.,* 105(2):412–418 (Mar. 1982).
Dougherty, J.P. et al.: *J. Biol. Chem.,* 255(9):3813–3816 (May 1980).
Chebath, J. et al.: *Nature,* 330:587–588 (Dec. 1987).
Ghosh, S.K. et al.: *J. Biol. Chem.,* 266(23):15293–15299 (Aug. 1991).
Minks, M.A. et al.: *J. Biol. Chem.,* 254(20):10180–10183 (Oct. 1979).
Wu, J.M. et al.: *AIDS Res.,* 2(2):127–131 (1986).
Schroder, H.C. et al.: *J. Biol. Chem.,* 264(10):5669–5673 (Apr. 1989).
Schroder, H.C. et al.: *AIDS Res. & Human Retrov.,* 6(5):659–672 (1990).
Schroder, H.C. et al.: *Biol. Chem. Hoppe–Seyler,* 369:985–995 (Sep. 1988).
Agy, M.B. et al.: *Virology,* 177:251–258 (1990).
Suhadolnik, R.J. et al.: *Photoaffinity,* 27(24):8840–8846 (1988).
Read, S.E. et al.: *J. Infect. Dis.,* 152(3):466–472 (Sep. 1985).
Ghora, B.K. et al.: *Cell,* 15:1055–1066 (Nov. 1978).
Samanta, H. et al.: *J. Biol. Chem.,* 255(20)9807–9813 (Oct. 1980).
Broeze, R.J. et al.: *J. Interf. Res.,* 1(2):191–201 (1981).
Yang, K. et al.: *J. Biol. Chem.,* 256(17):9324–9328 (Sep. 1981).
Cayley, P.J. et al.: *Eur. J. Biochem.,* 143:165–174 (1984).
Brown, R.E. et al.: *Meth. in Enzymology,* 79:208–216 (1981).
Hersch, C.L. et al.: *J. Biol. Chem.,* 259(3):1731–1737 (Feb. 1984).
Rice, A.P. et al.: *J. Virol.,* 50(1):220–228 (Apr. 1984).
Rice, A.P. et al.: *J. Virol.,* 56(3):1041–1044 (Dec. 1985).
Williams, B.R.G. et al.: *Eur. J. Biochem.,* 92:455–462 (1978).
Cayley, P.J. et al.: *Eur. J. Biochem.,* 122:601–608 (1982).
Reid, T.R. et al.: *Anal. Biochem.,* 136:136–141 (1984).
Williams, B.R.G. et al.: *Nucleic Acids Res.,* 6(4):1335–1350 (Apr. 1979).
Foster, G.R. et al.: *Proc. natl. Acad. Sci. USA,* 88:2888–2892 (Apr. 1991).
Cayley, P.J. et al.: *Interferons,* ??:143–157 (Academic Press 1992).
Lebleu, B. et al.: *Proc. Natl. Acad. Sci. USA,* 73(9):3107–3111 (Sep. 1976).
Bisbal, C. et al.: *Biochemistry,* 26:5172–5178 (1987).
Mechti, N. et al.: *Differentiation,* 29:136–139 (1985).
Bayard, B. et al.: *Biochemistry,* 25:3730–3736 (1986).
Stark, G.R. et al.: *Nature,* 278:471–473 (Mar. 1979).
Hovanessian, A.G. et al.: *Proc. Natl. Acad. Sci. USA,* 76(&):3261–3265 (Jul. 1979).
Buffet–Janvresse, C. et al.: *J. Interf. Res.,* 6:85–96 (1986).

Ogunkolade, W. et al.: *J. Interf. Res.*, 7:245–254 (1987).
Riviere, Y. et al.: *Ann. Immunol. (Inst. Pasteur)*, 135(C):333–343 (1984).
Marcovistz, R. et al.: *J. gen. Virol.*, 65:995–997 (1984).
Hovanessian, A.G. et al.: *Virology*, 104:195–204 (1980).
Laurence, L. et al.: *Virology*, 143:290–299 (1985).
Chapekar, M.S. et al.: *Biochem. & Biophys. Res. Commun.*, 151(3):1180–1187 (Mar. 1988).
Floyd–Smith, G. et al.: *Proc. of Soc. for Exper. Bio. & Medicine*, 189:329–337 (1988).
Esteban, M. et al.: *J. gen. Virol.*, 67:801–808 (1986).
Paez, E. et al.: *J. Virol.*, 56(1):75–84 (Oct. 1985).
Paez, E. et al.: *Virology*, 134:12–28 (1984).
Paez, E. et al.: *Virology*, 134:29–39 (1984).
Esteban, M. et al.: *Virology*, 134:40–51 (1984).
Santoro, M.G. et al.: *Biochem. & Biophys. Res. Commun.*, 116(2):442–448 (Oct. 1983).
Benavente, J. et al.: *J. Virol.*, 51(2):866–871 (Sep. 1984).
Eppstein, D.A. et al.: *Nature*, 302:723–724 (Apr. 1983).
Eppstein, D.A. et al.: *Virology*, 131:341–354 (1983).
Eppstein, D.A. et al.: *J. Interf. Res.*, 3(3):305–311 (1983).
Eppstein, D.A. et al.: *J. Biol. Chem.*, 26(13):5999–6003 (May 1986).
Drocourt, J. et al.: *Nucleic Acids Res.*, 10(6):2163–2174 (1982).
Rice, A.P. et al.: *J. Virol.*, 54(3):894–898 (Jun. 1985).
Jamoulle, J.–C. et al.: *Biochemistry*, 26:376–383 (1987).
Torrence, P.F. et al.: *Analyt. Biochem.*, 129:103–110 (1983).
Johnston, M.I. et al.: *J. Biol. Chem.*, 262(17):8377–8382 (Jun. 1987).
Mittnacht, S. et al.: *J. gen. Virol.*, 68:2945–2951 (1987).
Defilippi, P. et al.: *FEBS* 3525, 198(2):326–332 (Mar. 1986).
Ankel, H. et al.: *J. gen. Virol.*, 66:2355–2364 (1985).
Hovanessian, A.G.: *J. Interf. Res.*, 11:199–205 (1991).
Marie, I. et al.: *J. Biol. Chm.*, 267(14):9933–9939 (1992).
Hovanessian, A.g. et al.: *Virology*, 101:81–90 (1980).
Hovanessian, A.G. et al.: *EMBO*, 6(5):1273–1280 (1987).
Flenniken, A.M. et al.: *J. Virol.*, 62(9):3077–3083 (Sep. 1988).
Wood, J.N. et al.: *Nature*, 282:74–76 (Nov. 1979).
Hovanessian, A.G. et al.: *J. Interf. Res.*, 1(2):179–190 (1981).
Hovanessian, A.G. et al.: *Proc. Natl. Acad. Sci. USA*, 76(7):3261–325 (Jul. 1979).
Galabru, J. et al.: *J. gen. Virol.*, 66:711–718 (1985).
Buffet–Janvresse, C. et al.: *Proc. of Soc. for Exp. Biol. & Medicine*, 175:169–175 (1984).
Knight Jr., E. et al.: *Proc. Natl. Acad. Sci. USA*, 82:1151–1154 (Feb. 1985).
Kimichi, A.: *J. Interf. Res.*, 1(4):559–569 (1981).
Cleveland, D.W. et al.: *J. Biol. Chem.*, 252(3):1102–1106 (Feb. 1977).
Bayard, B. et al.: *Eur. J. Biochem.*, 142:291–298 (1984).
Bayard, B. et al.: *Eur. J. Biochem.*, 151:319–325 (1985).
Bayard, B. et al.: *Biochemistry*, 25:3730–3736 (1986).
Nilsen, T.W. et al.: *J. Virol.*, 42(3):1039–1045 (Jun. 1982).
Baglioni, C. et al.: *J. Biol. Chem.*, 256(7):3253–3257 (Apr. 1981).
Nilsen, T.W. et al.: *Biochemistry*, 19:5574–5579 (1980).
Baglioni, C. et al.: *Biochemistry*, 20:758–762 (1981).
Nilsen, T.W. et al.: *Virology*, 122:498–502 (1982).
Nilsen, T.W. et al.: *Molecular & Cellular Biol.*, 3(1):64–69 (Jan. 1983).
Baglioni, C. et al.: *Cell*, 17:255–264 (Jun. 1979).
Nilsen, T.W. et al.: *Molecular & Cellular Biol.*, 2(2):154–160 (Feb. 1982).
Baglioni, C. et al.: *J. Virol.*, 52(3):865–871 (Dec. 1984).
Williams, G.J. et al.: *Virology*, 151:233–242 (1986).
Minks, M.A. et al.: *Nucleic Acids Res.*, 6(2):767–780 (Feb. 1979).
Baglioni, C.: Chapter 8, *The Molecular Mediators of Interferon Action*, pp. 153–168.
Nilsen, T.W. et al.: *J. Biol. Chem.*, 256(15):7806–7811 (Aug. 1981).
Nilsen, T.W. et al.: *J. Biol. Chem.*, 257(4):1602–1605 (Feb. 1982).
Verhaegen, M. et al.: *Proc. Natl. Acad. Sci. USA*, 77(8):4479–4483 (Aug. 1980).
Verhaegen–Lewalle, M. et al.: *Eur. J. Biochem.*, 126:639–643 (1982).
Vandenbussche, P. et al.: *Virology*, 111:11–22 (1981).
Chebath, J. et al.: *J. Biol. Chem.*, 262(8):3852–3857 (1987).
Sperling, J. et al.: *Proc. Natl. Acad. Sci. USA*, 88:10377–10381 (Dec. 1991).
Alarcon, B. et al.: *J. Virol.*, 52(1):183–187 (Oct. 1984).
Cailla, H. et al.: *Radioimmunoassay and Related Procedures in Medicine* 1982, Int'l Atomic Energy Agency Vienna, 1982.
Cailla, H. et al.: *Proc. Natl. Acad. Sci. USA*, 79:4742–4746 (Aug. 1982).
Marti, J. et al.: *Nucleosides & Nucleotides*, 7(4):479–495 (1988).
Trujillo, M.A. et al.: *Eur. J. Biochem.*, 169:167–173 (1987).
Laurence, L. et al.: *Proc. Natl. Acad. Sci. USA*, 81:2322–2326 (Apr. 1984).
Hovanessian, A.G. et al.: *Eur. J. Biochem.*, 93:515–526 (1979).
Kerr, I.M. et al.: *The Biology of the Interferon System* 1983, Elsevier: De Maeyer et al. eds., pp. 213–222.
Etienne–Smekens, M. et al.: *FEBS L.*, 125(2):146–150 (Mar. 1981).
Smekens–Etienne, M. et al.: *Eur. J. Biochem.*, 130:269–273 (1983).
Wathelet, M. et al.: *FEBS L.*, 196(1):113–120 (Feb. 1986).
Verhaegen–Lewalle, M. et al.: *J. Virol.*, ?:425–434 (1981).
Haugh, M.C. et al.: *Eur. J. Biochem.*, 132:77–84 (1983).
Martin, E.M. et al.: *Eur. J. Biochem.*, 95:295–307 (1979).
Squire, J. et al.: *Genomics*, 19:174–175 (1994).
Fujihara, M. et al.: *J. Interf. Res.*, 9:691–707 (1989).
Squire, J. et al.: *Genomics* (Dec.), pp. 17–19.
Hassel, B.A. et al.: *EMBO*, 12(8):3297–3304 (1993).
Nilsen, T.W. et al.: *Nature*, 286:178–181 (Jul. 1980).
Krishnan, I. et al.: *Nature*, 285:485–488 (Jun. 1980).
Krishnan, I. et al.: *Mol. & Cell. Biol.*, 1(10):932–938 (Oct. 1981).
Krishnan, I. et al.: *Proc. Natl. Acad. Sci. USA*, 77(11):6506–6510 (Nov. 1980).
Krishnan, I. et al.: *Virology*, 111:666–670 (1981).
Minks, M.A. et al.: *J. Biol. Chem.*, 254(12):5058–5064 (Jun. 1979).
Minks, M.A. et al.: *J. Biol. Chem.*, 255(13):6403–6407 (Jul. 1980).
West, D.K. et al.: *Mol. & Cell. Biol.* 2(11):1436–1443 (Nov. 1982).
Ball, L.A.: *Virology*, 94:282–296 (1979).
Ball, L.A. et al.: *Proc. Natl. Acad. Sci. USA*, 75(3):1167–1171 (Mar. 1978).
Creasey, A.A. et al.: In press, *Molecular and Cellular Biology* (1983), pp. 1–28.

Eds. Williams, B.R.G. and Silverman, R.H.: *The 2–5A System,* Proc. of 6th Int'l Symp. of Res. Inst. Hosp. for Sick Children, Toronto, Ontario, Canada, Jun. 3–5, 1985.
Young, et al.: *Science,* 222:778–782 (1983).
Gerald, et al.: *Biochem. Biophys. Acta.,* 866:1–14 (1986).
Murhammer, et al.: *Appl. Biochem. Biotechnol.,* 31:283–310 (1991).
Silverman, et al.: *J. Cell. Biochem.,* Suppl. 16B:163 (1992).
Hassel, et al.: *J. Cell. Biochem.,* Suppl. 17C:177 (1993).
Hassel, et al.: *J. Interferon Res.,* 12(Suppl. 1):S42 (1992).
Zhou, et al.: *J. Interferon Res.,* 12(Suppl. 1):S57 (1992).
Nejidat et al (1990) Physiologia Plantarum 80:662–668.
Gergerich et al (1988) Phytopathology 78(3):270–272.
Cuozzo et al. (1988) Bio/Technology 6:549–555.

THE 2-5A SYSTEM

COMPLETE CODING SEQUENCE OF HUMAN 2DR

FIG. 3B1

```
     -103 aatcccaactTacactcaaagctt
cttgattaagtgctaggagataaattgcattt ctcaaggaaaagctaaaagtgtagcaggtggcatttaccgtc
                                                                              60
ATG GAG AGC AGG GAT CAT AAC AAC CCC CAG GAG GGA CCC ACG TCC TCC AGC GGT AGA AGG    60
Met Glu Ser Arg Asp His Asn Asn Pro Gln Glu Gly Pro Thr Ser Ser Ser Gly Arg Arg    20

GCT GCA GTG GAA GAC AAT CAC TTG CTG ATT AAA GCT GTT CAA AAC GAA GAT GTT GAC CTG   120
Ala Ala Val Glu Asp Asn His Leu Leu Ile Lys Ala Val Gln Asn Glu Asp Val Asp Leu    40

GTC CAG CAA TTG CTG GAA GGT GGA GCC AAT GTT AAT TTC CAG GAA GAG GAA GGG GGC TGG   180
Val Gln Gln Leu Leu Glu Gly Gly Ala Asn Val Asn Phe Gln Glu Glu Glu Gly Gly Trp    60

ACA CCT CTG CAT AAC GCA GTA CAA ATG CAG GAC ATT GTG GAA CTT CTG CTT CGT           240
Thr Pro Leu His Asn Ala Val Gln Met Ser Arg Glu Asp Ile Val Glu Leu Leu Leu Arg    80

CAT GGT GCT GAC CCT GTT CTG AGG AAG AAT GGG GCC ACG CTT TTT ATC CTC GCA GCG       300
His Gly Ala Asp Pro Val Leu Arg Lys Asn Gly Ala Thr Leu Phe Ile Leu Ala Ala      100

ATT GCG GGG AGC GTG AAG CTG CTG AAA CTT TTC CTT TCT AAA GGA GCA GAT GTC AAT GAG   360
Ile Ala Gly Ser Val Lys Leu Leu Lys Leu Phe Leu Ser Lys Gly Ala Asp Val Asn Glu   120

TGT GAT TTT TAT GGC TTC ACA GCC TTC ATG GAA GCC GCT GTG TAT GGT AAG GTC AAA GCC   420
Cys Asp Phe Tyr Gly Phe Thr Ala Phe Met Glu Ala Ala Val Tyr Gly Lys Val Lys Ala   140

CTA AAA TTC CTT TAT GGC TTT TAT AGA GGA GCA AAT GTG AAT TTG AGG CGA AAG ACA AAG GAG GAT   480
Leu Lys Phe Leu Tyr Gly Phe Tyr Arg Gly Ala Asn Val Asn Leu Arg Arg Lys Thr Lys Glu Asp   160

CAA GAG CGG CTG AGG AAA GGA GGG GCC ACA GCT CTC ATG GAC GCT GAA AAA GGA CAC       540
Gln Glu Arg Leu Arg Lys Gly Gly Ala Thr Ala Leu Met Asp Ala Glu Lys Gly His       180

GTA GAG GTC TTG AAG ATT CTC CTT GAT GAG ATG GGG GCA GAT GTA AAC GCC TGT GAC AAT   600
Val Glu Val Leu Lys Ile Leu Leu Asp Glu Met Gly Ala Asp Val Asn Ala Cys Asp Asn   200
```

FIG. 3B2

```
ATG GGC AGA AAT GCC TTG ATC CAT GCT CTC CTG AGC TCT GAC GAT AGT GAT GTG GAG GCT    660
Met Gly Arg Asn Ala Leu Ile His Ala Leu Leu Ser Ser Asp Asp Ser Asp Val Glu Ala    220

ATT ACG CAT CTG CTG CTG GAC CAT GGG GCT GAT GTC AAT GTG AGG GGA GAA AGA GGG AAG    720
Ile Thr His Leu Leu Leu Asp His Gly Ala Asp Val Asn Val Arg Gly Glu Arg Gly Lys    240

ACT CCC CTG GCA GTG CTG GAG AAG AAG CAC TTG GGT TTG GTG CAG AGG CTT CTG GAG        780
Thr Pro Leu Ala Val Leu Glu Lys Lys His Leu Gly Leu Val Gln Arg Leu Leu Glu        260

CAA GAG CAC ATA GAG ATT AAT GAC ACA GAC AGT GAT GGC AAA ACA GCA CTG CTT GCT        840
Gln Glu His Ile Glu Ile Asn Asp Thr Asp Ser Asp Gly Lys Thr Ala Leu Leu Ala        280

GTT GAA CTC AAA CTG AAA ATC GCC GAG TTG CTG TGC AAA CGT GGA GCC AGT ACA GAT        900
Val Glu Leu Lys Leu Lys Ile Ala Glu Leu Leu Cys Lys Arg Gly Ala Ser Thr Asp        300

TGT GGG GAT CTT GTT ATG ACA GCG AGG CGG AAT TAT GAC CAT TCC CTT GTG AAG GTT CTT    960
Cys Gly Asp Leu Val Met Thr Ala Arg Arg Asn Tyr Asp His Ser Leu Val Lys Val Leu    320

CTC TCT CAT GGA GCC AAA GAA GAT TTT CAC CCT CCT GCT GAA GAC TGG AAG CCT CAG AGC    1020
Leu Ser His Gly Ala Lys Glu Asp Phe His Pro Pro Ala Glu Asp Trp Lys Pro Gln Ser    340

TCA CAC TGG GGG GCA GCC CTG AAG GAT CTC CAC AGA ATA TAC CGC CCT ATG ATT GGC AAA    1080
Ser His Trp Gly Ala Ala Leu Lys Asp Leu His Arg Ile Tyr Arg Pro Met Ile Gly Lys    360

CTC AAG TTC TTT ATT GAT GAA AAA TAC AAA ATT GCT GAT ACT TCA GAA GGA GGC ATC TAC    1140
Leu Lys Phe Phe Ile Asp Glu Lys Tyr Lys Ile Ala Asp Thr Ser Glu Gly Gly Ile Tyr    380

CTG GGG TTC TAT GAG AAG CAA GAA GTA GCT GTG AAG ACG TTC TGT GAG GGC AGC CCA CGT    1200
Leu Gly Phe Tyr Glu Lys Gln Glu Val Ala Val Lys Thr Phe Cys Glu Gly Ser Pro Arg    400

GCA CAG CGG GAA GTC TCT TGT CTG CAA CGA GAG AAC AGT CAC TTG GTG ACA TTC            1260
Ala Gln Arg Glu Val Ser Cys Leu Gln Ser Arg Glu Asn Ser His Leu Val Thr Phe        420
```

FIG. 3B3

```
TAT GGG AGT GAG AGC CAC AGG GGC CAC TTG TTT GTG TGT GTC ACC CTC TGT GAG CAG ACT    1320
Tyr Gly Ser Glu Ser His Arg Gly His Leu Phe Val Cys Val Thr Leu Cys Glu Gln Thr     440

CTG GAA GCG TGT TTG GAT GTG CAC AGA GGG GAA GAT GTG GAA AAT GAG GAA GAT GAA TTT    1380
Leu Glu Ala Cys Leu Asp Val His Arg Gly Glu Asp Val Glu Asn Glu Glu Asp Glu Phe     460

GCC CGA AAT GTC CTG TCA TCT ATA TTT AAG GCT GTT CAA GAA CTA CAC TTG TCC TGT GGA    1440
Ala Arg Asn Val Leu Ser Ser Ile Phe Lys Ala Val Gln Glu Leu His Leu Ser Cys Gly     480

TAC ACC CAC CAG GAT CTG CAA CCA CAA AAC ATC TTA ATA GAT TCT AAG CGT GCT CAC        1500
Tyr Thr His Gln Asp Leu Gln Pro Gln Asn Ile Leu Ile Asp Ser Lys Arg Ala His         500

CTG GCA GAT TTT GAT AAG AGC ATC AAG TGG GCT GGA GAT CCA CAG GAA GTC AAG AGA GAT    1560
Leu Ala Asp Phe Asp Lys Ser Ile Lys Trp Ala Gly Asp Pro Gln Glu Val Lys Arg Asp     520

CTA GAG GAC CTT GGA CGG CTG GTC CTC TAT GTG GTA AAG CTT CAA CTT TCT CCA GAT GAG GAA ACT AAG    1620
Leu Glu Asp Leu Gly Arg Leu Val Leu Tyr Val Val Lys Leu Gln Leu Ser Pro Asp Glu Glu Thr Lys     540

GAT CTG AAA GCT CAA AGT AAT GAA GAG GTG GAA CAT CCT GGG TTC CAT CGT CTC TTC TTC    1680
Asp Leu Lys Ala Gln Ser Asn Glu Glu Val Glu His Pro Gly Phe His Arg Leu Phe Phe     560

GAC CTC ATT CAT CGT CTC TTC TTC TGG ACT TGG GAG AGC CGC TAT AGG CGC TAT AGG        1740
Asp Leu Ile His Arg Leu Phe Phe Trp Thr Trp Glu Ser Arg Tyr Arg Tyr Arg            580

CTG GGT CAT CCC TTC TTT TGG ACT TGG ACG CTT CGG AAT GTG GGA                        1800
Leu Gly His Pro Phe Phe Trp Thr Trp Thr Leu Arg Asn Val Gly                        600

AAT GAA TCC GAC ATC AAA ACA CGA AAA TCT GAA AGT GAG ATC CTC AGA CTA CTG CAA CCT    1860
Asn Glu Ser Asp Ile Lys Thr Arg Lys Ser Glu Ser Glu Ile Leu Arg Leu Leu Gln Pro     620

GGG CCT TCT GAA CAT TCC AAA AGT TTT GAC AAG TGG ACG ACT AAG ATT AAT GAA TGT GTT    1920
Gly Pro Ser Glu His Ser Lys Ser Phe Asp Lys Trp Thr Thr Lys Ile Asn Glu Cys Val     640
```

FIG. 3B4

```
ATG AAA AAT AAG TTT TAT GAA AAA AGA GGC AAT TTC TAC CAG AAC ACT GTG GGT   1980
Met Lys Met Asn Lys Phe Tyr Glu Lys Arg Gly Asn Phe Tyr Gln Asn Thr Val Gly   660

GAT CTG CTA AAG TTC ATC CGG AAT TTG GGA GAA CAC ATT GAT GAA GAA AAG CAT AAA AAG   2040
Asp Leu Leu Lys Phe Ile Arg Asn Leu Gly Glu His Ile Asp Glu Glu Lys His Lys Lys   680

ATG AAA TTA ATT GGA GAC CCT TCC TAT TTT CAG AAG ACA TTT CCA GAT CTG GTG   2100
Met Lys Leu Lys Ile Gly Asp Pro Ser Leu Tyr Phe Gln Lys Thr Phe Pro Asp Leu Val   700

ATC TAT GTC TAC ACA AAA CTA CAG AAC ACA GAA TAT AGA AAG CAT TTC CCC CAA ACC CAC   2160
Ile Tyr Val Tyr Thr Lys Leu Gln Asn Thr Glu Tyr Arg Lys His Phe Pro Gln Thr His   720

AGT CCA AAC AAA CCT CAG TGT GAT GGA GCT GGT GGG GCC AGT GGG TTG GCC AGC CCT GGG   2220
Ser Pro Asn Lys Pro Gln Cys Asp Gly Ala Gly Gly Ala Ser Gly Leu Ala Ser Pro Gly   740

TGC 2223  tgatggactgattgctgagttcagggaactactattagctgtagagtccctggcaaatcacaacat  2292
Cys 741 tctgggcctttaactcaccaggttgcttgtgaggatgagttgcatagctgatatgtcagtccctgcatcgtg         2367
tattccatatgtctataacaaagcaatatataccagactacacactagtccataagctttaccactactgga         2442
ggacattctgctaagatccttgtcaattgcaccaaaagaatgagtgcctgaccctaatgctgcatatgtt          2517
acaattctctcacttaatttcccaatgatcttgcaaaaacaggattatcatcccattaagaactgaggaacc        2592
tgagactcagagagtgtgagctactggcaccctaaaactattcaatctcttccaggctcttccagatgaggcccaaaacat  2667
ttattggtacctctcattgggcacctaaaactaactatctccaggctcttccagatgaggcccaaaacat           2742
atagggttccaggaatcctcattcattcagtattcattgagcatctagtataagtctgggcactgatg             2817
catgaatt    2825
```

FIG. 4A

P-loop cores- ▰  Cys-rich- ▰  PK homology- ▱

| | | |
|---|---|---|
| Human | MESRDHNNPQ EGPTSSSGRR AAVEDNHLLI KAVQNEDVDL VQQLLEGGAN VNFQEEEGGW | 60 |
| Murine | METPDYNTPQ GGTPSAGSQR TVVEDDSSLI KAVQKGDVVR VQQLLEKGAD ANACEDTWGW | 60 |
| Human | TPLHNAVQMS REDIVELLLR HGADPVLRKK NGATLFILAA IAGSVKLLKL FLSKGADVNE | 120 |
| Murine | TPLHNAVQAG RVDIVNLLLS HGADPHRRKK NGATPFIIAG IQGDVKLLEI LLSCGADVNE | 120 |
| Human | CDFYGFTAFM EAAVYGKVKA LKFLYKRGAN LKFFLYKRGAN VNLRRKTKED QERLRKGGAT ALMDAAEKGH | 180 |
| Murine | CDENGFTAFM EAAERGNAEA LRFLFAKGAN VNLRRQTTKD KRRLKQGGAT ALMSAAEKGH | 180 |
| Human | VEVLKILLDE MGADVNACDN MGRNALIHAL LSSDDSDVEA ITHLLLDHGA DVNVRGERGK | 240 |
| Murine | LEVLRILLND MKAEVDARDN MGRNALIRTL LNWDCENVEE ITSILIQHGA DVNVRGERGK | 240 |
| Human | TPLILAVEKK HLGLVQRLLE QEHIEINDTD SDGKTALLLA VELKLKKIAE LLCKRGASTD | 300 |
| Murine | TPLIAAVERK HTGLVQMLLS REGINIDARD NEGKTALLIA VDKQLKEIVQ LLLEKGA-DK | 299 |
| Human | CGDLVMTARR NYDHSLVKVL LSHGAKEDFH PPAEDWKPQS SHWGAALKDL HRIYRPMIGK | 360 |
| Murine | CDDLVWIARR NHDYHLVKLL LPYVANPDTD PPAGDWSPHS SRWGTALKSL HSMTRPMIGK | 359 |
| Human | LKFFIDEKYK IADTSEGGIY LGFYEKQEVA VKTFCEGSPR AQREVSCLQS SRENSHLVTF | 420 |
| Murine | LKIFIHDDYK IAGTSEGAVY LGIYDNREVA VKVFRENSPR GCKEVSCLRD CGDHSNLVAF | 419 |

FIG. 4B

| | | | |
|---|---|---|---|
| Human | — | YGSESHRGHL FVCVTLCEQT LEACLDVHRG EDVENEEDEF ARNVLSSIFK AVQELHLSCG | 480 |
| Murine | — | YGREDDKGCL YVCVSLCEWT LEEFLRLPRE EPVENGEDKF AHSILLSIFE GVQKLHLH-G | 478 |
| Human | — | YTHQDLQPQN ILIDSKKKRAH LADFDKSIKW AGDPQEVKRD LEDLGRLVLY VVKKGSISFE | 540 |
| Murine | — | YSHQDLQPQN ILIDSKKKAVR LADFDQSIRW MGESQMVRRD LEDLGRLVLY VVMKGEIPFE | 538 |
| Human | — | DLKAQSNEEV VQLSPDEETK DLIHRLFHPG EHVRDCLSDL LGHPFFWTWE SRYRTLRNVG | 600 |
| Murine | — | TLKTQNDEVL LTMSPDEETK DLIHCLFSPG ENVKNCLVDL LGHPFFWTWE NRYRTLRNVG | 598 |
| Human | — | NESDIKTRKS ESEILRLLQP GPSEHSKSFD KWTTKINECV MKKMNKFYEK R-GNFYQNTV | 659 |
| Murine | — | NESDIKVRKC KSDLLRLLQH QTLEPPRSFD QWTSKIDKNV MDEMNHFYEK RKKNPYQDTV | 658 |
| Human | — | GDLLKFIRNL GEHIDEEKHK KMKLKIGDPS LYFQKTFPDL VIYVYTKLQN TEYRKHFPQT | 719 |
| Murine | — | GDLLKFIRNI GEHINEEKKR G---------- ---------- ---------- ---------- | 679 |
| Human | — | HSPNKPQCDG AGGASGLASP GC | 741 |

FIG. 10A

|  | | | |
|---|---|---|---|
| ANKYRIN CONSENSUS: | | -G-TPLHVAA--GH---V--LL---GA---D---<br>S A A N | |
| REPEAT 1 | HUMAN 58<br>MURINE | GG WTPLHNAVQMSREDIVELLLRHGADPVLRKK<br>WG WTPLHNAVQAGRVDDIVNLLLSHGADPHRRKK | 90 |
| REPEAT 2 | HUMAN 91<br>MURINE | NG ATLFILAAIAGSVKLLLKLFLSKGADVNECDF<br>NG ATPFIIAGIQGDVKLLLEILLLSCGADVNECDE | 123 |
| REPEAT 3 | HUMAN 124<br>MURINE | YG FTAFMEAAVYGKVKALLLKFLYKRGANVNLRRK<br>NG FTAFMEAAERGNAEALRFLFAKGANVNLRRQ | 156 |
| REPEAT 4 | HUMAN 238<br>MURINE | RGKTPLILAVEKKHLGLVQRLLEQEHIEINDTD<br>RGKTPLIAAVERKHTGLVQMLLSREGINIDARD | 270 |

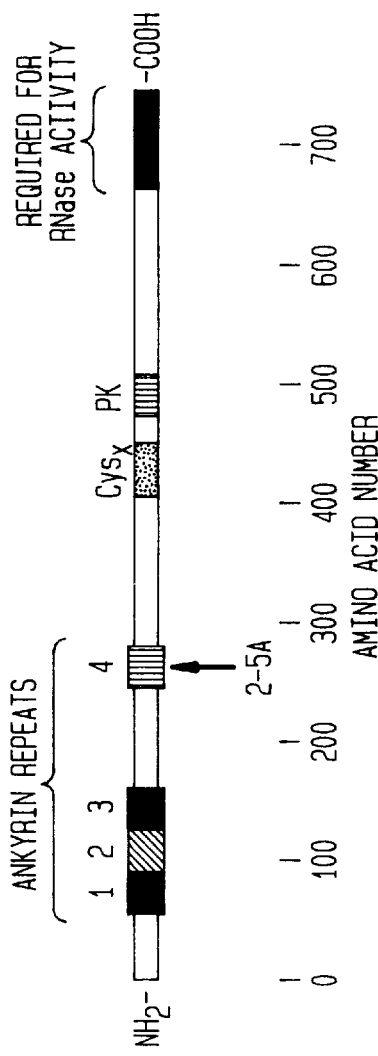

ID SEQ NO:3 :

```
   1  cagtttctgg  agcaaattca  gtttgccttc  ctggatttgt  aaattgtaat  gacctcaaaa
  61  ctttagcagt  tcttccatct  gactcaggtt  tgcttctctg  gcggtcttca  gaatcaacat
 121  ccacacttcc  gtgattatct  gcgtgcattt  tggacaaagc  ttccaaccag  gatacgggaa
 181  gaagaaatgg  ctggtgatct  ttcagcaggt  ttcttcatgg  aggaacttaa  tacataccgt
 241  cagaagcagg  gagtagtact  taaatatcaa  gaactgccta  attcaggacc  tccacatgat
 301  aggaggttta  catttcaagt  tataatagat  ggaagagaat  ttccagaagg  tgaaggtaga
 361  tcaaagaagg  aagcaaaaaa  tgccgcagcc  aaattagctg  ttgagatact  taataaggaa
 421  aagaaggcag  ttagtccttt  attattgaca  acaacgaatt  cttcagaagg  attatccatg
 481  gggaattaca  taggccttat  caatagaatt  gcccagaaga  aaagactaac  tgtaaattat
 541  gaacagtgtg  catcggggt   gcatgggcca  gaaggatttc  attataaatg  caaaatggga
 601  cagaaagaat  atagtattgg  tacaggttct  actaaacagg  aagcaaaaca  attggccgct
 661  aaacttgcat  atcttcagat  attatcagaa  gaaacctcag  tgaaatctga  ctacctgtcc
 721  tctggttctt  ttgctactac  gtgtgagtcc  caaagcaact  ctttagtgac  cagcacactc
 781  gcttctgaat  catcatctga  aggtgacttc  tcagcagata  catcagagat  aaattctaac
 841  agtgacagtt  taaacagttc  ttcgttgctt  atgaatggtc  tcagaaataa  tcaaaggaag
 901  gcaaaaagat  ctttggcacc  cagatttgac  cttcctgaca  tgaaagaaac  aaagtatact
 961  gtggacaaga  ggtttggcat  ggattttaaa  gaaatagaat  taattggctc  aggtggattt
1021  ggccaagttt  tcaaagcaaa  acacagaatt  gacggaaaga  cttacgttat  taaacgtgtt
1081  aaatataata  acgagaaggc  ggagcgtgaa  gtaaaagcat  tggcaaaact  tgatcatgta
1141  aatattgttc  actacaatgg  ctgttgggat  ggatttgatt  atgatcctga  gaccagtgat
1201  gattctcttg  agagcagtga  ttatgatcct  gagaacagca  aaaatagttc  aaggtcaaag
1261  actaagtgcc  ttttcatcca  aatgaattc   tgtgataaag  ggaccttgga  acaatggatt
1321  gaaaaaagaa  gaggcgagaa  actagacaaa  gttttggctt  tggaactctt  tgaacaaata
1381  acaaaagggg  tggattatat  acattcaaaa  aaattaattc  atagagatct  taagccaagt
1441  aatatattct  tagtagatac  aaaacaagta  aagattggag  actttggact  tgtaacatct
1501  ctgaaaaatg  atggaaagcg  aacaaggagt  aggggaactt  tgcgatacat  gagcccagaa
1561  cagatttctt  cgcaagacta  tggaaaggaa  gtggacctct  acgctttggg  gctaattctt
1621  gctgaacttc  ttcatgtatg  tgacactgct  tttgaaacat  caaagttttt  cacagaccta
1681  cgggatggca  tcatctcaga  tatatttgat  aaaaaagaaa  aaactcttct  acagaaatta
1741  ctctcaaaga  aacctgagga  tcgacctaac  acatctgaaa  tactaaggac  cttgactgtg
1801  tggaagaaaa  gcccagagaa  aaatgaacga  cacacatgtt  agagcccttc  tgaaaaagta
1861  tcctgcttct  gatatgcagt  tttccttaaa  ttatctaaaa  tctgctaggg  aatatcaata
1921  gatatttacc  ttttatttta  atgtttcctt  taatttttta  ctatttttac  taatctttct
1981  gcagaaacag  aaaggtttc   ttcttttgc   ttcaaaaaca  ttcttacatt  ttacttttc
2041  ctggctcatc  tctttatttt  tttttttt   ttttaaagac  agagtctcgc  tctgttgccc
2021  aggctggagt  gcaatgacac  agtcttggct  cactgcaact  tctgcctctt  gggttcaagt
2061  gattcctg    cctcagcctc  ctgagtagct  ggattacagg  catgtgccac  ccacccaact
2221  aatttttgtg  tttttaataa  agacagggtt  tcaccatgtt  ggccaggctg  gtctcaaact
2281  cctgacctca  agtaatccac  ctgcctcggc  ctcccaaagt  gctgggatta  cagggatgag
2341  ccaccgcgcc  cagcctcatc  tctttgttct  aaagatggaa  aaaccacccc  caaattttct
2401  ttttatacta  ttaatgaatc  aatcaattca  tatctattta  ttaaatttct  accgctttta
2461  ggccaaaaaa  atgtaagatc  gttctctgcc  tcacatagct  tacaagccag  ctggagaaat
2521  atggtactca  ttaaaaaaaa  aaaaaaaag   tgatgtacaa  cc
```

FIG. 19

ID SEQ NO:4:

MAGDLSAGFFMEELNTYRQKQGVVLKYQELPNSGPPHDRRFTFQVIID
GREFPEGEGRSKKEAKNAAAKLAVEILNKEKKAVSPLLLTTTNSSEGLS
MGNYIGLINRIAQKKRLTVNYEQCASGVHGPEGFHYKCKMGQKEYSIG
TGSTKQEAKQLAAKLAYLQILSEETSVKSDYLSSGSFATTCESQSNSLV
TSTLASESSSEGDFSADTSEINSNSDSLNSSSLLMNGLRNNQRKAKRS
LAPRFDLPDMKETKYTVDKRFGMDFKEIELIGSGGFGQVFKAKHRIDG
KTYVIKRVKYNNEKAEREVKALAKLDHVNIVHYNGCWDGFDYDPETSD
DSLESSDYDPENSKNSSRSKTKCLFIQMEFCDKGTLEQWIEKRRGEKL
DKVLALELFEQITKGVDYIHSKKLIHRDLKPSNIFLVDTKQVKIGDFGLVT
SLKNDGKRTRSKGTLRYMSPEQISSQDYGKEVDLYALGLILAELLHVCD
TAFETSKFFTDLRDGIISDIFDKKEKTLLQKLLSKKPEDRPNTSEILRTLT
VVWKKSPEKNERHTC

FIG. 20A

ID SEQ NO:5:

```
           10         20         30         40         50
  1 AACTGAAACC AACAGCAGTC CAAGCTCAGT CAGCAGAAGA GATAAAAGCA 60         70         80         90        100
 51 AACAGGTCTG GGAGGCAGTT CTGTTGCCAC TCTCTCTCCT GTCAATGATG 10         20         30         40         50
101 GATCTCAGAA ATACCCCAGC CAAATCTCTG ACAAGTTCA TTGAAGACTA 60         70         80         90        100
151 TCTCTTGCCA GACACGTGTT CCGCATGCA AATCGACCAT GCCATTGACA 10         20         30         40         50
201 TCATCTGTGG GTTCCTGAAG GAAAGGTGCT TCCGAGGTAG CTCCTACCCT 60         70         80         90        100
251 GTGTGTGTGT CCAAGGTGGT AAAGGGTGGC TCCTCAGGCA AGGGCACCAC 10         20         30         40         50
301 CCTCAGAGGC CGATCTGACG CTGACCTGGT TGTCTTCCTC AGTCCTCTCA 60         70         80         90        100
351 GCACTTTTCA GGATCAGTTA AATCGCCGGG GAGAGTTCAT CCAGGAAATT 10         20         30         40         50
401 AGGAGACAGC TGGAAGCCTG TCAAAGAGAG AGAGCACTTT CCGTGAAGTT 60         70         80         90        100
451 TGAGGTCCAG GCTCCACGCT GGGGCAACCC CCGTGCGCTC AGCTTCGTAC 10         20         30         40         50
501 TGAGTTCGCT CCAGCTCGGG GAGGGGGTGG AGTTCGATGT GCTGCCTGCC 60         70         80         90        100
551 TTTGATGCCC TGGGTCAGTT GACTGGCAGC TATAAACCTA ACCCCCAAAT 10         20         30         40         50
601 CTATGTCAAG CTCATCGAGG AGTGCACCGA CCTGCAGAAA GAGGGCGAGT 60         70         80         90        100
651 TCTCCACCTG CTTCACAGAA CTACAGAGAG ACTTCCTGAA GCAGCGCCCC 10         20         30         40         50
701 ACCAAGCTCA AGAGCCTCAT CCGCCTAGTC AAGCACTGGT ACCAAAATTG 60         70         80         90        100
751 TAAGAAGAAG CTTGGGAAGC TGCCACCTCA GTATGCCCTG GAGCTCCTGA 10         20         30         40         50
801 CGGTCTATGC TTGGGAGCGA GGGAGCATGA AAACACATTT CAACACAGCC 60         70         80         90        100
851 CAAGGATTTC GGACGGTCTT GGAATTAGTC ATAAACTACC AGCAACTCTG
```

FIG. 20B

```
                10         20         30         40         50
 901 CATCTACTGG ACAAAGTATT ATGACTTTAA AAACCCCATT ATTGAAAAGT
                60         70         80         90        100
 951 ACCTGAGAAG GCAGCTCACG AAACCCAGGC CTGTGATCCT GGACCCGGCG
                10         20         30         40         50
1001 GACCCTACAG GAAACTTGGG TGGTGGAGAC CCAAAGGGTT GGAGGCAGCT
                60         70         80         90        100
1051 GGCACAAGAG GCTGAGGCCT GGCTGAATTA CCCATGCTTT AAGAATTGGG
                10         20         30         40         50
1101 ATGGGTCCCC AGTGAGCTCC TGGATTCTGC TGGCTGAAAG CAACAGTACA
                60         70         80         90        100
1151 GACGATGAGA CCGACGATCC CAGGACGTAT CAGAAATATG GTTACATTGG
                10         20         30         40         50
1201 AACACATGAG TACCCTCATT TCTCTCATAG ACCCAGCACG CTCCAGGCAG
                60         70         80         90        100
1251 CATCCACCCC ACAGGCAGAA GAGGACTGGA CCTGCACCAT CCTCTGAATG
                10         20         30         40         50
1301 CCAGTGCATC TTGGGGGAAA GGGCTCCAGT GTTATCTGGA CCAGTTCCTT
                60         70         80         90        100
1351 CATTTTCAGG TGGGACTCTT GATCCAGAGA AGACAAAGCT CCTCAGTGAG
                10         20         30         40         50
1401 CTGGTGTATA ATCCAAGACA GAACCCAAGT CTCCTGACTC CTGGCCTTCT
                60         70         80         90        100
1451 ATGCCCTCTA TCCTATCATA GATAACATTC TCCACAGCCT CACTTCATTC
                10         20         30         40         50
1501 CACCTATTCT CTGAAAATAT TCCCTGAGAG AGAACAGAGA GATTTAGATA
                60         70         80         90        100
1551 AGAGAATGAA ATTCCAGCCT TGACTTTCTT CTGTGCACCT GATGGGAGGG
                10         20         30         40         50
1601 TAATGTCTAA TGTATTATCA ATAACAATAA AAATAAAGCA AATACCAAAA
```

FIG. 21

ID SEQ NO:6:

```
          10         20         30         40         50
 1234567890 1234567890 1234567890 1234567890 1234567890
MMDLRNTPAK SLDKFIEDYL LPDTCFRMQI DHAIDIICGF LKERCFRGSS  50
YPVCVSKVVK GGSSGKGTTL RGRSDADLVV FLSPLTTFQD QLNRRGEFTQ 100
EIRRQLEACQ RERALSVKFE VQAPRWGNPR ALSFVLSSLQ LGEGVEFDVL 150
PAFDALGQLT GSYKPNPQIY VKLIEECTDL QKEGEFSTCG TELQRDFLKQ 200
RPTKLKSLIR LVKHWTQNCK KKLGKLPPQY ALELLTVYAW ERGSMKTHFN 250
TAQGFRTVLE LVINYQQLCI YWIKYYDFKN PIIEKYLRRQ LTKPRPVILK 300
PADPTGNLGG GDPKGWRQLA QEAEAWLNYP CFKNWDGSPV SSWILLAESN 350
STDDETDDPR TYQKYGYIGT HEYPHFSHRP STLQAASTPQ AEEDWTCTIL 400
```

ANTIVIRAL TRANSGENIC PLANTS, VECTORS, CELLS AND METHODS

This is a divisional of copending application Ser. No. 08/198,973 filed on 18 Feb. 1994, which is a continuation-in-part of Ser. No. 08/028,086 filed on 8 Mar. 1993 now abandoned.

FIELD OF THE INVENTION

The present invention relates to isolated 2-5A-dependent RNases having the ability to bind 2-5A and/or cleave single stranded RNA when bound to 2-5A, encoding sequences therefor, recombinant nucleotide molecules, recombinant vectors, recombinant cells, and antiviral transgenic plants which express, for example, antiviral animal amino acid sequences which have activity similar or identical to 2-5A-dependent RNase, 2-5A synthetase and/or PKR.

BACKGROUND

Control of RNA degradation is a critical cell function, and gene expression is often regulated at the level of RNA stability. See, e.g., Shaw, G. and Kamen, R., Cell, 46:659–667 (1986). Nevertheless, relatively little is known about the bio-chemical pathways that mediate RNA degradation in mammalian or plant systems. For instance, most if not all of the ribonucleases responsible for mRNA turnover in mammalian or plant cells remain unidentified. This was reviewed in Brawerman, G., Cell, 57:9–10 (1989).

Presently, the 2-5A system is believed to be the only well-characterized RNA degradation pathway from higher animals including man. See FIG. 1. See also, e.g., Kerr, I. M. and Brown, R. E., Prod. Natl. Acad. Sci. U.S.A., 75:256–260 (1978) and Cayley, P. J. et al., Biophys Res. Commun., 108:1243–1250 (1982); reviewed in Sen, G. C. and Lengyel, P., J. Biol. Chem., 267:5017–5020 (1992). The activity of the 2-5A system is believed to be mediated by an endoribonuclease known as 2-5A-dependent RNase. See Clemens, M. J. and Williams, B. R. G., Cell, 13:565–572 (1978). 2-5A-dependent RNase is a unique enzyme in that it requires 2-5A, unusual oligoadenylates with 2',5' phosphodiester linkages, $p_n(A2'p)_nA$, for ribonuclease activity. See Kerr, I. M. and Brown, R. E., Prod. Natl. Acad. Sci. U.S.A., 75:256–260 (1978). 2-5A is produced from ATP by a family of synthetases in reactions requiring double-stranded RNA (dsRNA). See FIG. 1. See also Hovanessian, A. G. et al., Nature, 268:537–539 (1977); Marie, I. and Hovanessian, A. G., J. Biol. Chem., 267:9933–9939 (1992). 2-5A is unstable in cells and in cell-free systems due to the combined action of 2',5'-phosphodiesterase and 5'-phosphatase. See Williams, B. R. G. et al.; Eur. J. Biochem., 92:455–562 (1978); and Johnson, M. I. and Hearl, W. G., J. Biol. Chem., 262:8377–8382 (1987). The interaction of 2-5A-dependent RNase and 2-5A($K_d$=4×10$^{-11}$M), Silverman, R. H. et al., Biol. Chem., 263:7336–7341 (1988), is highly specific. See Knight, M. et al., Nature, 288:189–192 (1980). 2-5A-dependent RNase is believed to have no detectable RNase activity until it is converted to its active state by binding to 2-5A. See Silverman, R. H., Anal. Biochem., 144:450–460 (1985). Activated 2-5A-dependent RNase cleaves single-stranded regions of RNA 3' of UpNp, with preference for UU and UA sequences. See Wreschner, D. H. et al., Nature, 289:414–417 (1981a); and Floyd-Smith, G. et al., Science, 212:1020–1032 (1981). Analysis of inactive 2-5A-dependent RNase from mouse liver revealed it to be a single polypeptide of approximately 80 kDa. See Silverman, R. H. et al., Biol. Chem., 263:7336–7341 (1988).

Although the full scope and biological significance of the 2-5A system remains unknown, studies on the molecular mechanisms of interferon action have provided at least some of the functions. Interferons α, β or γ are believed to induce the accumulation of both 2-5A-dependent RNase, Jacobsen, H. et al., Virology, 125:496–501 (1983A) and Floyd-Smith, G., J. Cellular Biochem., 38:12–21 (1988), and 2-5A synthetases, Hovanessian, A. G. et al., Nature, 268:537–539 (1977), reviewed in Sen, G. C. and Lengyel, P., J. Biol. Chem., 267:5017–5020 (1992). Furthermore, several investigations have implicated the 2-5A system in the mechanism by which interferon inhibits the replication of picornaviruses. Indeed, 2-5A per se and highly specific 2-5A mediated rRNA cleavage products were induced in interferon-treated, encephalomyocarditis virus (EMCV)-infected cells. See Williams, B. R. G., Nature, 282:582–586 (1979); Wreschner, D. H. et al., Nucleic Acids Res., 9:1571–1581 (1981b); and Silverman, R. H. et al., Eur. J. Biochem., 124:131–138 (1982a). In addition, expression of 2-5A synthetase cDNA inhibited the replication of picornaviruses, Chebath, J., Nature, 330:587–588 (1987) and Rysiecki, E. F. et al., J. Interferon Res., 9:649–657 (1989), and the introduction of a 2-5A analogue inhibitor of 2-5A-dependent RNase into cells reduced the interferon-mediated inhibition of EMCV replication. See Watling, D. et al., EMBO J., 4:431–436 (1985). Further, 2-5A-dependent RNase levels were correlated with the anti-EMCV activity of interferon, Kumar, R. et al., J. Virol., 62:3175–3181 (1988), and EMCV-derived dsRNA both bound to and activated 2-5A synthetase in interferon-treated, infected cells. See Gribaudo, G. et al., J. Virol., 65:1948–1757 (1991).

The 2-5A system, however, almost certainly provides functions beyond the antipicornavirus activity of interferons. For instance, introduction of 2-5A into cells, Hovanessian, A. G. and Wood, J. N., Virology, 101:81–90 (1980), or expression of 2-5A synthetase cDNA, Rysiecki, G. et al., J. Interferon Res., 9:649–657 (1989), inhibits cell growth rates. Moreover, 2-5A-dependent RNase levels are elevated in growth arrested cells, Jacobsen, H. et al., Proc. Natl. Acad. Sci. U.S.A., 80:4954–4958 (1983b), and 2-5A synthetase, Stark, G. et al., Nature, 278:471–473 (1979), and 2-5A-dependent RNase levels are induced during cell differentiation. See, e.g., Krause, D. et al., Eur. J. Biochem., 146:611–618 (1985). Therefore, interesting correlations exist between 2-5A-dependent RNase and the fundamental control of cell growth and differentiation suggesting that the 2-5A system may function in general RNA metabolism. The ubiquitous presence of the 2-5A system in reptiles, avians and mammalians certainly supports a wider role for the pathway. See, for example, Cayley, P. J. et al., Biochem. Biophy. Res. Commun., 108:1243–1250 (1982).

While it is presently believed that the 2-5A system is the only well-characterized RNA degradation pathway from higher animals, the dsRNA-dependent protein kinase enzyme, known as PKR, is also thought to have antiviral effects in higher animals. Like the 2-5A synthetase enzyme, it is believed that PKR is stimulated by dsRNA. It is believed that activated PKR phosphorylates the alpha subunit of translation factor eIF$_2$, known as eIF$_2$-alpha, which indirectly inhibits protein synthesis initiation. It is believed that interferons α, β, and γ induce the accumulation of PKR. See Hoavanessian et al.: J. Interferon Res., 9:641–647 (1989).

Like the 2-5A system, the PKR system is also likely to provide functions beyond the antipicornavirus activity of interferons. See Meurs, E. F. et al.: J. Virology, 66:5805–5814 (1992). For example, expression of mutant forms of PKR in NIH 3T3 cells resulted in tumor formation when injected into nude mice. See Meurs, E. F. et al.: *Proc. Natl. Acad. Sci U.S.A.,* 90:232–236 (1993).

In short, the 2-5A system and the PKR system inhibit viral protein synthesis. This is believed to be accomplished by the 2-5A system by degrading mRNA and rRNA whereas the PKR system is believed to accomplish this by indirectly inhibiting protein synthesis initiation.

Viral plant diseases are pandemic and their severity varies from mild symptoms to plant death. The majority of plant viruses are believed to have single stranded RNA genomes. Moreover, it is currently believed that plants are void of the three enzymes discussed above, i.e., PKR, 2-5A synthetase and 2-5A-dependent RNase. See Cayley, P. J. et al.: *Biochem. Biophys Res. Commun.,* 108:1243–1250 (1982) and Devash, Y. et al.: *Biochemistry,* 24:593–599 (1985); but see Crum, C. et al.: *J. Biol. Chem.,* 263:13440–13443 (1988); Hiddinga, H. J. et al.: *Science,* 241:451–453 (1988); Sela, I.: *TIBS,* pp. 31–33 (Feb 1981); and Devash, Y. et al.: *Science,* 216:1415–1416.

Notwithstanding the importance of 2-5A-dependent RNase to the 2-5A system, 2-5A-dependent RNase enzymes having ribonuclease function have not been isolated, purified or sequenced heretofore. Consequently, there is a demand for isolated, active 2-5A-dependent RNases and their complete amino acid sequences, as well as a demand for encoding sequences for active 2-5A-dependent RNases. There is also a demand for plants which are resistant to viruses such as the picornaviruses.

SUMMARY OF THE INVENTION

In brief, the present invention alleviates and overcomes certain of the above-mentioned problems and shortcomings of the present state of the art through the discovery of novel, isolated 2-5A-dependent RNases and encoding sequences therefor.

Broadly speaking, the novel 2-5A dependent RNases of the instant invention are involved in the fundamental control of single stranded RNA decay in animal cells, such as mammals, and are also present in animal cells, such as avian and reptilian cells. More particularly, the novel 2-5A dependent RNases of the present invention have the ability to degrade single stranded RNA, mainly 3' of UpUp or UpAp sequences, after they are activated by binding to 5'-phosphorylated,2',5'-linked oligoadenylates (hereinafter "2-5A"). As a result, it is believed that the novel 2-5A dependent RNases are useful in connection with inhibition of cell growth rates, viral replication and in connection with interferon treatment of viral infection and cancer. As used herein, the term "2-5A-dependent RNase(s)" is used in a broad sense and is meant to include any amino acid sequence which includes a 2-5A binding domain and/or ribonuclease function when the 2-5A-dependent RNase is activated by 2-5A.

The novel 2-5A dependent RNases of the present invention are protein enzymes having molecular weights on the order of between about 74 KDa (murine) and about 84 KDa (human), as determined by gel electrophoresis migration and/or prediction from their respective encoding nucleotide sequences. For example, a human 2-5A-dependent RNase of the instant invention has a molecular weight of about 83,539 Da as determined from the amino acid sequence predicted from the encoding sequence therefor, whereas the murine 2-5A-dependent RNase has a molecular weight of about 74 KDa as determined by gel electrophoresis migration and from prediction of the amino acid sequence from the encoding sequence. While an about 74 KDa molecular weight is reported herein for a murine 2-5A-dependent RNase, it should nevertheless be appreciated that the reported molecular weight is for an incomplete murine 2-5A-dependent RNase. It is nevertheless believed that once completely sequenced, i.e., when an about 84 amino acid end region is identified, the molecular weight of a complete murine 2-5A-dependent RNase will be similar to that of human, i.e., about 84 KDa.

It should also be readily apparent to those versed in this art, however, that since gel electrophoresis migration has been employed to determine molecular weight of a murine 2-5A-dependent RNase, the 74 KDa molecular weight is only an estimate based upon relative migration.

The amino acid sequence for human 2-5A-dependent RNase protein is depicted in FIG. 3 and Table 1. The encoding sequence for the human 2-5A-dependent RNase protein is also set forth in Table 1. The mRNA for human 2-5A-dependent RNase is about 5.0 Kb in size. The virtually complete amino acid sequence for the murine 2-5A-dependent RNase protein and the encoding sequence therefore is depicted in Table 2. The mRNA for murine 2-5A-dependent RNase is about 5.7 Kb in size.

Analysis of the amino acid sequences of the 2-5A-dependent RNases of the present invention have revealed several characteristics unique to the 2-5A-dependent RNases. For example, it has been discovered that the novel 2-5A dependent RNases of the instant invention include the following unique domains which span between the amino terminus and the carboxy terminus. For instance, it has been discovered that there are at least four and possibly as many as nine or more ankyrin repeats, of which three lie closest to the amino terminus. However, while four ankyrin repeats have been discovered, it is believed that there may be additional ankyrin repeats that may total, for instance, about eight or more when the amino acid sequences of the 2-5A-dependent RNases of the present invention are further analyzed. It is believed that these ankyrin repeats may possibly function in protein-protein interaction. Ankyrin repeat 1 generally lies between amino acids designated as 58–90 in Tables 1 and 2. Ankyrin repeat 2 generally lies between amino acids designated as 91–123 in Tables 1 and 2. Ankyrin repeat 3 generally lies between amino acids designated as 124–156 in Tables 1 and 2. Ankyrin repeat 4 generally lies between amino acids designated as 238 and 270 in Tables 1 and 2. See also FIGS. 10A and 10B.

It has also been discovered that the novel 2-5A dependent RNases include a cysteine rich region (which has homology to zinc fingers) that lies closer to the carboxy terminus than the amino terminus which may possibly function in RNA recognition or in formation of protein dimers. The cysteine rich region is believed to include about 5 or 6 cysteine residues which generally lie between amino acids designated as 395–444 in the human sequence as reported in Table 1 and FIG. 4, or between amino acids designated as 401–436 in the murine sequence as reported in Table 2 and FIG. 4.

Still further, it has been discovered that the novel 2-5A dependent RNases include a duplicated phosphate binding (2 P-loops) motif which lies generally within the ankyrin repeat motifs. It is believed that the two P-loops are in the same orientation and constitute the binding domain necessary for binding 2-5A. It is further believed that each P-loop motif includes a lysine residue which is essential for maximum 2-5A binding activity. The lysine residues are designated as 240 and 274 in Tables 1 and 2.

It has been further discovered that the 2-5A-dependent RNase proteins contain an amino acid region which follows the cysteine rich region that is believed to be homologous to protein kinases. Within this region, there is believed to be separate domains designated as domains VI and VII which generally lie between amino acid residues designated as 470–504 in Tables 1 and 2. More particularly, as to the human sequence of 2-5A-dependent RNase, domain VI generally lies between amino acid residues designated as 471–491 and domain VII generally lies between amino acid residures designated as 501–504, as reported in Table 1 and FIG. 4. As to the murine sequence of the 2-5A-dependent RNase, domain VI generally lies between amino acids designated as 470–489 and domain VII generally lies between amino acid residues designated as 499–502, as reported in Table 2 and FIG. 4.

It has also been discovered that there is limited homology between the amino acid sequences for the 2-5A-dependent RNases of the present invention and RNase E, encoded by the altered mRNA stability (ams)/rne gene of *E. coli*. Uniquely, the limited homology is generally conserved between the murine and human amino acid sequences for 2-5A-dependent RNases and generally lies between a 200 amino acid region. More particularly, for the human sequence, the amino acid region spans amino acid residues designated as 160–349 in Table 1 and FIGS. 9A and 9B. With respect to the murine sequence, the amino acid region spans amino acid residues designated as 160–348 in Table 2 and FIGS. 9A and 9B.

It has been further discovered and is believed that almost the entire, if not complete, amino acid sequences of the novel 2-5A-dependent RNase proteins of the instant invention are necessary for ribonuclease function. For example, it is believed that, when an about 84 amino acid region at the carboxy terminus is present in the human 2-5A-dependent RNase, the human 2-5A-dependent RNase has ribonuclease function in the presence of 2-5A. In contrast, when the murine 2-5A-dependent RNase lacks the about 84 amino acid region at the carboxy terminus, it lacks ribonuclease function.

With respect to the binding activity of a murine 2-5A-dependent RNase protein to 2-5A, it has been discovered that, when one P-loop is deleted from the repeated P-loop motif of a murine 2-5A-dependent RNase protein, nearly all 2-5A binding activity is lost, and that when both P-loops are deleted, virtually complete activity is lost. However, it has been found that, even though the carboxy terminus portion of the amino acid sequence of a murine 2-5A-dependent RNase protein following the repeated P-loop motif has been deleted, partial 2-5A binding activity is maintained.

It has been further discovered that when lysine residues 240 and 274 are replaced with asparagine residues in both P-loop motifs, significant 2-5A binding activity of a murine 2-5A-dependent RNase protein is lost. It has been further discovered, however, that when either lysine residue 240 or 274 is replaced in either P-loop motif, only partial 2-5A binding activity is lost. It is therefore believed that the presence of both P-loop motifs in the amino acid sequences for the 2-5A dependent RNases of the present invention plays an important role in 2-5A binding activity. It is further believed that the presence of lysine residues 240 and 274 in each P-loop motif plays an important role for enhanced 2-5A binding activity. It is also believed that the presence of virtually the entire amino acid sequence of the 2-5A-dependent RNases of the present invention provides for even further enhanced 2-5A binding activity, as well as provides for ribonuclease function.

In addition, the present invention relates to the cloning of murine and human 2-5A-dependent RNases and novel murine and human clones. Recombinant and naturally occurring forms of 2-5A-dependent RNase displayed virtually identical 2-5A binding properties and ribonuclease specificities.

The present invention further contemplates the use of the novel isolated, 2-5A-dependent RNases and encoding sequences therefor, as well as analogs and active fragments thereof, for use, for instance, 1.) in gene therapy for human and animal diseases including viral disease and cancer, 2.) as genetic markers for human disease due to perhaps cancer or viral infection, 3.) to develop plants and animals resistant to certain viruses, and 4.) as enzymes in connection with research and development, such as for studying the structure of RNA. In one manner to accomplish the above, and as contemplated by the present invention, the encoding sequences of the instant invention may be utilized in ex vivo therapy, i.e., to develop recombinant cells using the encoding sequence of the present invention using techniques known to those versed in this art. In another manner which may be employed to accomplish the above, the encoding sequences of the present invention may be combined with an appropriate promoter to form a recombinant molecule and inserted into a suitable vector for introduction into an animal, plant, or other lower life forms also using techniques known to those skilled in this art. Of course, other suitable methods or means known to those versed in this art may be selected to accomplish the above-stated objectives or other objectives for which the novel 2-5A-dependent RNases and encoding sequences of the present invention are suited.

The present invention also contemplates novel transgenic plants, as indicated above, which are resistant to viruses such as the picornaviruses. Generally speaking, the transgenic plants of the present invention include any inserted nucleotide sequence encoding any type of antiviral amino acid sequence, including proteins. Preferably, the antiviral nucleotide sequences introduced into plants in accordance with the present invention are animal antiviral genes, such as those genes which are stimulated in response to interferon production and/or treatment. These include, for example, those animal antiviral genes that encode 2-5A-synthetase, 2-5A-dependent RNase, and PKR. These interferon-regulated proteins, 2-5A-synthetase, 2-5A-dependent RNase and PKR (the dsRNA-dependent protein kinase) have recognized antiviral effects in higher animals and are believed to have antiviral effects in the transgenic plants of the present invention. PKR is stimulated by dsRNA to phosphorylate translation factor eIF2 which indirectly inhibits protein synthesis intiation. On the other hand, 2-5A synthetase is activated by dsRNA resulting in the production of "2-5A," $p_xA(2'p5'A)_y$ wherein X=about 1 to about 3 and Y≧about 2, from ATP. The 2-5A then activates an endoribonuclease entitled 2-5A dependent RNase (also known as RNase L or nuclease F). The activated ribonuclease degrades mRNA and rRNA thus inhibiting protein synthesis.

These above-described pathways are particularly effective at inhibiting viruses in animals with single stranded RNA genomes that replicate through dsRNA intermediates, such as the picornaviruses, and are believed to be effective at inhibiting similar types of viruses that infect plants. This belief is premised upon the understanding that most single stranded RNA plant viruses produce double stranded structures during replication by their viral replicases, see Dawson, W. O. et al.: *Acad. Press*, 38:307–342 (1990), and that plant viruses are similar to animal viruses in structure, composition and mechanism of replication in cells. In addition, even viral so-called single-stranded RNA may contain secondary structures which could activate PKR and 2-5A synthetase leading to widespread plant protection against plant viruses. It is believed that co-expression of 2-5A-dependent RNase and 2-5A-synthetase, will lead to the destruction of viral mRNA and viral genomic RNA thereby protecting the transgenic plants of the present invention from viruses. Moreover, it is believed that expression of PKR by the transgenic plants of the present invention will inhibit viral protein synthesis leading to inhibition of virus replication and protection of the transgenic plants. The present invention is therefore premised in part upon the belief that plant virus RNAs activate 2-5A-synthetase and PKR in the transgenic plants of the instant invention leading to immunity against virus infection. Furthermore, expression of 2-5A synthetase alone or 2-5A-dependent RNase alone or PKR alone may protect plants against viruses, perhaps by binding to viral RNA, such as viral replicative intermediates thereby blocking viral replication. Moreover, expression of only the dsRNA binding domains of PKR and/or of 2-5A-synthetase may similarly protect the transgenic plants of the present invention against viral infection.

It should therefore be appreciated by those versed in this art that novel transgenic plants which are resistant to viral infection can now be produced in accordance with the present invention. It is believed that the effectiveness of the anti-viral protection can be enhanced or even maximized when at least the three-above animal antiviral genes are inserted into plants to form exemplary transgenic plants of the present invention, since the animal antiviral proteins encoded by these three animal antiviral genes interfere with different stages of the viral life cycles. Moreover, these animal antiviral proteins or amino acid sequences are believed likely to be safe to give or introduce into animals, including humans, since these antiviral proteins or amino acid sequences are naturally occurring in humans as well as in other mammals, avians and reptiles.

While the present invention is described herein with reference to the particular sequences disclosed, it should nevertheless be understood by those skilled in this art that the present invention contemplates variations to the amino acid and/or nucleotide sequences which do not destroy 2-5A synthetase activity, PKR activity and/or 2-5A-dependent ribonuclease activity. Therefore, the present invention contemplates any analogs, parts or fragments of 2-5A-dependent RNase, 2-5A synthetase, and PKR which are active, such as any active part, and any encoding sequences therefor. In other words, the present invention includes, among other things, any amino acid sequence, any nucleotide sequence and any transgenic plant which have the ability to accomplish the objectives of the instant invention. For example, the instant invention includes any amino acid sequence which has antiviral activity and any nucleotide sequence which encodes therefor and those transgenic plants that express such nucleotide sequences. More specifically, the present invention includes, for instance: 1.) any animal amino acid sequence which has the ability to inhibit or interfere with viral replication such as those amino acid sequences that have activity similar or identical to PKR activity, 2-5A synthetase activity and/or 2-5A ribonuclease activity, and any nucleotide sequence which encodes for an amino acid sequence having any such activity; and 2.) any transgenic plant having any animal antiviral nucleotide sequence which encodes any such amino acid sequence which has any such antiviral activity.

The above features and advantages of the present invention will be better understood with reference to the accompanying FIGS., Detailed Description and Examples. It should also be understood that the particular methods, amino acid sequences, encoding sequences, constructs, vectors, recombinant cells, and antiviral transgenic plants illustrating the invention are exemplary only and not to be regarded as limitations of the invention.

BRIEF DESCRIPTION OF THE FIGS.

Reference is now made to the accompanying FIGS. in which is shown illustrative embodiments of the present invention from which its novel features and advantages will be apparent.

Figure 2A:
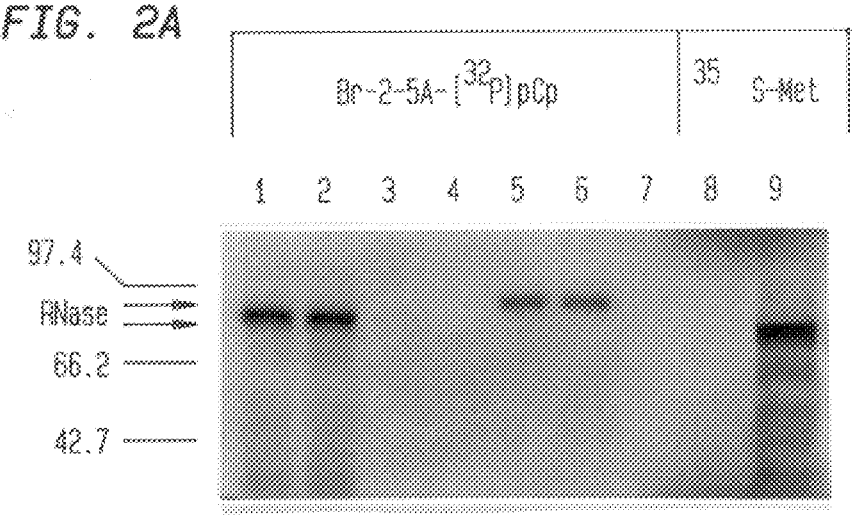
FIGS. 2A and 2B is a comparison of 2-5A binding activity of recombinant and naturally occurring forms of murine 2-5A-dependent RNase.

FIG. 2A is a specific affinity of truncated murine 2-5A-dependent RNase for 2-5A. UV covalent crosslinking of the $^{32}$P-2-5A probe (lanes 1–7) to protein is performed after translation reactions in wheat germ extract (5 $\mu$l) with murine 2-5A-dependent RNase mRNA (from clone ZB1) (lanes 1–3) or without added RNA (lane 4) or in extract of interferon treated mouse L cells (100 $\mu$g of protein) (lanes 5–7). Reactions are without added competitor (lanes 1, 4, and 5) or in the presence of either trimer core. (A2'p)$_2$A, (100 nM) (lanes 2 and 6) or trimer 2-5A, p$_3$(A2'p)$_2$A (100 nM) (lanes 3 and 7). Lanes 8 and 9 are produced by incubating the wheat germ extract with $^{35}$S-methionine in the absence or presence of 2-5A-dependent RNase mRNA, respectively.

Figure 2B:
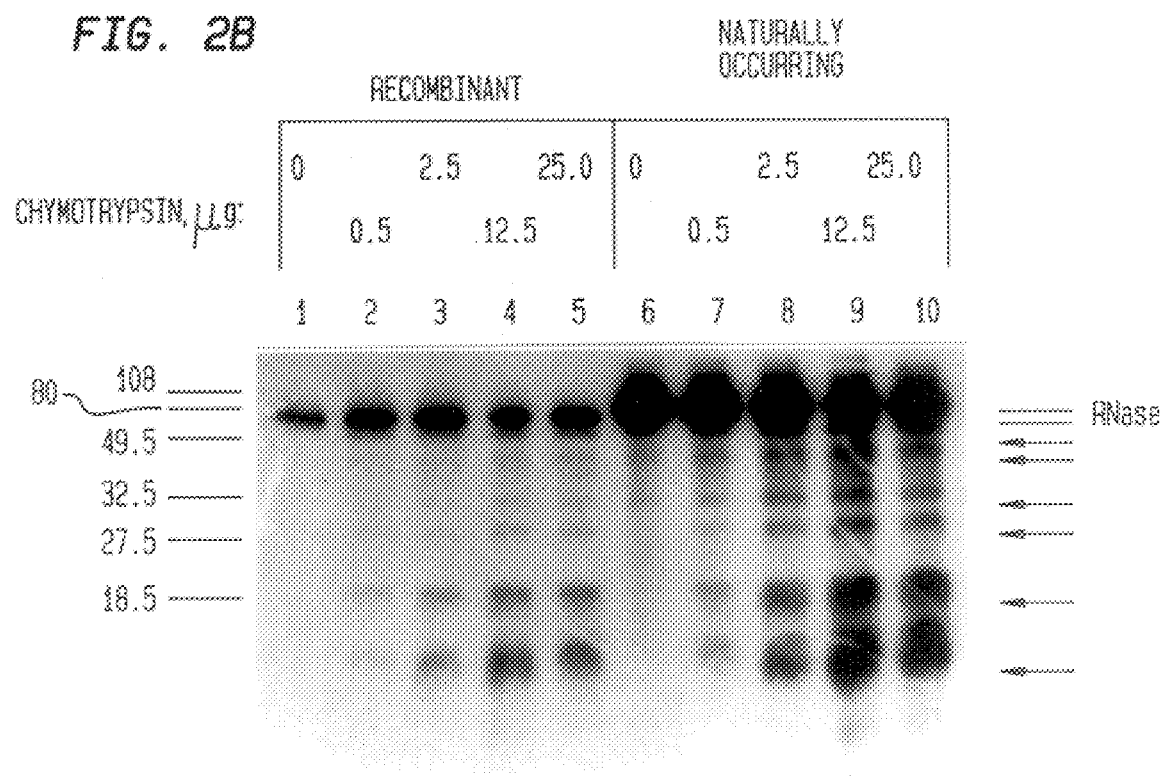

FIG. 2B are identical chymotrypsin cleavage products and are obtained from recombinant and naturally occurring form of 2-5A-dependent RNase. Partial chymotrypsin digests (arrows) are performed on truncated 2-5A-dependent RNase (clone ZB1) produced in wheat germ extract ("Recombinant") and murine L cell 2-5A-dependent RNase ("Naturally Occurring") after crosslinking to the 2-5A probe and purification from gels.

Figure 3A:
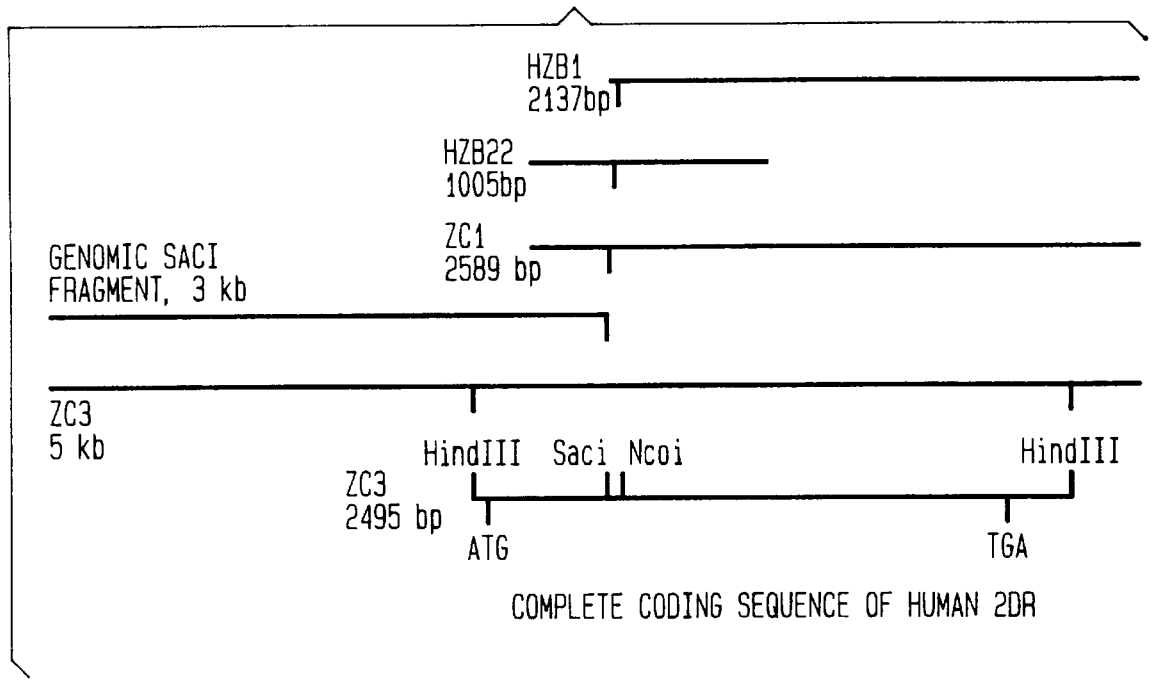
Figure 3B:
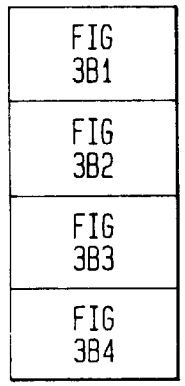

FIGS. 3A and 3B are clonings of the complete coding sequence for human 2-5A-dependent RNase.

FIG. 3A is the construction of a human 2-5A-dependent RNase clone. The initial human 2-5A-dependent RNase cDNA clone, HZB1, is isolated from an adult human kidney cDNA library in λgt10 using radiolabeled murine 2-5A-dependent RNase cDNA (clone ZB1) as probe. See Example. Radiolabeled HZB1 DNA is used to isolate a partially overlapping cDNA clone, HZB22, which is fused to HZB1 DNA at the NcoI site to form clone ZC1. The 5'-region of the coding sequence is obtained from a genomic SacI fragment isolated using a radiolabeled HZB22 DNA fragment as probe. Fusion of the genomic SACI fragment with ZC1 at the indicated SacI site produces clone ZC3. The coding sequence with some flanking sequences is then subcloned as a HindIII fragment into pBluescript KS(+) (Stratagene) resulting in clone ZC5. The restriction map for the composite clone, ZC5, is shown. Clone HZB1 includes nucleotides designated as 658–2223 in Table I which encode for amino acids designated as 220–741 in Table I. Clone HZB22 includes a nucleotide sequence which encodes for amino acids designated as 62–397 in Table I. Clone ZC1 includes a nucleotide sequence which encodes for amino acids designated as 62–741 in Table I. Clones ZC3 and ZC5 both include nucleotide sequences which encode for amino acids designated as 1–741 in Table I.

FIGS. 3B1, 3B2, 3B3 and 3B4 are the nucleotide sequence and predicted amino acid sequence of human 2-5A-dependent RNase with flanking nucleotide sequences. The numbers to the right on each of FIGS. 3B1–3B4 indicate the positions of nucleotides and amino acid residues.

Figure 1:
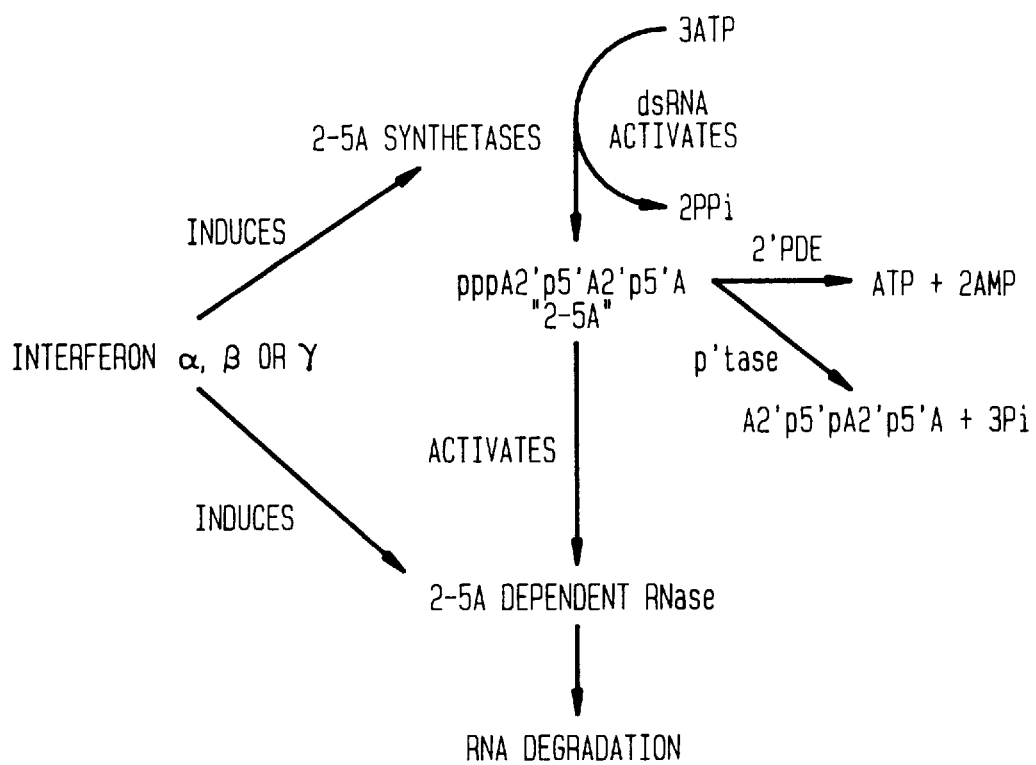
FIG. 1 is the 2-5A system: a ribonuclease pathway which is believed to function in the molecular mechanism of interferon action. 5'-phosphatase, p'tase; 2'-5'-phosphodiesterase, 2'-PDE.
Figure 4:
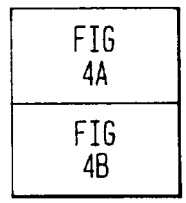

FIG. 3B shows the sequential order of FIGS. 3B1–3B4 for human 2-5A-dependent Rnase.

FIGS. 4A and 4B are the alignment of the predicted amino acid sequences for murine and human forms of 2-5A-dependent RNase. The positions of the repeated P-loop motifs, the cysteine (Cys)-rich regions with homology to zinc fingers, and the regions of homology to protein kinase domains VI and VII are indicated. Amino acids residues which are important components of the indicated domains are represented in bold type and are italicized. Identical amino acid residues in murine and human 2-5A-dependent RNase are indicated with colon (:) symbols adjacent therebetween.

FIG. 4 shows the sequential order of FIGS. 4A and 4B for murine and human forms of 2-5A-dependent RNase.

Figure 5A:
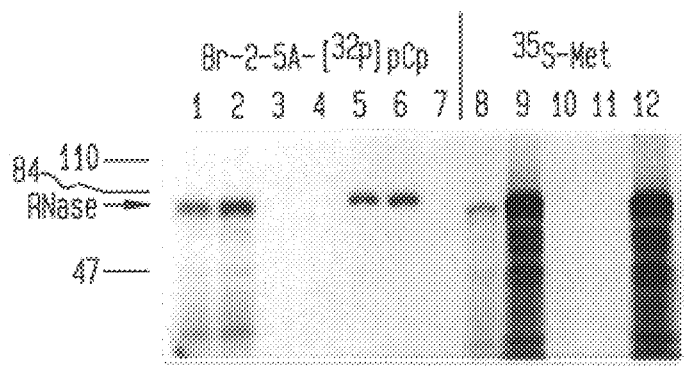
Figure 5B:
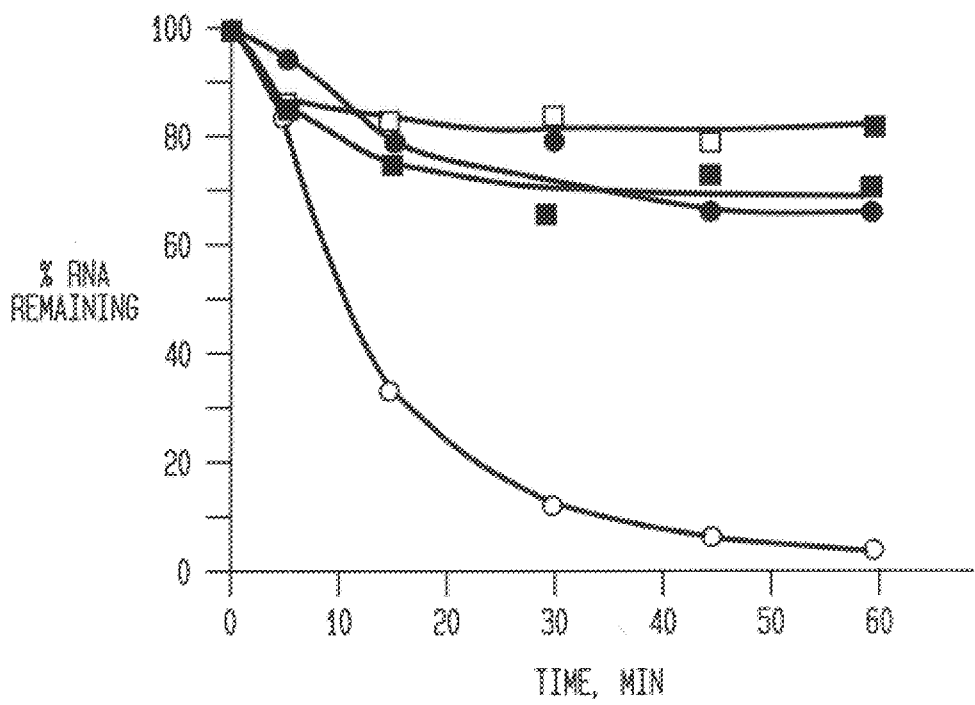

FIGS. 5A and 5B are 2-5A binding properties and ribonuclease activity of recombinant human 2-5A-dependent RNase produced in vitro.

FIG. 5A is specific affinity of recombinant human 2-5A-dependent RNase for 2-5A. Crosslinking of the 2-5A probe (lanes 1–7) to protein is performed after translation reactions in wheat germ extract (5 $\mu$l) with human 2-5A-dependent RNase mRNA (lanes 1–3) or without added RNA (lane 4) or in extract of human interferon $\alpha$ treated (1000 units per ml for 16 h) human HeLa cells (350 $\mu$g of protein) (lanes 5–7). Reactions were without added competitor (lanes 1, 4, and 5) or in the presence of either trimer core, $(A2'p)_2A$, (100 nM) (lanes 2 and 6) or trimer 2-5A, $p_3(A2'p)_2A$ (100 nM) (lanes 3 and 7). Incubations with $^{35}$S-methionine are shown in lanes 8 to 12. Lane 8 is with wheat germ extract and human 2-5A-dependent RNase mRNA. Reticulocyte lysate preadsorbed to 2-5A-cellulose is incubated with human 2-5A-dependent RNase mRNA in the absence (lane 9) or presence (lane 10) of cycloheximide, or in the absence of added mRNA (lane 11). Lane 12 shows human 2-5A-dependent RNase which is produced in the nonadsorbed, crude reticulocyte lysate. The positions and relative molecular masses (in kDa) of the marker proteins are indicated.

FIG. 5B is reticulocyte lysate pretreated to remove endogeous 2-5A-dependent RNase and is incubated in the absence of added mRNA (■), in the presence of human 2-5A-dependent RNase mRNA without inhibitor (○, □) or in the presence of both 2-5A-dependent RNase mRNA and cycloheximide (50 $\mu$g per ml (●). See Example I. Subsequently, the recombinant 2-5A-dependent RNase (or controls) is adsorbed to 2-5A-cellulose and ribonuclease assays are performed after extensive washing of the matrix to reduce general nuclease activity. Radiolabeled substrate RNA was either poly(U) (○, ●, ■) or poly(C) (□).

Figure 6A:
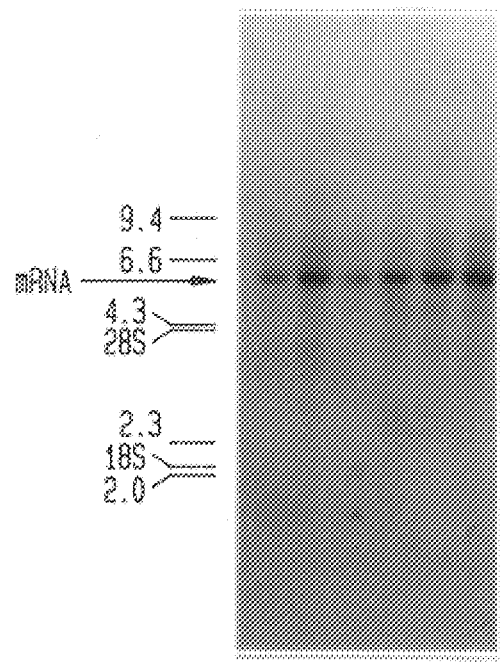
Figure 6B:
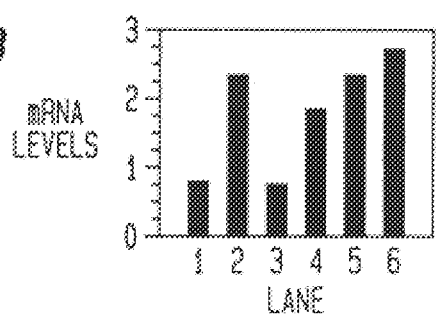
Figure 6C:
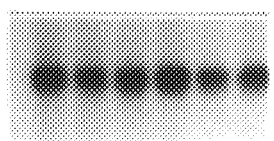

FIGS. 6A, 6B and 6C show levels of 2-5A-dependent RNase mRNA which are induced by interferon treatment of murine L929 cells even in the presence of cycloheximide.

FIG. 6A is a northern blot prepared with poly(A)⁺RNA (4 $\mu$g per lane) that is isolated from murine L929 cells treated with murine interferon ($\alpha+\beta$) (1000 units per ml) and/or cycloheximide (50 $\mu$g per ml) for different durations (indicated) which is probed with radiolabeled murine 2-5A-dependent RNase cDNA. Interferon, IFN; cycloheximide, CHI.

FIG. 6B shows levels of 2-5A-dependent RNase which are estimated from the autoradiogram shown in panel (a) with a video camera and QuickCapture and Image computer programs.

FIG. 6C shows levels of glyceraldehyde-3-phosphate dehydrogenase (GAPDH) mRNA as determined in the same blot shown in panel (A).

Figure 7A:
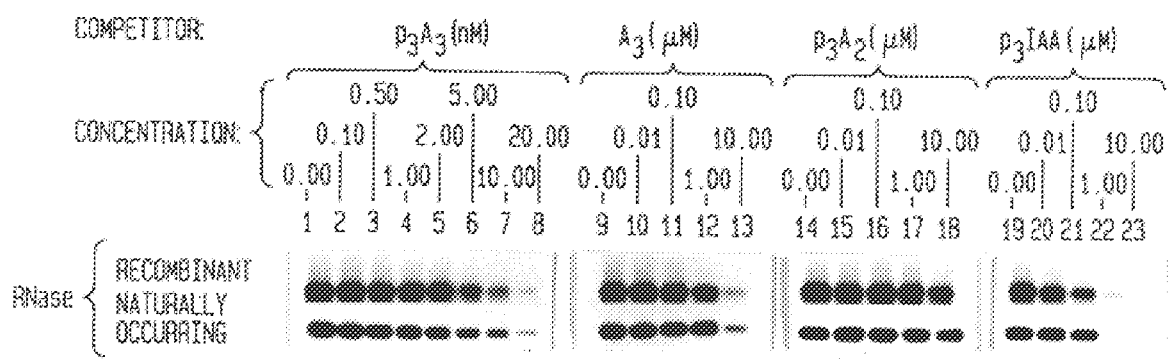
Figure 7B:
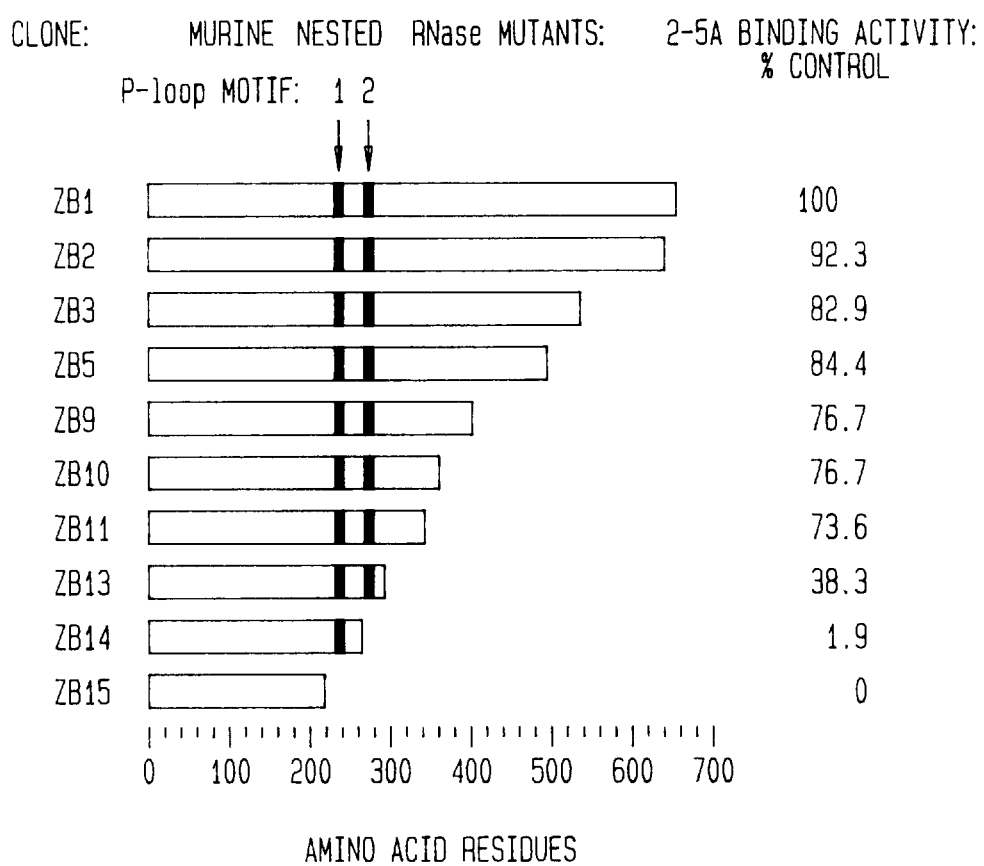

FIGS. 7A and 7B are the truncated, recombinant murine 2-5A-dependent RNase, clone ZB1, and murine L cell 2-5A-dependent RNase having identical 2-5A binding activities localized to a repeated P-loop motif.

FIG. 7A shows incubations of truncated 2-5A-dependent RNase, clone ZB1, ("Recombinant") which is produced in wheat germ extract (upper panel) or of murine L cell 2-5A-dependent RNase (labeled "Naturally Occurring," lower panel) with the $^{32}$P-2-5A probe, (2.4 nM), are in the absence of presence of unlabeled 2',5'-phosphodiester linked oligonucleotides (as indicated) followed by uv covalent crosslinking. Autoradiograms of the dried SDS/10% polyacrylamide gels are shown. Concentrations of the oligonucleotide competitors are indicated. I is inosine.

FIG. 7B shows a truncated series of murine 2-5A-dependent RNase mutants (ZB1 to ZB15) which is produced in wheat germ extract which are assayed for 2-5A binding activity by a filter binding method. See Example and Knight et al. 1980). The positions of the P-loop motifs and the lengths of the translation products are indicated. Clone ZB1 encodes for amino acids designated as 1–656 in Table 2, except for the last 5 amino acid residues which are Lys, Pro, Leu, Ser, and Gly. Clone ZB2 encodes for amino acids designated as 1–619 in Table 2. Clone ZB3 encodes for amino acids designated as 1–515 in Table 2. Clone ZB5 encodes for amino acids designated as 1–474 in Table 2. Clone ZB9 encodes for amino acids designated as 1–403 in Table 2. Clone ZB10 encodes for amino acids designated as 1–365 in Table 2. Clone ZB13 encodes for amino acids designated as 1–294 in Table 2. Clone ZB14 encodes for amino acids designated as 1–265 in Table 2. Clone ZB15 encodes for amino acids designated as 1–218 in Table 2.

Figure 8A:
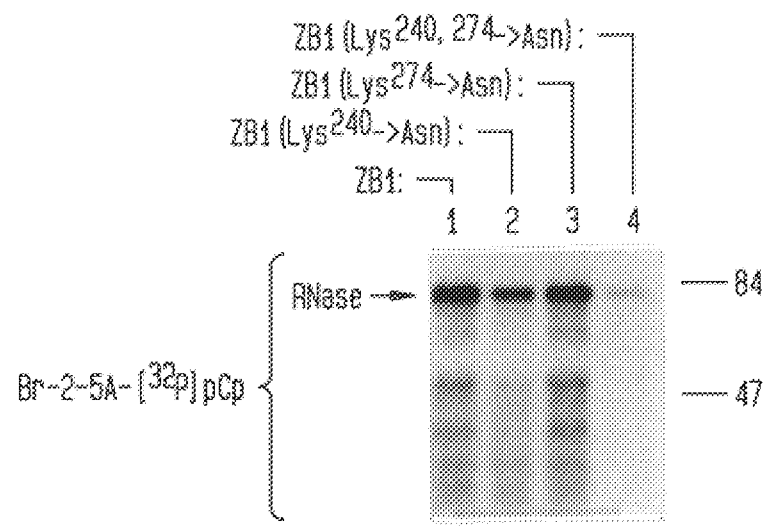
Figure 8B:
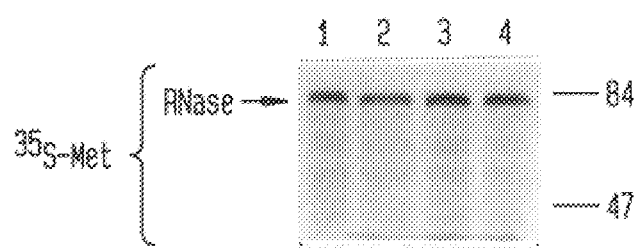

FIGS. 8A and 8B are substitution mutations of the lysine residues in the P-loop motifs of 2-5A-dependent RNase.

FIG. 8A shows the truncated murine 2-5A-dependent RNase, clone ZB1, and lysine to asparagine substitution mutants of clone ZB1, which are synthesized in wheat germ extract. In (A) unlabeled translation products are covalently crosslinked to the bromine-substituted, $^{32}$P-labeled 2-5A probe, Br-2-5A-[$^{32}$P]pCp. See Nolan-Sorden et al., 1990.

FIG. 8B shows the mRNA species which are translated in the presence of $^{35}$-S-methionine in separate reactions. Autoradiograms of the dried, SDS/polyacrylamide gels are shown. The order and positions of the translation products (labelled "RNase") and the relative molecular masses (in kDa) of the protein markers are indicated.

Figures 9A, 9B:
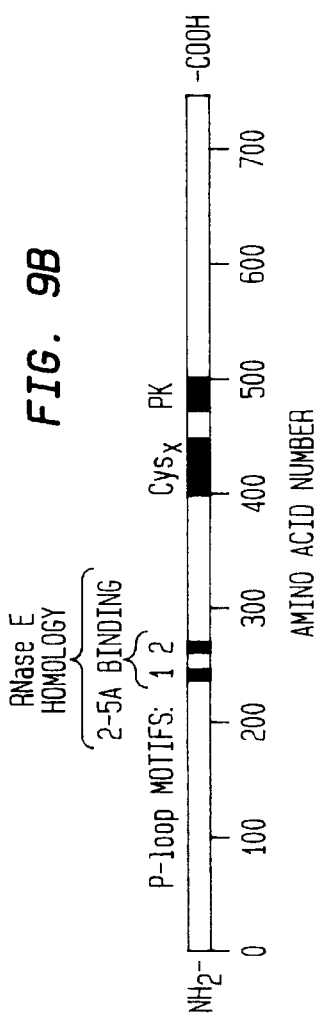

FIGS. 9A and 9B are a comparison of the amino acid sequences of RNase E and 2-5A-dependent RNase.

FIG. 9A shows identical and conservative matches which are shown between E. coli RNase E and the murine and human forms of 2DR.

FIG. 9B is a model for the structure and function of 2DR. Abbreviations: P-loop motifs, a repeated sequence with homology to P-loops; Cys$_x$, a cysteine-rich region with homology to certain zinc fingers; PK, homology to protein kinase domains VI and VII.

FIGS. 10A and 10B are a comparison of the amino acid sequences of the ankyrin repeats in the human and murine 2-5A-dependent RNase proteins.

FIG. 10A shows murine and human forms of 2-5A-dependent RNases containing four ankyrin repeats. Homology between the ankyrin consensus sequence and the murine and human forms of 2-5A-dependent RNase are indicated. ψ, hydrophobic amino acids.

FIG. 10B is a model showing the relative positions of the four ankyrin repeats in 2-5A-dependent RNase in comparison to the position of the proposed 2-5A binding domain (↑) (the repeated P-loop motif); $Cys_x$, the cysteine-rich region; PK, the protein kinase homology region, and the carboxy-terminal region required for RNase activity.

Figure 11:
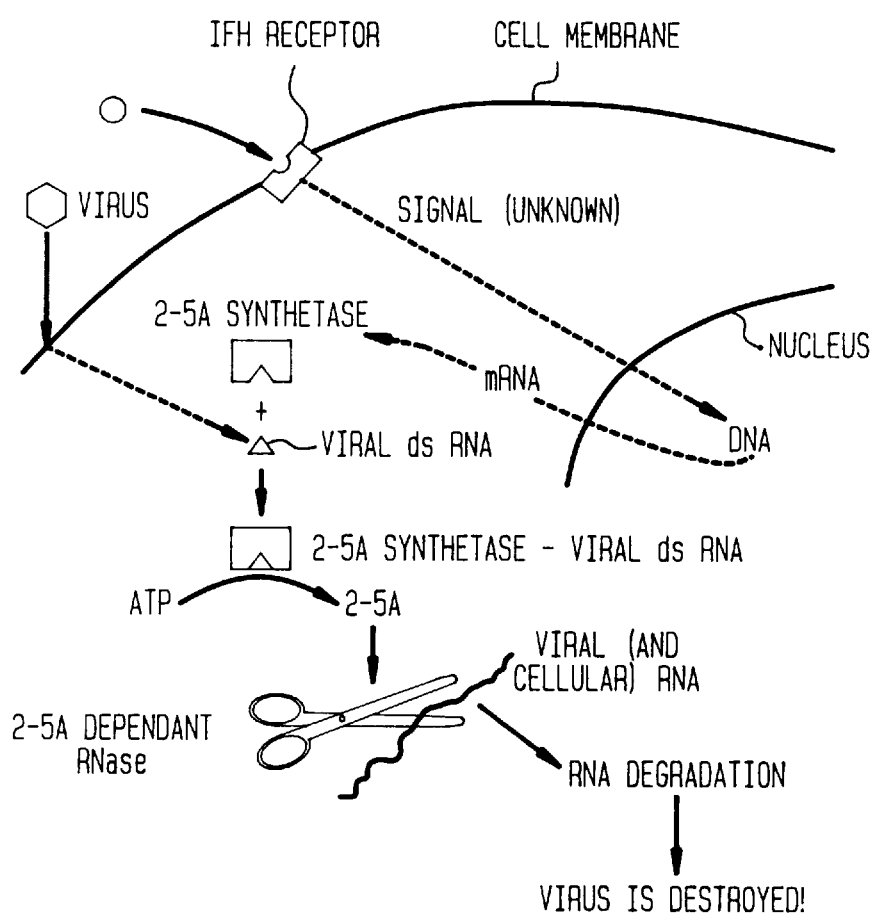

FIG. 11 shows the role of 2-5A-dependent RNase in the anti-viral response of cells to interferon treatment. Interferon binds to specific cell surface receptors resulting in the generation of a signal which activates a set of genes in the cell nucleus. The genes for 2-5A synthetase are thus activated producing inactive, native 2-5A synthetase. Interferon treatment of the cell also activates the 2-5A-dependent RNase gene (not shown in the FIGure). Subsequently, the interferon-treated cells is infected by a virus. The virus produces double stranded RNA (dsRNA) during its replicative cycle. The viral dsRNA then activates the 2-5A synthetase resulting in the production of 2-5A. The 2-5A then activates the 2-5A-dependent RNase to degrade the viral RNA thus destroying the virus itself.

Figure 12:
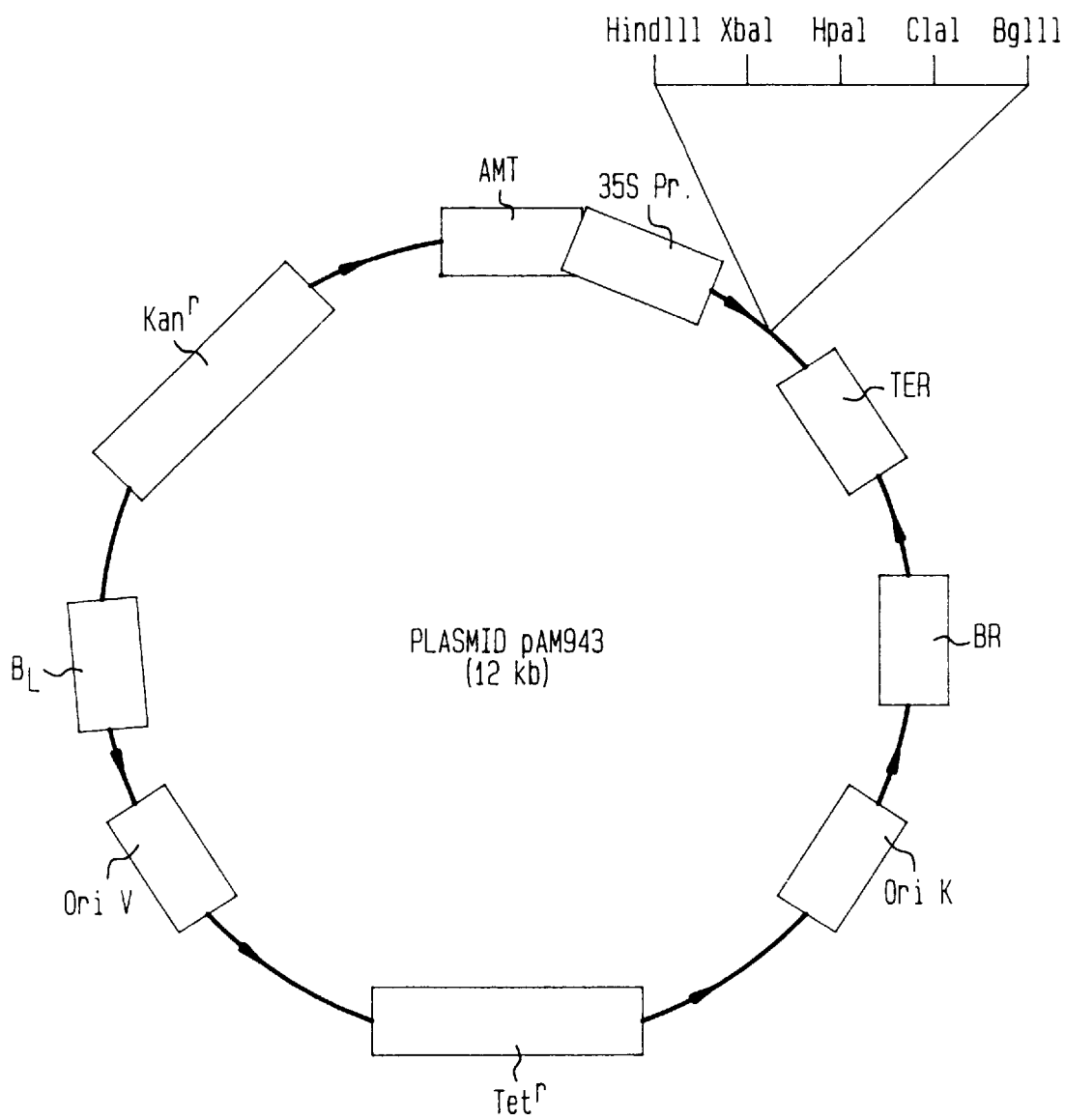

FIG. 12 depicts a physical map of T: based binary vector pAM943 which is about 12 Kbp. Abbreviations: $B_L$, left border; $B_R$, right border; $Kan^r$, kanamycin resistance; AMT, promoter of adenyl methyl transferase gene from Chlorella virus; 35S, promoter for 35S RNA from Cauliflower mosaic virus; TER, RNA termination signal; Ovi V and Ori K origins of DNA replication.

Figure 13:
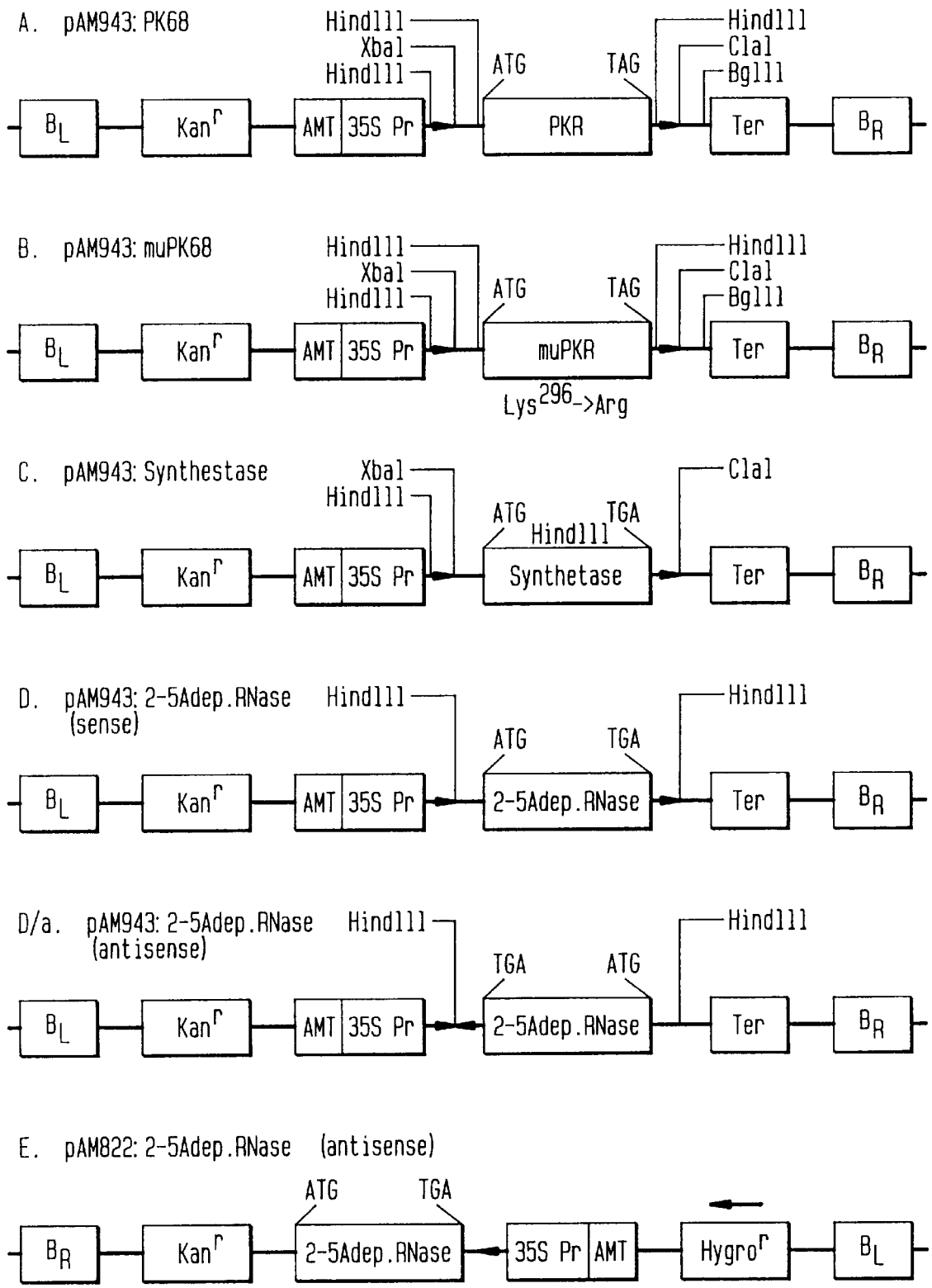

FIG. 13 depicts physical maps of portions of certain recombinant plasmid constructs containing cDNAs encoding mammalian antiviral proteins and showing the important DNA elements in between right border and left border of T-DNAs that are transferred to plant genomes. FIG. 13A depicts a certain portion of plasmid pAM943:PK68; FIG. 13B depicts a certain portion of plasmid pAM943:muPK68; FIG. 13C depicts a certain portion of plasmid pAM943:Synthetase; FIG. 13D depicts a certain portion of plasmid pAM943:2-5A-dep. RNase (sense); FIG. 13D/a depicts a certain portion of plasmid pAM943:2-5A-dep. RNase and FIG. 13E depicts pAM822:2-5A dep. RNase (antisense). Abbreviations: $B_L$, left border; $B_R$, right border; $Kan^r$, kanamycin resistance; $Hygro^r$, hygromycin resistance; AMT, promoter of adenyl methyl transferase gene from Chlorella virus; 35S, promoter for 35S RNA from Cauliflower mosaic virus; PKR, cDNA to human PKR; muPKR, cDNA to a lysine (amino acid #296) to arginine mutant form of PKR; Synthetase, cDNA to a low molecular weight form of human 2-5A-synthetase; 2-5Adep. RNase, cDNA to human 2-5A-dependent RNase; TER, RNA termination signal.

Figure 14:
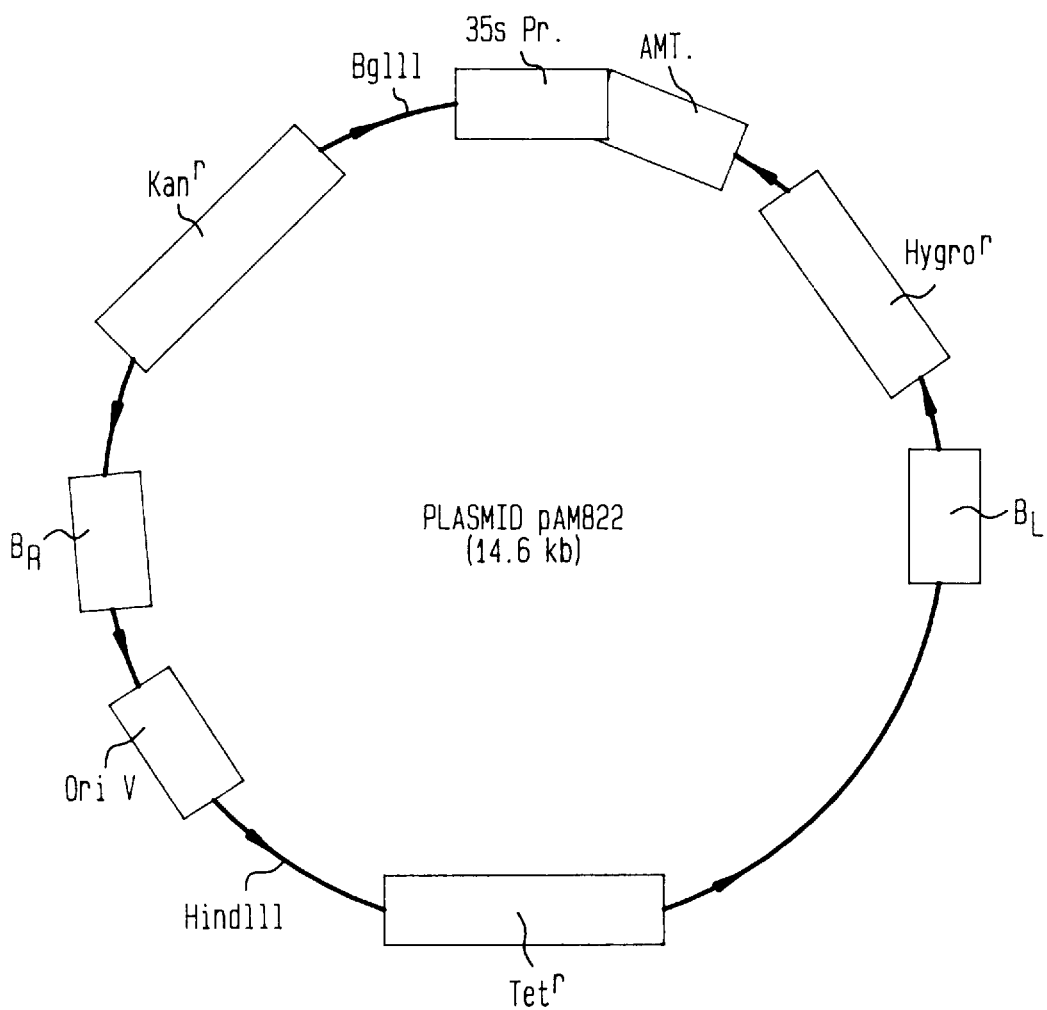

FIG. 14 shows a physical map of Ti based binary vector pAM822 which is about 14.6 Kbp. Abbreviations: $B_L$, left border; $B_R$, right border; $Kan^r$, kanamycin resistance; $Hygro^r$, hygromycin resistance; $Tet^r$, tetracycline resistance; AMT, promoter of adenyl methyl transferase gene from Chlorella virus; 35S, promoter for 35S RNA from Cauliflower mosaic virus; TER, RNA termination signal; Ovi V, origin of DNA replication.

Figure 15:
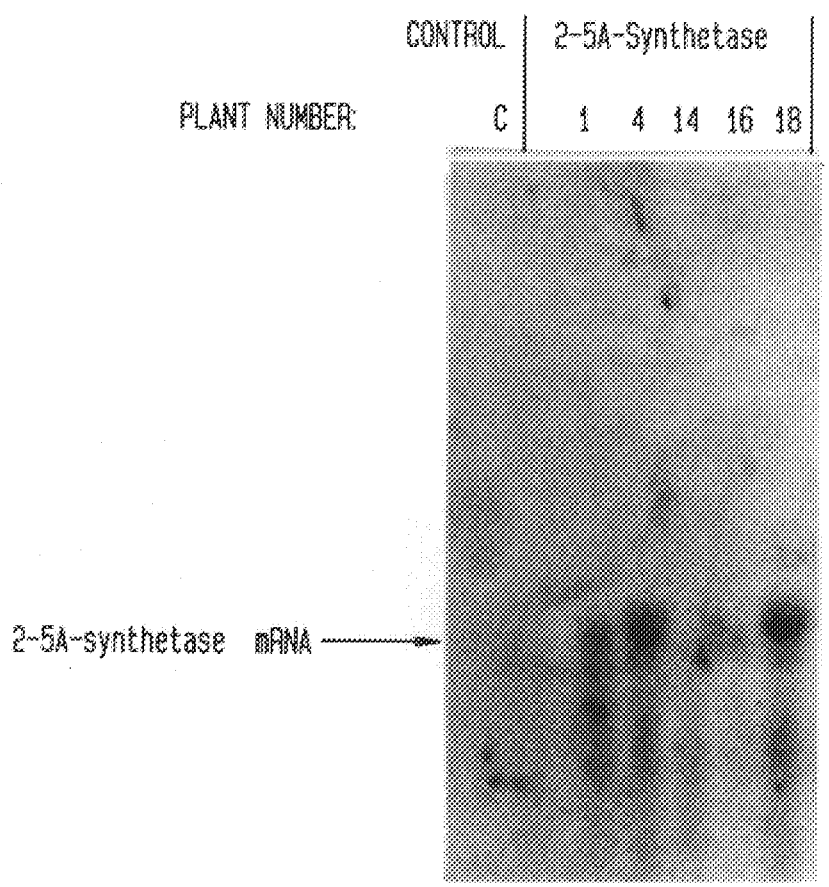

FIG. 15 shows expression of human 2-5A-synthetase cDNA intransgenic tobacco plants as determined by measuring mRNA levels in a Northern blot. Construct C (pAM943:Synthetase) was introduced into the plants. Total RNA was prepared from the leaves of control (labeled "C") and transgenic plants using RNASTAT-60 (Tel-Test B., Inc.). Thirty μg of RNA was treated with glyoxal and separated in a 1.5% agarose gel. After electrophoresis RNA was transferred to Magnagraph (MSI) Nylon membrane and probed with human 2-5A-synthetase cDNA labeled with [α-$^{32}$P]dCTP by random priming. Autoradiograms were made from the dried blots.

Figure 16:
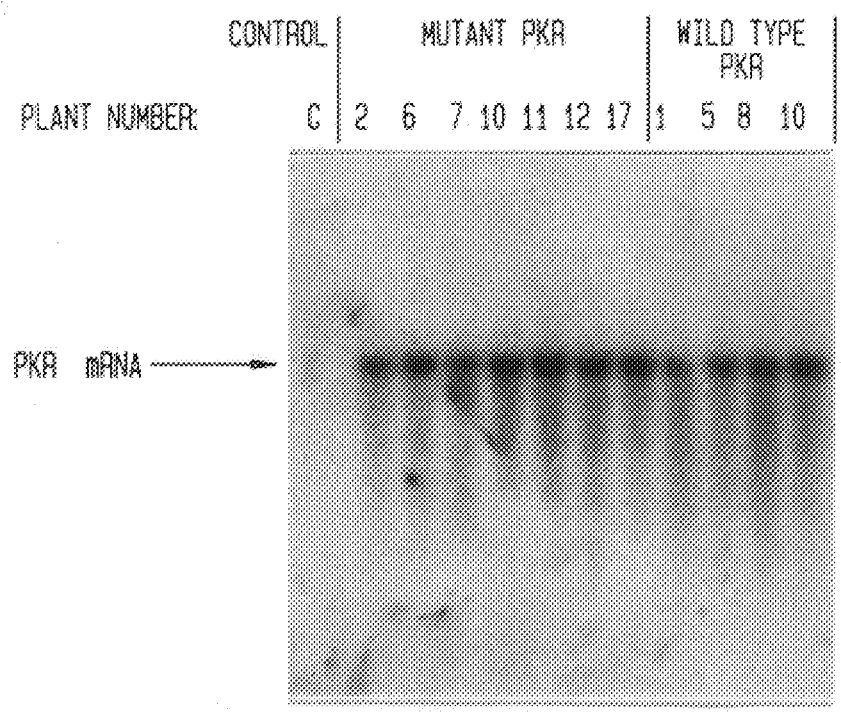

FIG. 16 shows expression of mutant and wild type forms of human PKR cDNA in transgenic tobacco plants as determined by measuring mRNA levels in a Northern blot. Constructs A (pAM943:PK68) and B (pAM943:muPK68) encoding wild type and mutant (lysine at position 296 to arginine) forms of PKR, respectively, were introduced into the plants. Total RNA was prepared from the leaves of control (labeled "C") and transgenic plants using RNASTAT-60 (Tel-Test B., Inc.). Thirty μg of RNA was treated with glyoxal and separated in a 1.5% agarose gel. After electrophoresis RNA was transferred to Magnagraph (MSI) Nylon membrane and probed with human PKR cDNA labeled with [α-$^{32}$P]dCTP by random priming. Autoradiograms were made from the dried blots.

Figure 17:
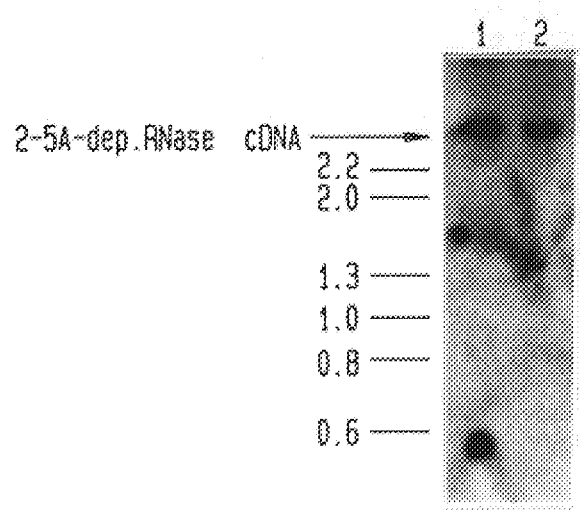

FIG. 17 shows a presence of 2-5A-dependent RNase cDNA in transgenic plants as determined on a Southern blot. Genomic DNA was isolated from leaves of transgenic plants containing construct D/a (pAM943:2-5A-dep.RNase, antisense) using CTAB (cetyltrimethylammonium bromide) following the method of Rogers and Bendich (1988, Plant Molecular Biology Manual, A6, pp. 1–10, Kluwar Academic Pulbisher, Dordrecht). Ten μg of genomic DNA was digested with HindIII for 5 h at 37° C. and fractionated in a 1% agarose gel followed by transfer to Magnagraph (nylon transfer membrane, Micron Separations, Inc.) using a capillary transfer method. The cDNA for 2-5A-dependent RNase (from plasmid pZC5) was labeled by random priming with [α-$^{32}$P]dCTP (3,000 Ci/mmole) using a Prime-a-gene kit from (Promega) according to the protocol supplied by the company. The labeled 2-5A-dependent RNase cDNA (Specific activity of 1.0×10$^9$ c.p.m. per μg DNA) was washed and an autoradiogram was made from the dried membrane. The sizes (in kilobases) and the positions of the DNA markers are indicated. The band indicated as "2-5A-dep. RNase cDNA" (see arrow) was absent in Southern blots of control plants (data not shown).

FIG. 18 depicts a coding sequence for human p68 kinase mRNA (PKR) cDNA.

FIG. 19 depicts a translation product of the complete coding sequence for human p68 kinase mRNA (PKR) of FIG. 18.

FIG. 20 depicts a coding sequence for human 2-5A synthetase cDNA.

FIG. 21 depicts a translation product of the coding sequence for human 2-5A-synthetase of FIG. 20.

DETAILED DESCRIPTION

By way of illustrating and providing a more complete appreciation of the present invention and many of the attendant advantages thereof, the following Detailed Description and Examples are given concerning the novel 2-5A-dependent RNases, encoding sequences therefor, recombinant nucleotide molecules, constructs, vectors, recombinant cells, antiviral transgenic plants and methods.

Because 2-5A-dependent RNase is very low in abundance (one five-hundred-thousandth of the total protein in mouse liver, Silverman, R. H. et al., *J. Biol. Chem.*, 263:7336–7341 (1988)), its cloning requires the development of a sensitive screening method. Murine L929 cells are selected as the source of mRNA due to high basal levels of 2-5A-dependent RNase. A protocol to enhance 2-5A-dependent RNase mRNA levels is developed based on the observation that optimal induction of 2-5A-dependent RNase is obtained by treating cells with both interferon and cycloheximide, then with medium alone. See Example. The cDNA library is screened by an adaptation of techniques developed for cloning DNA binding proteins, Singh, H. et al., *Cell*, 52:415–423 (1988); Singh H. et al., *BioTechniques*, 7:252–261 (1989), in which a bromine-substituted $^{32}$P-labeled 2-5A analogue ("2-5A probe"), Example and Nolan-Sorden, N. L. et al., *Anal. Biochem.*, 184:298–304 (1990), replaced a radiolabeled oligodeoxyribonucleotide. A single clone (ZB1) is thus isolated from about three million plaques. The protein expressed from the ZB1 clone, transferred from plaques to filter-lifts, shows reactivity to both the 2-5A probe and to a highly purified polyclonal antibody directed against 2-5A-dependent RNase.

To obtain recombinant protein for characterization, the cDNA is transcribed and translated in cell-free systems. See Example. 2-5A binding activity is then determined by covalently crosslinking the 2-5A probe to the protein with uv light, for example, Nolan-Sorden, N. L. et al., *Anal. Biochem.*, 184:298–304 (1990). The recombinant 74 kDa protein produced in a wheat germ extract shows specific affinity for the 2-5A probe. See FIG. 2A, lanes 1 to 3. A core derivative of 2-5A lacking 5'-phosphoryl groups, (A2'p)$_2$A, fails to interfere with binding of the protein to the 2-5A probe whereas trimer 205A, p$_3$(A2'p)$_2$A, completely prevents probe binding. See FIG. 2A, lanes 2 and 3, respectively. There is no detectable 2-5A binding proteins in the wheat germ extract as shown in the incubation without added RNA, FIG. 2A, lane 4. For comparison, a similar profile of 2-5A binding activity is obtained for the 80 kDa 2-5A-dependent RNase from murine L929 cells, incubated without added oligonucleotide or with (A2'p)$_2$A or p$_3$(A2'p)$_2$A as competitors. See FIG. 2A, lanes 5 to 7. The $^{35}$S-labeled translation product is shown in FIG. 2A, lane 9. In a further comparison, covalent linkage of the 2-5A probe to the about 74 kDa protein and to murine L929 cell 2-5A-dependent RNase followed by partial digestion with chymotrypsin produces an identical pattern of six labeled peptides. See FIG. 2B. Similarly, partial digestion of the two labeled proteins with *S. aureus* V8 protease also produces identical patterns of labeled cleavage products. These results and the apparent molecular weight of about 74 kDa for the recombinant protein, as compared to about 80 kDa for 2-5A-dependent RNase, see FIG. 2A, suggests that the about 74 kDa protein is a truncated, or partial clone for 2-5A-dependent RNase.

To obtain the entire coding sequence for human 2-5A-dependent RNase, a composite DNA containing genomic and cDNA is constructed. See FIG. 3A. The initial cDNA portion of the human 2-5A-dependent RNase clone (HZB1) is obtained by screening a human kidney cDNA library with radiolabeled murine 2-5A-dependent RNase cDNA. See Example. A genomic clone, containing the 5'-part of the coding sequence, is isolated with radiolabeled human 2-5A-dependent RNase cDNA. The nucleotide and predicted amino acid sequences of human 2-5A-dependent RNase are determined, FIG. 3B, resulting an open reading frame encoding a protein of 83,539 Da.

A comparison is made between the predicted amino acid sequences of the human and murine forms of 2-5A-dependent RNase in order to identify and evaluate the conserved regions of the proteins. See FIG. 4. The murine cDNA, clone ZB1, contains about 88% of the coding sequence for 2-5A-dependent RNase to which an additional twenty-eight 3'-codons are added from a murine genomic clone. Alignment of the murine and human forms of 2-5A-dependent RNase indicates about 65% identity between the overlapping regions. See FIG. 4. In addition, there is 73% identity between the corresponding nucleotide sequences for murine and human 2-5A-dependent RNase. The apparent translation start codons for both the murine and human 2-5A-dependent RNases, are in an appropriate context for translational initiation, namely ACCATGG and GTCATGG, respectively. See FIG. 3B. See also, for example, Kozak, M., *Cell*, 44:283–292 (1986). In addition, both the human and murine 2-5A-dependent RNase sequences contain in-frame stop codons upstream of the translation start sites. See FIG. 3B.

The 2-5A binding properties of the recombinant and naturally occurring forms of human 2-5A-dependent RNase are compared by uv covalent crosslinking to the 2-5A probe. The recombinant human 2-5A-dependent RNase produces in wheat germ extract shows specific affinity for 2-5A. See FIG. 5A, lanes 1 to 3. Radiolabeling of the cloned human 2-5A-dependent RNase with the 2-5A probe is not prevented by (A2'p)$_2$A. See FIG. 5A, lanes 1 and 2. In contrast, addition of trimer 2-5A, p$_3$(A2'p)$_2$A, effectively competes with the 2-5A probe for binding to the recombinant 2-5A-dependent RNase. See lane 3. The same pattern of 2-5A binding activity is obtained with 2-5A-dependent RNase in an extract of interferon-treated human HeLa cells. See FIG. 5A, lanes 5 to 7. The apparent molecular weights of HeLa cell 2-5A-dependent RNase and $^{35}$S-labeled recombinant human 2-5A-dependent RNase produced in reticulocyte lysate are believed to be exactly the same (about 80 kDa). See FIG. 5A, lanes 5 and 9. The recombinant human 2-5A-dependent RNase produced in wheat germ extract migrates slightly faster probably due to post-translational modifications. See FIG. 5A, lanes 1, 2 and 8.

To demonstrate and characterize the ribonuclease activity of the cloned 2-5A-dependent RNase, translation is performed in a reticulocyte lysate instead of a wheat germ extract due to the substantially greater efficiency of protein synthesis in the former system. See FIG. 5A, compare lanes 9 and 8. Prior to translation, endogenous reticulocyte 2-5A-dependent RNase is removed by adsorbing the lysate to the affinity matrix, 2-5A-cellulose. See Example. See also, Silverman, R. H., *Anal. Biochem.*, 144:450–460 (1985). The treatment with 2-5A-cellulose effectively removes all measurable endogenous 2-5A-dependent RNase activity from the lysate, as determined by 2-5A-dependent ribonuclease assays, and FIG. 5B. In addition, the adsorption-depletion protocol did not reduce translational efficiency. FIG. 5A, lanes 9 and 12 show the $^{35}$S-translation products produced in the 2-5A-cellulose-pretreated and untreated lysates, respectively.

Ribonuclease assays with recombinant 2-5A-dependent RNase are performed after immobilizing and purifying the translation product on the activating affinity matrix, 2-5A-cellulose. It was previously shown that murine L cell 2-5A-dependent RNase bound to 2-5A-cellulose, resulting in ribonuclease activity against poly(U) but not poly(C). See Silverman, R. H., *Anal. Biochem.*, 144:450–460 (1985). Furthermore, by washing 2-5A-dependent RNase:2-5A-cellulose prior to adding the substrate the level of general, non-2-5A-dependent RNase, is greatly reduced. See Silverman, R. H., *Anal. Biochem.*, 144:450–460 (1985). Incubations of lysate in the absence of added mRNA or in the presence of both human 2-5A-dependent RNase mRNA and cycloheximide resulted in only low levels of poly(U) breakdown. See FIG. 5B. In addition, it is shown that cycloheximide completely prevented 2-5A-dependent RNase synthesis. See FIG. 5A, lane 10. In contrast, translation of the human 2-5A-dependent RNase mRNA, in the absence of inhibitor, results in substantial ribonuclease activity against poly(U) but not against poly(C). See FIG. 5B. The poly(U) is degraded with a half-life of about 10 minutes whereas only 20% of the poly(C) is degraded after one hour of incubation. Binding of recombinant 2-5A-dependent RNase to the affinity matrix was also shown by monitoring the presence of the $^{35}$S-labeled translation product. These results are believed to demonstrate that the recombinant human 2-5A-dependent RNase produced in vitro is a functional and potent ribonuclease. Furthermore, both recombinant and naturally occurring forms of 2-5A-dependent RNase are capable of cleaving poly(U) but not poly(C). See FIG. 5B. See also Silverman, R. H., *Anal. Biochem.*, 144:450–460 (1985) and Floyd-Smith, G. et al., *Science*, 212:1020–1032 (1981).

To determine if 2-5A-dependent RNase mRNA levels are regulated by interferon, a northern blot from murine L929 cells treated with interferon and cycloheximide is probed with the radiolabeled murine 2-5A-dependent RNase cDNA. See FIG. 6. 2-5A-dependent RNase mRNA levels are enhanced three-fold by interferon ($\alpha$+$\beta$) treatment even in the presence of cycloheximide. See FIGS. 6A and B, compare lanes 1 and 2). Regulation of 2-5A-dependent RNase mRNA levels by interferon as a function of time is demonstrated (FIGS. 6A and B, lanes 3 to 6). Maximum 2-5A-dependent RNase mRNA levels are observed after 14 hours of interferon treatment. See FIGS. 6A and B, lane 6. A similar increase in levels of 2-5A-dependent RNase per se is observed after interferon treatment of the cells. Relatively invariant levels of GAPDH mRNA indicates that equivalent levels of RNA are present in every lane of the blot. See FIG. 6C. These results are believed to show that the induction of 2-5A-dependent RNase expression is a primary response to interferon treatment. The murine and human 2-5A-dependent RNase mRNAs are determined from northern blots to be 5.7 kb and 5.0 kb in length, respectively. See FIG. 6A. The 2-5A-dependent RNase coding sequences, therefore, comprise only about 40% the nucleotide sequences contained in the mRNAs.

The 2-5A binding functions of the recombinant and naturally occurring forms of murine 2-5A-dependent RNase are characterized by covalent crosslinking to the 2-5A probe in the presence of unlabeled 2-5A or 2-5A analogues as competitors. See FIG. 7A. Interestingly, although the about 74 kDa truncated 2-5A-dependent RNase is missing about 84 amino acids from its carboxy-terminus, see FIG. 4, it nonetheless possesses a 2-5A binding activity indistinguishable from that of naturally occurring 2-5A-dependent RNase. See FIG. 7A. Trimer 2-5A[p$_3$(A2'p)$_2$A], at about 20 nM effectively prevents the 2-5A probe from binding to either protein. See FIG. 7A, lane 8. In comparison, a 500-fold higher concentration of (A2'p)$_2$A (10 $\mu$M) is required to prevent probe binding to both proteins. See lane 13. The dimer species, p$_3$A2'pA, is unable to prevent the 2-5A probe from binding to the proteins even at a concentration of 10 $\mu$M (lane 18). However, the inosine analogue, p$_3$I2'pA2'pA, Imai, J. et al., *J. Biol. Chem.*, 260:1390–1393 (1985), is able to prevent probe binding to both proteins but only when added at a concentration of about 1.0 $\mu$M (lane 22).

To further define sequences involved in 2-5A binding, nested 3'-deletions of the murine 2-5A-dependent RNase cDNA, clone ZB1, are constructed, transcribed in vitro, and expressed in a wheat germ extract. See FIG. 7B. The different deletion clones produces comparable amounts of polypeptide as monitored by incorporation of $^{35}$S-methionine. The levels of 2-5A binding activity are determined with the 2-5A probe in both a filter binding assay, Knight, M. et al., *Nature*, 288:189–192 (1980), and the uv crosslinking assay, Nolan-Sorden, N. L. et al., *Anal. Biochem.*, 184:298–304 (1990), with similar results. See FIG. 7B. Expression of clone ZB11, encoding amino acid residues 1 to 342, results in a loss of only about 26% of the 2-5A binding activity as compared to clone ZB1 (amino acids 1 to 656). See FIG. 7B. Clones intermediate in length between ZB1 and ZB11 all result in significant levels of 2-5A binding activity. In contrast, protein produced from ZB13 (amino acids 1 to 294) results in only about 38.3% of the 2-5A binding activity of clone ZB1, suggesting that a region important for the 2-5A binding function is affected. Indeed, clone ZB14 produced a protein encoding amino acids 1 to 265 which is nearly inactive in the 2-5A binding assay (only 1.9% of th activity of clone ZB1). Interestingly, the significant decrease in 2-5A binding activity observed with ZB14 occurs with the deletion of one of two P-loop motifs; nucleotide binding domains in many proteins. See FIGS. 4 and 7B. See also Saraste, M. et al., *TIBS*, 14:430–434 (1990). Deletion of both P-loop motifs in clone ZB15 results in protein (amino acids 1 to 218) which is completely lacking in 2-5A binding activity. See FIG. 7B.

To probe the involvement of the consensus lysine residues in the P-loop motifs in 2-5A binding activity, site-directed mutagenesis is performed on the truncated form of murine 2-5A-dependent RNase encoded by clone ZB1. Previously, it is reported that substitution mutations of the conserved lysine residues in P-loop motifs of eucaryotic initiation factor 4A and for *Bacillus anthracis* adenylyl cyclase results in a loss of ATP binding and catalytic activities, respectively. See Rozen et al., *Mol. Cell. Biol.*, 9:4061–4063 (1989) and Xia, Z. and Storm, D. R., *J. Biol. Chem.*, 265:6517–6520 (1990). In the former study the invariant lysine residue is mutated to asparagine. See Rozen et al., *Mol. Cell. Biol.*, 9:4061–4063 (1989). We substituted, individually and together, the consensus lysines with asparagines at positions 240 and 274 in the two P-loop motifs of 2-5A-dependent RNase. See FIG. 8 and the Example. Analysis of the effects of these mutations on 2-5A binding activity is determined by covalently crosslinking the $^{32}$P-2-5A probe to the in vitro translation products under uv light. See FIG. 8A. See also Nolan-Sorden, N. L. et al., *Anal. Biochem.*, 184:298–304 (1990). Similar levels of proteins are synthesized from the different mRNA species as shown in separate reactions containing $^{35}$S-methionine. See FIG. 8B. The three mutant forms of 2-5A-dependent RNase shows reduced binding to the 2-5A probe. See FIG. 8A, lanes 2 to 4. Clone ZB1 (Lys$^{240}$-)Asn), FIG. 8A, lane 2, expresses a mutant 2-5A-dependent RNase with a substantially reduced affinity for 2-5A; about 48.4% of the activity of clone ZB1 as determined by phosphorimager analysis (Molecular Dynamics) of the dried gel. A more modest reduction in 2-5A binding activity, to 79% of the control value, is obtained from clone ZB1(Lys$^{274}$-)Asn). See FIG. 8A, lane 3. In contrast, 2-5A binding activity from clone ZB1(Lys$^{240,274}$-)Asn), FIG. 8A, lane 4, in which both conserved lysine residues are replaced with asparagine residues, is reduced to only 12.2% of the activity of clone ZB1 (averaged from three separate experiments). These results suggest that the lysine residues at positions 240 and 274 function within the context of a repeated P-loop motif in the binding of 2-5A to 2-5A-dependent RNase.

The molecular cloning and expression of 2-5A-dependent RNase, the terminal factor in the 2-5A system and a key enzyme in the molecular mechanisms of interferon action is described. See FIG. 1. The recombinant proteins produced in vitro are demonstrated to possess 2-5A binding properties identical to naturally occurring forms of murine and human 2-5A-dependent RNase. See FIGS. 2, 5A, and 7. In addition, linkage of a $^{32}$P-2-5A analogue to a truncated murine 2-5A-dependent RNase and to murine L cell 2-5A-dependent RNase followed by partial proteolysis reveals identical patterns of labeled peptides. See FIG. 2B. Furthermore, the full-length recombinant human 2-5A-dependent RNase isolated on the activating, affinity matrix, 2-5A-cellulose, shows potent ribonuclease activity towards poly(U) but none against poly(C). See FIG. 5B. Similarly, it is previously demonstrated that murine L cell 2-5A-dependent RNase was activated by 2-5A-cellulose resulting in the cleavage of poly(U), but not of poly(C). See Silverman, R. H., *Anal. Biochem.*, 144:450–460 (1985). The full-length human 2-5A-dependent RNase, which is produced in reticulocyte lysate, had the same apparent molecular weight as did naturally occurring 2-5A-dependent RNase. See FIG. 5A. However, the actual molecular mass of human 2-5A-dependent RNase is determined from the predicted amino acid sequence, FIG. 3B, to be about 83,539 Da.

Previously, it was reported that interferon enhances levels of 2-5A-dependent RNase by between two- to twenty-fold depending on the cell type. See Silverman, R. H. et al., *Eur. J. Biochem.*, 126:333–341 (1982b) and Jacobsen, H. et al., *Virology*, 125:496–501 (1983a). Results presented herein suggest that the gene for 2-5A-dependent RNase may be an interferon-stimulated gene. See FIG. 6. Levels of 2-5A-dependent RNase mRNA in murine L929 cells are elevated as a function of time of interferon ($\alpha$+$\beta$) treatment by a factor of about three. Furthermore, the induction appeared to be a primary response to interferon treatment because it is observed in the presence of cycloheximide. Therefore, interferon is believed to regulate the 2-5A pathway by elevating levels of both 2-5A synthetases, Hovanessian, A. G. et al., *Nature*, 268:537–539 (1977), and 2-5A-dependent RNase, Jacobsen, H. et al., *Virology*, 125:496–501 (1983a). See FIGS. 1, 6 and 11.

The cloning of 2-5A-dependent RNase reveals several features of the protein. The 2-5A binding domain is of particular interest because it is the ability of 2-5A-dependent RNase to be activated by 2-5A that sets it apart from other nucleases. By expressing nested 3'-deletions of murine 2-5A-dependent RNase, a region between amino acids residues 218 and 294 which is believed to be critical for 2-5A binding activity is identified. See FIG. 7B. Interestingly, the identified region contains a repeated P-loop motif, one from residues 229 to 241 and another from residues 253 to 275. See FIG. 4 and Table 2. When the latter P-loop motif (amino acids 253–275) is partially deleted, there is a precipitous decline in 2-5A binding activity. See clone ZB14 in FIG. 7B.

The homology with P-loops is believed to be highly conserved between the human and murine forms of 2-5A-dependent RNase; thus underscoring the belief of the importance of this region for 2-5A binding activity. See FIG. 4. The similarity to P-loops consists of the tripeptides, glycine-lysine-threonine, preceded by glycine-rich sequences. In this regard, the unusual feature of 2-5A-dependent RNase is that the P-loop motif is repeated and are in the same orientation. Adenylyl cyclase from *Bacillus anthracis* also contains a duplicated P-loop motif, however, the two sequences are in opposite orientation and are overlapping. See Xia, Z. and Storm, D. R., *J. Biol. Chem.*, 265:6517–6520 (1990).

The relative importance of the conserved P-loop lysines (at positions 240 and 274) are evaluated by site-directed mutagenesis of the murine 2-5A-dependent RNase, clone ZB1. Although individual substitution mutations of the two lysines significantly reduced 2-5A binding activity, replacing both of the lysines with asparagine residues in the same mutant RNase severely represses 2-5A binding. See FIG. 8. Perhaps the trimer 2-5A requirement for activation of most forms of 2-5A-dependent RNase could be explained if the first and third adenylyl residues of 2-5A interact with the separate P-loop sequences inducing conformational changes in 2-5A-dependent RNase. In this regard, dimer 2-5A neither binds 2-5A-dependent RNase efficiently nor does it activate 2-5A-dependent RNase, FIG. 7A; Kerr, I. M. and Brown, R. E., *Prod. Natl. Acad. Sci. U.S.A.*, 75:265–260 (1978) and Knight, M. et al., *Nature*, 288:189–192 (1980), perhaps because it is too short to span the two P-loop motifs. Alternately, the residual 2-5A binding activity observed in the point mutants, ZB1(Lys$^{240}$-)Asn) and ZB1(Lys$^{274}$-)Asn), and the very low affinity of the double mutant, ZB1(Lys$^{240,274}$-)Asn) for 2-5A, could indicate that the two P-loop motifs are parts of separate 2-5A binding domains.

Homology with protein kinase domains VI and VII is also identified in 2-5A-dependent RNase. See FIG. 4. See also Hanks, S. K. et al., *Science*, 241:42–52 (1988). Although domain VI is believed to be involved in ATP binding, this region in 2-5A-dependent RNase is believed not to be important for 2-5A binding because its deletion caused only a minimal reduction in affinity for 2-5A. See FIG. 7B. However, a modest (two-fold) stimulatory effect of ATP on 2-5A-dependent RNase activity has been reported. See Wreschner, D. H. et al., *Eur. J. Biochem.*, 124:261–268 (1982) and Krause, D. et al., *J. Biol. Chem.*, 261:6836–6839 (1986). The latter report indicated that ATP was not required for 2-5A-dependent RNase activity but may act to stabilize the enzyme. Therefore, the region of homology with protein kinases could perhaps bind ATP resulting in stimulation of ribonuclease activity through stabilization of the enzyme.

A consensus zinc finger domain, reviewed in Evans, R. M. and Hollenberg, S. M., *Cell*, 52:1–3 (1988), consisting of six cysteine residues with the structure $CX_4CX_3CX_{17}CX_3CX_3C$ (amino acid residues 401–436 in Table 2) is identified in the murine form of 2-5A-dependent RNase. See FIG. 4. The homologous region in the human form of 2-5A-depenent RNase is $CX_{11}CX_{25}CX_3CX_6C$ (amino acid numbers 395 to 444 in Table 1). Because zinc fingers are nucleic acid binding domains, the cysteine-rich region in 2-5A-dependent RNase could be involved in binding to the RNA substrate. Alternatively, the cysteine-rich domain in 2-5A-dependent RNase could mediate formation of 2-5A-dependent RNase dimers. Analysis of crude preparations of 2-5A-dependent RNase suggest that 2-5A-dependent RNase may form dimers in concentrated but not in dilute extracts. See Slattery, E. et al., *Proc. Natl. Acad. Sci. U.S.A.*, 76:4778–4782 (1979) and Wreschner, D. H. et al., *Eur. J. Biochem.*, 124:261–268 (1982).

Comparison between the amino acid sequences of other ribonucleases with 2-5A-dependent RNase identifies some limited homology with RNase E, an endoribonuclease from *E. coli.* See FIG. 9A. See also Apirion D. and Lassar, A. B., *J. Biol. Chem.*, 253:1738–1742 (1978) and Claverie-Martin, F. et al., *J. Biol. Chem.* 266:2843–2851 (1991). The homology with RNase E is relatively conserved between the human and murine forms of 2-5A-dependent RNase and spans a region of about 200 amino acid residues. Within these regions there are 24 and 32% identical plus conservative matches, with some gaps, between RNase E and the human and murine forms of 2-5A-dependent RNase, respectively. See FIG. 9A. The rne gene which encodes RNase E and the altered mRNA stability (ams) gene, Ono, M. and Kumano, M., *J. Mol. Biol.,* 129:343–357 (1979), map to the same genetic locus. See Mudd E. A. et al., *Mol. Microbiol.,* 4:2127–2135 (1990); Babitzke, P. and Kushner, S. R., *Proc. Natl. Acad. Sci. U.S.A.,* 88:1–5 (1991) and Taraseviciene, L. et al., *Mol. Microbiol.,* 5:851–855 (1991). RNase E is required for both efficient mRNA turnover and rRNA processing in *E. coli.* See Mudd E. A. et al., *Mol. Microbiol.,* 4:2127–2135 (1990) and Babitzke, P. and Kushner, S. R., *Proc. Natl. Acad. Sci. U.S.A.,* 88:1–5 (1991). The cleavage specificities of 2-5A-dependent RNase and RNase E are similar in that 2-5A-dependent RNase cleaves mainly after UU or UA, Wreschner, D. H. et al., *Nature,* 289:414–417 (1981a) and Floyd-Smith, G. et al., *Science,* 212:1020–1032 (1981), and RNase E usually cleaves within the central AUU sequence of (G or A)AUU(A or U), Ehretsmann, C. P. et al., *Genes & Development,* 6:149–159 (1992). The location of the RNase E homology and other identified features in 2-5A-dependent RNase are shown. See FIG. 9B. These findings raise the possibility that RNase E may be the ancestral precursor of 2-5A-dependent RNase. In this regard, there are indications of 2',5'-oligoadenylates in *E. coli.* See Brown, R. E. and Kerr, I. M., *Process in Clinical and Biological Research,* 202:3–10 (1985) and Trujillo, M. A. et al., *Eur. J. Biochem.,* 169:167–173 (1987). However, the evolutionary distribution of a complete 2-5A system (i.e. 2-5A synthetase and 2-5A-dependent RNase) is reported to begin only with reptiles or possibly amphibia. See Cayley, P. J. et al., *Biochem. Biophys. Res. Commun.,* 108:1243–1250 (1982).

Endoribonucleases play a controlling role in RNA metabolism by catalyzing the rate-limiting steps in RNA decay. See Brawerman, G., *Cell,* 57:9–10 (1989). 2-5A-dependent RNase is a uniquely regulated endoribonuclease which mediates effects of interferon against picornaviruses. It functions by binding 2-5A and subsequently degrades both viral and cellular RNA. See Wreschner, D. H. et al., *Nucleic Acids Res.,* 9:1571–1581 (1981b). In addition, the 2-5A system may be involved in the antiproliferative effects of interferon and in the fundamental control of RNA stability. Cellular levels of 2-5A-dependent RNase and/or 2-5A-synthetase are regulated during interferon-treatment, Hovanessian, A. G. et al., *Nature,* 268:537–539 (1977) and Jacobsen, H. et al., *Virology,* 125:496–501 (1983a), cell growth arrest, Stark, G. et al., *Nature,* 278:471–473 (1979) and Jacobsen, H. et al., *Proc. Natl. Acad. Sci. U.S.A.,* 80:4954–4958 (1983b), cell differentiation, Krause, D. et al., *Eur. J. Biochem.,* 146:611–618 (1985), changing hormone status, e.g., Stark, G. et al., *Nature,* 278:471–473 (1979), and liver regeneration, Etienne-Smekens, M. et al., *Proc. Natl. Acad. Sci. U.S.A.,* 80:4609–4613 (1983). However, basal levels of 2-5A-dependent RNase and 2-5A synthetase are present in most if not all mammalian cells. The existence of multiple forms of 2-5A synthetase with different intracellular locations, Hovanessian, A. G. et al., *EMBO J.,* 6:1273–1280 (1987), could indicate diverse functions for the 2-5A system. Similarly, the ubiquitous presence of the 2-5A system in higher animals suggests an important function for 2-5A-dependent RNase, Cayley, P. J. et al., *Biochem. Biophys. Res. Commun.,* 108:1243–1250 (1982). For instance, 2-5A-dependent RNase cleaves rRNA at specific sites in intact ribosomes, Wreschner, D. H. et al., *Nucleic Acids Res.,* 9:1571–1581 (1981b) and Silverman, R. H. et al., *J. Virol.,* 46:1051–1055 (1983), possibly affecting translation rates. The transient nature of 2-5A, Williams, B. R. G. et al., *Eur. J. Biochem.,* 92:455–562 (1978), and its growth inhibitory effect after introduction into cells, Hovanessian, A. G. and Wood, J. N., *Virology,* 101:81–89 (1980), indicate that the 2-5A system is a tightly regulated pathway.

EXAMPLE I

The source of mRNA for preparing the cDNA library is murine L929 cells grown in EMEM (Whittaker, Inc.) and supplemented with about 10% FBS (Gibco-BRL), and antibiotics. The cells are treated with about 50 µg per ml of cycloheximide and 1000 units per ml of murine interferon ($\alpha+\beta$) ($1.3 \times 10^7$ units per mg protein: Lee Biomolecular) for about 2.5 hours to increase levels of 2-5A-dependent RNase mRNA. Total RNA was then isolated, e.g. Chomczynski, P. and Sacchi, N., *Anal. Biochem.,* 162:156–159 (1987), from which poly(A)$^+$ RNA is prepared by oligo(dT)-cellulose chromatography as described. See Sambrook, J. et al., *Cold Spring Harbor Laboratory Press* (1989). Synthesis of the first strand of cDNA is done by using reverse transcriptase as described (Superscript; BRL) except that 5-methyl-dCTP is substituted for dCTP and an XhoI-oligo-dT adapter-primer (Stratagene) is used. Synthesis of the second strand of cDNA and ligation of EcoRI linker was as described (Stratagene). The cDNA is digested with EcoRI and XhoI and unidirectionally cloned into predigested λZAPII vector (Stratagene). The library is packaged by using Giagpack Gold extract and titered on PLK-F bacteria.

The cDNA library is screened directly without prior amplification at a density of about 25,000 phage per 150 mm plate. Phage are grown for 3.5 hours at about 42° C. until plaques are visible. Nitrocellulose filters saturated in IPTG (10 mM) and then dried, are overlaid on the plates and growth was continued for an additional 4 to 6 hours at 37° C. The filters are processed by a modification of the methods of Singh, H. et al., *Cell,* 52:415–423 (1988) and Singh, H. et al., *BioTechniques,* 7:252–261 (1989). Filters are washed in ice-cold binding buffer (about 20 mM Tris-HCl, about pH 7.5, about 20 mM magnesium acetate, about 50 mM potassium chloride, about 1 mM EDTA, about 50 mM β-mercaptoethanol, about 0.1 mM PMSF, about 5% glycerol) containing about 6M guanidine-HCl for about 20 min. The solution containing the filters is then diluted two-fold with binding buffer and washing on ice is continued for about an additional 5 minutes; serial two-fold dilutions were continued until the guanidine concentration was about 187 mM. The filters are then washed twice with binding buffer, and incubated with binding buffer containing about 5% nonfat milk for one hour at about room temperature. The filters are then washed twice with binding buffer and incubated in binding buffer (supplemented with about 0.25% nonfat dry milk and about 0.02% sodium azide) containing p(A2'p)$_2$(br$^8$A2'p)$_2$A3'-[32P]Cp (the "2-5A probe"), Nolan-Sorden, N. L. et al., *Anal. Biochem.,* 184:298–304 (1990), at about $2 \times 10^5$ counts per minute per ml (about 3,000 Ci per mmole) at about 4° C. with shaking for about 24 hours. The filters are washed twice with binding buffer and then twice with water before air drying and exposing to film.

Murine L929 cells are treated with about 1000 units per ml interferon ($\alpha+\beta$) with or without about 50 µg per ml of cycloheximide and the total RNA is then isolated as described. See Chomczynski, P. and Sacchi, N., *Anal. Biochem.,* 162:156–159 (1987). Poly(A)$^+$ RNA is prepared by oligo(dT)-cellulose chromatography, as described in Sambrook, J. et al., *Cold Spring Harbor Laboratory Press* (1989), and is separated on glyoxal agarose gels and transferred to Nytran membranes. RNA is immobilized on the membrane by uv crosslinking (Stratalinker, Stratagene). The murine 2-5A-dependent RNase cDNA is $^{32}$P-labeled by random priming and then hybridized to the filter [about 50% formamide, about 10% dextran sulphate, Denhardt's solution about 1% SDS, 6× SSPE, Sambrook, J. et al., *Cold Spring Harbor Laboratory Press* (1989), about 250 µg per ml salmon sperm DNA] at about 42° C.

The Human 2-5A-dependent RNase cDNA clone, HZB1, is isolated from an adult human kidney cDNA library in λgt10 with radiolabeled (random primed) murine 2-5A-dependent RNase cDNA (clone ZB1) as probe, Sambrook, J. et al., *Cold Spring Harbor Laboratory Press* (1989). Clone HBZ22 is isolated using radiolabeled HZB1 DNA as probe. The genomic human 2-5A-dependent RNase clone is isolated from a human placenta cosmid library in vector pVE15 (Stratagene) with a radiolabeled fragment of HZB22 DNA as probe. The murine genomic 2-5A-dependent RNase clone is isolated from a mouse 129SV genomic library in vector λFIXII (Stratagene) with a radiolabeled fragment of 2-5A-BP cDNA (clone ZB1) as probe. Subcloning of DNA is in Bluescript vectors (Stratagene).

Transcription of plasmids with phage RNA polymerases is in the presence of mGppppG as described (Promega) except that reaction mixtures are supplemented with 15% dimethyl sulfoxide and incubations are at about 37° C. for about 90 minutes. RNA is purified through Sephadex G50 spun-columns and ethanol precipitated prior to translation. Protein synthesis was performed, as described (Promega), at about 30° C. for about one hour in micrococcal nuclease-pretreated rabbit reticulocyte lysate or in an extract of wheat germ at about room temperature for about one hour and then at about 40° C. for about 12 hours. Translation reactions contain about 50 µM zinc sulfate. Endogenous 2-5A-dependent RNase in the reticulocyte lysated is removed by adsorption to about 30 µM of $p_2(A2'p)_3A$ covalently attached to cellulose (2-5A-cellulose), prepared as described in Wells, J. A. et al., *J. Biol. Chem.*, 259:1363–1370 (1984) and Silverman, R. H. and Krause, D., *I.R.L. Press, Oxford, England*, pp. 149–193 (1987), for about one hour on ice as described. See Silverman, R. H., *Anal. Biochem.*, 144:450–460 (1985). The 2-5A-dependent RNase:2-5A-cellulose complex is removed by twice centrifuging at about 400×g for about 5 minutes at about 2° C. The supernatant completely lacking in measurable levels of 2-5A-dependent RNase. See FIG. 5.

The set of nested 3'-deletions of the truncated murine 2-5A-dependent RNase cDNA, ZB1, is generated with exonuclease III/S1 nuclease digestion followed by filling-in with Klenow DNA Polymerase using the "Erase-A-Base" system (Promega).

The synthesis of the 2-5A probe, $p(A2'p)_2(br^8A2'p)_2A$ [32P]Cp, and its crosslinking to 2-5A-dependent RNase is performed exactly as described. See Nolan-Sorden, N. L. et al., *Anal. Biochem.*, 184:298–304 (1990). Briefly, the 2-5A probe, about 0.7 to 2.5 nM at 3,0009 Ci/mmole, is incubated for about one hour on ice with cell extract prepared as described, Silverman, R. H. and Krause, D., *I.R.L. Press, Oxford, England*, pp. 149–193 (1987), in the absence or presence of unlabeled oligonucleotide competitors. Covalent crosslinking is done under a uv lamp (308 nm) for one hour on ice and the proteins are separated on SDS/10% polyacrylamide gels. Filter assays for 2-5A binding activity using the 2-5A probe for about one hour on ice, as described in Knight, M. et al., *Nature*, 288:189–192 (1980).

Protease digestions are performed on gel-purified proteins in a gel, as described by Cleveland, D. W. et al., *J. Biol. Chem.*, 252:1102–1106 (1977).

The ribonuclease assay with 2-5A-cellulose is performed, as described by Silverman, R. H., *Anal. Biochem.*, 144:450–460 (1985). Briefly, lysates are adsorbed to about 30 µM of 2-5A-cellulose on ice for about two hours. The matrix is then washed three times by centrifuging and resuspending in buffer A. See Silverman, R. H., *Anal. Biochem.*, 144:450–460 (1985). The matrix is then incubated with poly(U)-[$^{32}$P]Cp or poly(C)-[$^{32}$P]Cp (both at about 16 µM in nucleotide equivalents) at about 30° C. and the levels of acid-precipitable radioactive RNA are determined by filtration on glass-fiber filters.

The Sanger dideoxy sequencing method is used to determine the DNA sequences (Sequenase, United States Biomedical).

The lysines in the truncated murine 2-5A-dependent RNase, clone ZB1, at positions 240 and 274 are mutated, individually and together, to asparagine residues. Mutants ZB1(Lys$^{274}$-)Asn) and the double mutant, ZB1(Lys$^{240,274}$-)Asn), are obtained with mutant oligonucleotides after subcloning ZB1 cDNA into pALTER-1 as described (Promega). Mutant ZB1(Lys$^{240}$-)Asn) is obtained after polymerase chain reaction amplification of a segment of ZB1 with an upstream primer containing a unique HincII site attached to the mutant sequence and a second primer downstream of a unique BglII site. The HincII- and BGlII-digested polymerase chain reaction product and similarly-digested clone ZB1 are then ligated. The specific mutations are: for codon 240, AAA→AAC and for codon 274, AAG→AAC. Mutants are confirmed by DNA sequencing.

EXAMPLE II

Seeds of tobacco (*Nicotiana tabacum* cv. Wisconsin) and Ti based binary vectors pAM943 and pAM822 were obtained from Dr. Amit Mitra, Department of Plant Pathology, University of Nebraska, Lincoln, Nebr. The *Agrobacterium tumefaciens* LBA4404 and the *E. coli* strains K802 and MM294 were purchased from Clonetech, Palo Alto, Calif. and Stragene, Lajolla, Calif. The plant tissue culture medium Murashige and Skoog's ready mix (MS media) was purchased from Sigma Chemical Company, St. Louis, Mo. The human cDNAs for PKR, the lysine→arginine mutant PKR, and 2-5A synthetase were obtained from Dr. B. R. G. Williams, Department of Cancer Biology, The Cleveland Clinic Foundation. See, for example, Meurs, E. et al.: *Cell*, 62:379–390 (1990); Chong, K. L. et al.: *EMBO J.*, 11:1553–1562 (1992); Rysieki, G. et al.: *J. Interferon Res.*, 9:649–657 (1989); Benech, P. et al.: *EMBO J.*, 4:2249–2256 (1985); and Saunders, M. E. et al.: *EMBO J.*, 4:1761–1768 (1985). The human cDNA for 2-5A dependent RNase, as shown in FIG. 3A, was cloned in Dr. R. H. Silverman's laboratory in the Department of Cancer Biology and is the property of The Cleveland Clinic Foundation. See, Zhou, A. et al.: *Cell*, 72:753–765 (1993).

The expression vector pAM943 is used to obtain Agrobacterium-mediated transfer of T DNA containing the cDNAs and kanamycin resistance marker gene. The physical map of the plasmid vector pAM943 shows its elements. See FIG. 12. The plasmid pAM943 contains a dual promoter consisting of the adenyl methyl transferase (AMT) gene promoter of Chlorella virus and the wild type 35S promoter of Cauliflower mosaic virus. The vector also contains the gene for kanamycin resistance to select the transformed plants. Initially, the cDNAs are subcloned in pAM943 and amplified in *E. coli* strains K802 or MM294 using tetracycline resistance as the selectable marker. The Agrobacterium cells are transformed with the recombinant pAM943 plasmids and selected by growth in medium containing about 5 µg/ml of tetracycline, about 10 µg/ml of kanamycin and about 25 µg/ml of streptomycin.

To subclone cDNAs for PKR (PK68), a lysine→arginine mutant PKR (muPk68; the mutant PKR protein binds to dsRNA but has no kinase activity and will thus function as a control), and a low molecular weight form of 2-5A-synthetase (synthetase), the plasmids pKS(+)PKR, pKS(+) muPKR, and pKS(+)synthetase are digested first with XbaI and than with ClaI restriction endonucleases, the cDNA fragments are purified from low melting point agarose gels and subcloned in sense orientation at XbaI and ClaI sites of pAM943. See FIG. 13. The recombinant plasmids, e.g., construct A, pAM943:PK68, construct B, pAM943:muPK68, and contruct C, pAM943:synthetase, which correspond to the constructs depicted in FIGS. 13A–C, respectively, are used to transform *Agrobacterium tumefaciens* LBA4404. The resultant bacteria, identified as AG68, AGmu68 and AGsyn, respectively, are used for tobacco leaf disc transformations. Production of the recombinant plasmids, i.e., construct A, pAM943:PK68, construct B, pAM943:muPK68, and construct C pAM943:synthetase, is described in greater detail hereinafter.

To subclone cDNA for 2-5A-dependent RNase, the plasmid pKS(+)2C5 DNA is digested with HindIII enzyme and subcloned in the HindIII site of pAM943 in both orientations, see FIG. 13, and the recombinant plasmids, construct D, pAM943:2-5A-dep. RNase sense and construct D/a, pAM943:2-5A-dep. RNase antisense, both of which correspond to constructs D and D/a, respectively, in FIG. 13D and D/a, are used to transform Agrobacterium to obtain the bacteria called AG2DR sense and AG2DR antisense, respectively. Production of the recombinant plasmids, i.e., construct D, pAM943:2-5A-dep. RNase sense, construct D/a, pAM943:2-5A-dep. RNase antisense, and construct E, pAM822:2-5A dep. RNase antisense, is also described in greater detail hereinafter.

The competent Agrobacterium cells are prepared and transformation follows the method of, for example, An, G. et al.: *Plant Molecular Biology Manual*, AD:1–19 (1988). The presence of recombinant plasmids in the transformed Agrobacterium cells is confirmed by preparing plasmid DNA and by performing PCR using specific complementary oligonucleotides and by observing restriction enzyme digests.

The physical map of plasmid pAM822, one of the vectors used to deliver the reverse orientation cDNA for 2-5A dependent RNase into plant cells by electroporation, is also shown. See FIGS. 13E and 14. To subclone cDNA for 2-5A-dependent RNase into pAM822 the entire coding region of 2-5A-dependent RNase was PCR amplified using two oligonucleotide primers containing BamHI restriction sites before ATG (start codon) and after TGA (stop codon). The product was digested with BamHI and subcloned at BglII site of pAM822 vector. The cDNA used for 2-5A-dependent RNase is in plasmid pZC5 referenced in Zhou et al. Cell 72, 753–765 (1994), the human form of the cDNA. The sequence is also disclosed herein. The plasmid pAM822 contains a second selectable marker gene, the hygromycin resistance gene, permitting the construction of plants containing both 2-5A-synthetase and 2-5A-dependent RNase cDNAs. Insertion of pAM822:2-5Adep. RNase (FIG. 13E), containing 2-5A-dependent RNase cDNA, into kanamycin-resistant, transgenic tobacco leaf discs containing 2-5A-synthetase cDNA is thus performed.

Tobacco plants are grown aseptically in Murashige and Skoog's medium, known as MS medium, containing about 3% sucrose (MSO medium) and about 0.8% agar in plastic boxes (Phytatray) at about 28° C. under cycles consisting of about 16 hr of light and about 8 hr of dark in a growth chamber. Leaves bigger than about 2" long are cut into about 2 to 3 cm$^2$ pieces under the MSO medium and 6–8 leaf pieces are placed in a 6 cm Petri dish containing about 2 ml of MSO medium and holes are made in the leaf pieces with a sterile pointed forcep. Overnight cultures of AG68, AGmu68, AGSyn, AG2DR sense and AG2DR antisense are grown in LB (L broth) containing about 50 µM of acetosyringone and appropriate antibiotics at about 28° C. in a waterbath. One hundred microliter of overnight culture is added to each of the Petri dishes containing leaf pieces. Incubation is at about 28° C. under diffuse light in the growth chamber for about 2 days. Leaf pieces are washed extensively with MSO medium and transferred to solid agar for selection in shoot regeneration medium [MSO; about 0.5 mg/l BAP (benzylaminopurine); about 200 µg/ml kanamycin; about 200 µg/ml carbenicillin; and about 100 µg/ml of cefotaxine], under diffuse light at about 28° C. in the growth chamber. Within about 3 weeks, regeneration of plantlets is observed. When the plantlets are about 2–3 cm long they are transferred to root-inducing, hormone-free MSO solid agar medium containing about 200 µg/ml kanamycin and about 200 µg/ml carbenicillin. The transgenic plants expressing 2-5A synthetase are substantially transformed to introduce the cDNA for 2-5A-dependent RNase (with pAM943:2-5Adep.RNase sense, construct D; FIG. 13D). Alternatively, the vector pAM822 (FIG. 14) containing the 2-5A-dependent RNase cDNA in sense orientation and the hygromycin resistance gene is used to transform 2-5A-synthetase containing plants. This allows selection in hygromycin containing MSO media. Tissue culture and regeneration of plants are done as described above. Transgenic plants are grown to produce flowers and seeds to demonstrate the transfer of the antiviral genes or nucleotide sequences to subsequent generations. Although specific plasmid constructs are described herein, the present invention is intended to include any plant vector including those with inducible promoters.

Expression of PKR, mutant PKR, 2-5A-synthetase, and 2-5A-dependent RNase in plants that are 4" to 5" tall are tested in protein extracts of leaves (supernatant of 10,000×g centrifugation). Results of Northern and Southern blot assays and functional binding assays for 2-5A-dependent RNase are reported in Tables I–V. See also FIG. 15 wherein expression of human 2-5A synthetase cDNA in transgenic tobacco plants as determined by measuring the mRNA levels in a Northern blot is shown. FIG. 16, on the other hand, shows expression of mutant and wild type forms of human PKR cDNA in transgenic tobacco plants as determined by measuring mRNA levels in a Northern blot. FIG. 17 depicts presence of 2-5A-dependent RNase cDNA in transgenic tobacco plants as determined on a Southern blot.

TABLE I

Transgenic Tobacco Plants Expressing
Wild Type and Mutant Forms of Human PKR cDNA
(plasmid pAM943:PK68) FIG. 13A
(plasmid pAM943:muPK68) FIG. 13B

| Transgenic: | Plant: (clone #) | Southern Blot: (presence of DNA) | Northern Blot: (expression of mRNA) |
|---|---|---|---|
| Mutant PKR: | 1 | + | N.T. |
| (plasmid | 2 | ++ | + |
| pAM943:PK68) | 4 | N.T. | N.T. |
| FIG. 13A | 6 | N.T. | + |
| | 7 | N.T. | + |
| | 10 | N.T. | + |

TABLE I-continued

Transgenic Tobacco Plants Expressing
Wild Type and Mutant Forms of Human PKR cDNA
(plasmid pAM943:PK68) FIG. 13A
(plasmid pAM943:muPK68) FIG. 13B

| Transgenic: | Plant: (clone #) | Southern Blot: (presence of DNA) | Northern Blot: (expression of mRNA) |
|---|---|---|---|
| | 11 | N.T. | + |
| | 12 | N.T. | + |
| | 17 | N.T. | + |
| Wild Type | 1 | N.T. | + |
| PKR: | 2 | N.T. | N.T. |
| (plasmid | 5 | N.T. | + |
| pAM943:muPK68) | 6 | N.T. | N.T. |
| FIG. 13B | 7 | N.T. | N.T. |
| | 8 | N.T. | + |
| | 10 | N.T. | + |
| | 20 | N.T. | N.T. |
| | 22 | N.T. | N.T. |

N.T., Not Tested

TABLE II

Transgenic Tobacco Plants Expressing
Human 2-5A-Synthetase cDNA
(Plasmid pAM943:synthetase - FIG. 13C)

| Plant: (clone #) | Southern Blot: (presence of DNA) | Northern Blot: (expression of mRNA) |
|---|---|---|
| 1 | ++ | + |
| 3 | ± | N.T. |
| 4 | + | ++ |
| 5 | ± | N.T. |
| 6 | ± | N.T. |
| 7 | ± | N.T. |
| 8 | +++ | + |
| 9 | + | N.T. |
| 10 | + | + |
| 12 | + | N.T. |
| 13 | + | N.T. |
| 14 | ++ | − |
| 15 | + | ± |
| 16 | + | − |
| 17 | N.T. | ++ |
| 18 | N.T. | ++ |
| a | N.T. | N.T. |
| b | N.T. | N.T. |
| c | N.T. | N.T. |
| d | N.T. | N.T. |

N.T., Not Tested.

TABLE III

Transgenic Tobacco Plants Containing
Sense or Antisence Orientation Human
2-5A-Dependent RNase cDNA
(plasmid pAM943:2-5A-dep. RNase sense -FIG. 13D)
(plasmid pAM943:2-5A-dep. RNase antisense - FIG. 13D/a)

| Transgenic: | Plant: (clone #) | Southern (presence of DNA) | Northern (expression of mRNA) | 2-5A-Binding Assay: (protein activity |
|---|---|---|---|---|
| Antisense: | 1 | + | N.T. | N.T. |
| | 2 | + | N.T. | N.T. |
| | 3 | + | N.T. | N.T. |
| | 4 | + | N.T. | N.T. |
| | 5 | + | N.T. | N.T. |
| | a | N.T. | N.T. | N.T. |
| | b | N.T. | N.T. | N.T. |
| | c | N.T. | N.T. | N.T. |

TABLE III-continued

Transgenic Tobacco Plants Containing
Sense or Antisence Orientation Human
2-5A-Dependent RNase cDNA
(plasmid pAM943:2-5A-dep. RNase sense -FIG. 13D)
(plasmid pAM943:2-5A-dep. RNase antisense - FIG. 13D/a)

| Transgenic: | Plant: (clone #) | Southern (presence of DNA) | Northern (expression of mRNA) | 2-5A-Binding Assay: (protein activity |
|---|---|---|---|---|
| Sense: | Z1 | + | − | + |
| | Z2 | ++ | − | ++ |
| | Z3 | ++ | N.T. | ++ |
| | Z4 | + | N.T. | N.T. |
| | Z5 | N.T. | N.T. | +++ |
| | Z6 | N.T. | N.T. | ++ |
| | Z7 | N.T. | N.T. | +/− |

N.T., Not Tested.

TABLE IV

Transgenic Tobacco Plants Containing Both Human
2-5A-Synthetase and Human 2-5A-Dependent RNase cDNA
(plasmid pAM943:synthetase - FIG. 13C)
(plasmid pAM943:2-5A-dep. RNase sense - FIG. 13D)

| | | Southern Blots: | | Northern Blot: | |
|---|---|---|---|---|---|
| Plant: (clone #) | (2-5A-Syn DNA) | (2-5A-Dep. RNase DNA) | (2-5A Syn. mRNA) | (2-5A-dep. RNase mRNA |
| 14/1 | N.T. | − | + | − |
| 14/2 | N.T. | − | + | − |
| 14/3 | N.T. | N.T. | N.T. | N.T. |
| 14/4 | N.T. | N.T. | N.T. | N.T. |
| 14/5 | N.T. | N.T. | N.T. | N.T. |
| 14/6 | N.T. | N.T. | N.T. | N.T. |
| 15/1 | N.T. | − | + | − |
| 15/2 | N.T. | − | + | − |
| 15/3 | N.T. | − | + | − |
| 15/4 | N.T. | N.T. | + | − |
| 15/5 | N.T. | N.T. | N.T. | N.T. |
| 15/6 | N.T. | − | + | − |
| 15/7 | N.T. | − | N.T. | N.T. |

N.T., Not Tested.

Assays of dsRNA-dependent autophosphorylation of PKR, 2-5A synthetase activated with dsRNA, and 2-5A-dependent RNase by UV-crosslinking to radioactive 2-5A, see Nolan-Sorden et al.: *Analytical Biochemists*, (184) :298–304 (1990), may be performed on the leaf extracts. The levels of the proteins may also be determined by Western blot analysis using the antibodies against PKR, 2-5A-synthetase and 2-5A-dependent RNase.

To demonstrate the expression of 2-5A-dependent RNase in transgenic plants containing construct D, pAM943:2-5A-dep. RNase sense, as depicted in FIG. 13D, functional assays that measure binding of radiolabeled 2-5A analog to 2-5A-dependent RNase are performed. See Tables III and V. Results show the presence of 2-5A-dependent RNase in transgenic plants Z1, Z2, Z3, Z5 and Z6. It is believed that the highest levels of human, recombinant 2-5A dependent RNase are in plant Z5. See Table V.

TABLE V

Functional Expression of 2-5A-Dependent RNase
in Transgenic Tobacco Plants ad Determined
by a 2-5A Binding Assay
(plasmid pAM943:2-5A-dep. RNase sense - FIG. 13D)

| Plant; | 2-5A Binding Activity[a]: |
|---|---|
| Z1 | 662 |
| Z2 | 1,618 |
| Z3 | 1,545 |
| Z5 | 2,575 |
| Z6 | 1,547 |
| Z7 | 31 |

[a]Tobacco plants contain construct D, pAM943:2-5Adep. RNase (sense). 2-5A binding assays are performed by the filter binding method of Knight, M. et. al. Nature (288):189–192 (1980) with modifications. A $^{32}$P-labeled and bromine substituted 2-5A analog, p(A2'p)$_2$(br$^8$A2'p)$_2$A3'-$^{32}$p Cp, about 15,000 counts per min per assay, at about 3,000 Ci per mmole, Nolan-Sorden, N.L., et al. Anal. Biochem., (184):298–304 (1990), is incubated with plant extracts, containing about 100 micrograms of protein per assay, on ice for about 4 h. The reaction mixtures are then transferred to nitrocellulose filters which are washed twice in distilled water and dried and the amount of 2-5A probe bound to the 2-5A-dependent RNase on the filters is measured by scintillation counting, Silverman, R. H. and Krause, D., In, Clemens, M. J., Morris, A. G., and Gearing, A. J. H., (eds.), Lymphokines and Interferons - A Practical Approach, I.R.L. Press, Oxford, pp. 149–193 (1987). Data is presented as counts per min of labeled 2-5A bound to 2-5A-dependent RNase expressed in the transgenic plants. Background radioactivity from extracts of control plants, 705 counts per min, consisting of nonspecific binding of 2-5A, is subtracted from these data.

To further confirm that the transgenic plants containing 2-5A-dependent RNase cDNA express functional 2-5A-dependent RNase protein or an amino acid sequence, an affinity labeling method is performed (data not shown). In this method, 2-5A-binding activity is determined on a Western blot with a bromine-substituted, $^{32}$P-labeled 2-5A analog (the "probe"), as described in Nolan-Sorden, N. L. et al.: Anal. Biochem., 184:298–304 (1990). More particularly, leaves are collected from transgenic plants containing 2-5A-dependent RNase cDNA and they are homogenized in NP40 lysis buffer, see Silverman, R. H. and Krause, D. (1987) In, Clemens, M. J., Morris, A. G., and Gearing, A. J. H., (eds.), Lymphokines and Interferons—A Practical Approach, I.R.I., Press, Oxford, pp. 149–193, supplemented with about 5 mM ascorbic acid, about 1 mM cysteine, about 2 μg per ml leupeptin, about 100μ per ml phenylmethyleulfonyl fluoride, and about 2 μg per ml pepstatin. Extracts are clarified by centrifugation at about 10,000×g for about 10 min. Supernatants of the extracts, about 100 μg of protein per assay, are separated by SDS/10% polyacrylamide gel electrophoresis, followed by transfer of the proteins to Immobilon-P membrane filters (Millipore Corp., Bedford, Mass.). The filter is then incubated with about 4×10$^5$ c.p.m. per ml of $^{32}$P-labeled 2-5A probe for about 24 h at about 4° C., according to Zhou, A. et al.: Cell 73:753–765 (1993). The autoradiograms of the washed and dried filters show the presence of functional human 2-5A-dependent RNase visible to about 80 kDa bands, in plants Z3, Z5, and Z6 (data not shown).

Antiviral activity of the plants are determined by rubbing celite powder coated with Tobacco mosaic virus (ATCC) and Tobacco Etch virus (from Dr. Amit Mitra, Nebraska). The plants are monitored for symptoms of viral infection on leaves from control and transgenic plants and are documented in photographs.

The plasmids described and the transformed Agrobacterium strains can be used to transform any other plants into virus-resistant plants. Exemplary of plants that may be transformed in accordance with the present invention include vegetable plants like corn, potato, carrot, lettuce, cabbage, broccoli, cauliflower, bean, squash, pumpkin, pepper, onion, tomato, pea, beet, celery, cucumber, turnip and radish plants, fruit plants like banana, apple, pear, plum, apricot, peach, nectarine, cherry, key lime, orange, lemon, lime, grapefruit, grape, berry, and melon plants, grain plants like wheat, barley, rice, oat and rye plants, grass, flowers, trees, shrubs and weeds such as laboratory weeds like Arabidopsis. It should therefore be understood that the present invention includes any plant into which any nucleotide sequence encoding an amino acid having antiviral activity has been introduced to form transgenic plants having immunity or resistance against viral infection.

Construction of pAM943:PKR (Construct A) and
pAM943;MuPKR (Construct B)

The plasmids pKS(+)PKR and pKS(+)muPKR, encoding wild type PKR and a lysine to arginine at codon 296 mutant form of PKR, respectively, present in E. coli cells (obtained from Dr. B. R. G. Williams, Cleveland Clinic, Cleveland, Ohio) are prepared by standard methods. See, for example, Katze, M. G. et al.: Mol. Cell Biol., 11:5497–5505 (1991) for generation of muPKR, lysine—296→arginine mutant (K296R), by site specific mutagenesis as described. The PKR nucleotide sequence utilized to construct plasmids pKS(+)PKR and pKS(+)muPKR is depicted in FIG. 18. To determine the ability of a plant translation apparatus to synthesize PKR protein, capped PKR mRNA is produced from linearized pKS(+)PKR by in vitro transcription. The RNA is then translated in wheat germ extract (obtained from Promega Corp., Madison, Wis.) in the presence of $^{35}$S-methionine. Synthesis of the $^{35}$S-labeled PKR is detected in an autoradiogram of the dried, SDS/polyacrylamide gel.

The cDNAs encoding PKR and muPKR are excised from plasmids pKS(+)PKR and pKS(+)muPKR by digesting with KpnI and XbaI. The resulting DNA fragments containing the entire coding sequences for PKR and muPKR are purified from a low melting point agarose gel. To generate cDNAs containing at the 5' end XbaI and at the 3' end ClaI sites, the PKR cDNA and muPKR cDNA are then digested with ClaI and purified. The resulting digested PKR cDNA and muPKR cDNA are then force cloned into XbaI and ClaI digested pAM943 by DNA ligation. The resulting plasmids, FIG. 13, constructs A and B, are used to transform Agrobacterium tumefaciens strain LBA4404 (Clonetech, Plao Alto, Calif.). Recombinant plasmids are prepared from transformed Agrobacterium tumefaciens bacteria by standard methods and the presence of PKR and muPKR cDNA is confirmed by PCR analysis and restriction enzyme digests of the isolated plasmids.

Construction of pAM943:Synthetase (Construct C)

The plasmid ptac-15 containing the human cDNA illustrated in FIG. 20 for a small form of 2-5A-synthetase (producing a 1.8 kb mRNA) (obtained from Dr. B. R. G. Williams, Cleveland Clinic, Cleveland, Ohio) is prepared by standard methods and is digested with BamHI and EcoRI. The synthetase cDNA is purified from a low melting point agarose gel by standard methods and is then subcloned into plasmid pKS(+) (Strategene, La Jolla, Calif.) in BamHI and EcoRI sites. The resulting recombinant plasmid DNA (pKS (+)synthetase) is digested with XbaI and ClaI and the 2-5A synthetase cDNA is purified from a low melting point agarose gel and is then subcloned into XbaI and ClaI digested pAM943 to produce construct C (FIG. 13). Recombinant plasmids are prepared from transformed Agrobacterium tumefaciens bacteria by standard methods and the presence of 2-5A-synthetase cDNA is confirmed by PCR analysis and by restriction enzyme digests of the isolated plasmids.

Construction of pAM943:2-5Adep.RNase Sense
(Construct D) and pAM943:2-5Adep.RNase
Antisense (Construct D/a)

The plasmid pKS(+)ZC5 encoding a complete coding sequence for human 2-5A-dependent RNase is digested with HindIII. The 2.5 kbp cDNA for 2-5A-dependent RNase is purified in a low melting point agarose gel and is then subcloned in HindIII digested pAM943 in both sense (forward) and antisense (reverse) orientations to produce pAM943:2-5Adep.RNase sense (construct D) and pAM943:2-5Adep.RNase antisense (construct D/a), as depicted in FIG. 13D and D/a, respectively. Transformed Agrobacterium are determined to contain the 2-5A-dependent RNase cDNA by restriction enzyme digests and by PCR analysis.

Construction of pAN822:2-5Adep.RNase Antisense (Construct E)

Polymerase chain reactions (PCR) are performed on plasmid pKS(+)ZC5 encoding human 2-5A-dependent RNase to generate HindIII and BamHI sites on the two ends of the cDNA and to reduce 5' and 3' untranslated sequences. The PCR primers used are:

| ID SEQ NO:7: | 2DR-5 | 5'-TCATGCTCGAGAAGCTTGGATCCACCATGGAGAGCAGGGAT-3'; |
|---|---|---|
| and | | |
| ID SEQ NO:8: | H2DR-4 | 5'-GATACTCGAGAAGCTTGCATCCTCATCAGCACCCAGGGCTGG-3'. |

The PCR product (about 2.25 kbp) is purified on a low melting point agarose gel and is then digested with HindIII and is then subcloned into HindIII digested plasmid pKS(+). The resulting plasmid, pKS:pZC5 is digested with BamHI and the 2-5A-dependent RNase cDNA fragment is purified and cloned into BglII digested pAM822. Recombinants isolated in the reverse (antisense) orientation give pAM822:2-5Adep.RNase antisense (construct E). See FIG. 13E.

Plasmids depicted in FIGS. 13A, B, C and D have been deposited with the American Type Culture Collection, Rockville, Md., and assigned ATCC Accession Nos. 75996, 75997, 75998 and 75999, respectively.

As to the nucleotide sequences disclosed herein, A means adenine; C means cytosine; G means guanine; T means thymine; and U means uracil. With respect to the disclosed amino acid sequences, A means ala or alanine; R means arg or arginine; N means asn or asparagine; D means asp or aspartic acid; C means cys or cysteine; E means glu or glutamic acid; Q means gln or glutamine; G means gly or glycine; H means his or histidine; I means ile or isoleucine; L means leu or leucine; K means lys or Lysine; M means met or methionine; F means phe or phenylalanine; P means pro or proline; S means ser or serine; T means thr or threonine; W means trp or tryptophan; Y means tyr or tyrosine; and V means val or valine.

TABLE 1

Human 2-5A-depedent RNase
ID SEQ NO:1:, ID SEQ NO:2:, ID SEQ NO:3: and ID SEQ NO:4:

```
                                      -103 aat cccaact t acact caaagct
                                      t ct t t gat t aagt gct aggagat aaat t t gcat t t t ct ca
                                      aggaaaaggct aaaagt ggt agcaggt ggcat t t accgt c
```

| ATG | GAG | AGC | AGG | GAT | CAT | AAC | AAC | CCC | CAG | 30 |
|---|---|---|---|---|---|---|---|---|---|---|
| Met | Glu | Ser | Arg | Asp | His | Asn | Asn | Pro | Gln | 10 |
| GAG | GGA | CCC | ACG | TCC | TCC | AGC | GGT | AGA | AGG | 60 |
| Glu | Gly | Pro | Thr | Ser | Ser | Ser | Gly | Arg | Arg | 20 |
| GCT | GCA | GTG | GAA | GAC | AAT | CAC | TTG | CTG | ATT | 90 |
| Ala | Ala | Val | Glu | Asp | Asn | His | Leu | Leu | Ile | 30 |
| AAA | GCT | GTT | CAA | AAC | GAA | GAT | GTT | GAC | CTG | 120 |
| Lys | Ala | Val | Gln | Asn | Glu | Asp | Val | Asp | Leu | 40 |
| GTC | CAG | CAA | TTG | CTG | GAA | GGT | GGA | GCC | AAT | 150 |
| Val | Gln | Gln | Leu | Leu | Glu | Gly | Gly | Ala | Asn | 50 |
| GTT | AAT | TTC | CAG | GAA | GAG | GAA | GGG | GGC | TGG | 180 |
| Val | Asn | Phe | Gln | Glu | Glu | Glu | Gly | Gly | Trp | 60 |
| ACA | CCT | CTG | CAT | AAC | GCA | GTA | CAA | ATG | AGC | 210 |
| Thr | Pro | Leu | His | Asn | Ala | Val | Gln | Met | Ser | 70 |
| AGG | GAG | GAC | ATT | GTG | GAA | CTT | CTG | CTT | CGT | 240 |
| Arg | Glu | Asp | Ile | Val | Glu | Leu | Leu | Leu | Arg | 80 |

TABLE 1-continued

Human 2-5A-depedent RNase
ID SEQ NO:1:, ID SEQ NO:2:, ID SEQ NO:3: and ID SEQ NO:4:

| CAT | GGT | GCT | GAC | CCT | GTT | CTG | AGG | AAG | AAG | 270 |
|-----|-----|-----|-----|-----|-----|-----|-----|-----|-----|-----|
| His | Gly | Ala | Asp | Pro | Val | Leu | Arg | Lys | Lys | 90 |
|     |     |     |     | (CCT) | * |     |     |     |     |     |
| AAT | GGG | GCC | ACG | CTT | TTT | ATC | CTC | GCA | GCG | 300 |
| Asn | Gly | Ala | Thr | Leu | Phe | Ile | Leu | Ala | Ala | 100 |
|     |     |     |     | (Pro) | * |     |     |     |     |     |
| ATT | GCG | GGG | AGC | GTG | AAG | CTG | CTG | AAA | CTT | 330 |
| Ile | Ala | Gly | Ser | Val | Lys | Leu | Leu | Lys | Leu | 110 |
| TTC | CTT | TCT | AAA | GGA | GCA | GAT | GTC | AAT | GAG | 360 |
| Phe | Leu | Ser | Lys | Gly | Ala | Asp | Val | Asn | Glu | 120 |
| TGT | GAT | TTT | TAT | GGC | TTC | ACA | GCC | TTC | ATG | 390 |
| Cys | Asp | Phe | Tyr | Gly | Phe | Thr | Ala | Phe | Met | 130 |
| GAA | GCC | GCT | GTG | TAT | GGT | AAG | GTC | AAA | GCC | 420 |
| Glu | Ala | Ala | Val | Tyr | Gly | Lys | Val | Lys | Ala | 140 |
| CTA | AAA | TTC | CTT | TAT | AAG | AGA | GGA | GCA | AAT | 450 |
| Leu | Lys | Phe | Leu | Tyr | Lys | Arg | Gly | Ala | Asn | 150 |
| GTG | AAT | TTG | AGG | CGA | AAG | ACA | AAG | GAG | GAT | 480 |
| Val | Asn | Leu | Arg | Arg | Lys | Thr | Lys | Glu | Asp | 160 |
| CAA | GAG | CGG | CTG | AGG | AAA | GGA | GGG | GCC | ACA | 510 |
| Gln | Glu | Arg | Leu | Arg | Lys | Gly | Gly | Ala | Thr | 170 |
| GCT | CTC | ATG | GAC | GCT | GCT | GAA | AAA | GGA | CAC | 540 |
| Ala | Leu | Met | Asp | Ala | Ala | Glu | Lys | Gly | His | 180 |
| GTA | GAG | GTC | TTG | AAG | ATT | CTC | CTT | GAT | GAG | 570 |
| Val | Glu | Val | Leu | Lys | Ile | Leu | Leu | Asp | Glu | 190 |
| ATG | GGG | GCA | GAT | GTA | AAC | GCC | TGT | GAC | AAT | 600 |
| Met | Gly | Ala | Asp | Val | Asn | Ala | Cys | Asp | Asn | 200 |
| ATG | GGC | AGA | AAT | GCC | TTG | ATC | CAT | GCT | CTC | 630 |
| Met | Gly | Arg | Asn | Ala | Leu | Ile | His | Ala | Leu | 210 |
| CTG | AGC | TCT | GAC | GAT | AGT | GAT | GTG | GAG | GCT | 660 |
| Leu | Ser | Ser | Asp | Asp | Ser | Asp | Val | Glu | Ala | 220 |
| ATT | ACG | CAT | CTG | CTG | CTG | GAC | CAT | GGG | GCT | 690 |
| Ile | Thr | His | Leu | Leu | Leu | Asp | His | Gly | Ala | 230 |
| GAT | GTC | AAT | GTG | AGG | GGA | GAA | AGA | GGG | AAG | 720 |
| Asp | Val | Asn | Val | Arg | Gly | Glu | Arg | Gly | Lys | 240 |
| ACT | CCC | CTG | ATC | CTG | GCA | GTG | GAG | AAG | AAG | 750 |
| Thr | Pro | Leu | Ile | Leu | Ala | Val | Glu | Lys | Lys | 250 |
| CAC | TTG | GGT | TTG | GTG | CAG | AGG | CTT | CTG | GAG | 780 |
| His | Leu | Gly | Leu | Val | Gln | Arg | Leu | Leu | Glu | 260 |
| CAA | GAG | CAC | ATA | GAG | ATT | AAT | GAC | ACA | GAC | 810 |
| Gln | Glu | His | Ile | Glu | Ile | Asn | Asp | Thr | Asp | 270 |
| AGT | GAT | GGC | AAA | ACA | GCA | CTG | CTG | CTT | GCT | 840 |
| Ser | Asp | Gly | Lys | Thr | Ala | Leu | Leu | Leu | Ala | 280 |
| GTT | GAA | CTC | AAA | CTG | AAG | AAA | ATC | GCC | GAG | 870 |
| Val | Glu | Leu | Lys | Leu | Lys | Lys | Ile | Ala | Glu | 290 |
| TTG | CTG | TGC | AAA | CGT | GGA | GCC | AGT | ACA | GAT | 900 |
| Leu | Leu | Cys | Lys | Arg | Gly | Ala | Ser | Thr | Asp | 300 |
| TGT | GGG | GAT | CTT | GTT | ATG | ACA | GCG | AGG | CGG | 930 |
| Cys | Gly | Asp | Leu | Val | Met | Thr | Ala | Arg | Arg | 310 |
| AAT | TAT | GAC | CAT | TCC | CTT | GTG | AAG | GTT | CTT | 960 |
| Asn | Tyr | Asp | His | Ser | Leu | Val | Lys | Val | Leu | 320 |
| CTC | TCT | CAT | GGA | GCC | AAA | GAA | GAT | TTT | CAC | 990 |
| Leu | Ser | His | Gly | Ala | Lys | Glu | Asp | Phe | His | 330 |

TABLE 1-continued

Human 2-5A-depedent RNase
ID SEQ NO:1:, ID SEQ NO:2:, ID SEQ NO:3: and ID SEQ NO:4:

| CCT | CCT | GCT | GAA | GAC | TGG | AAG | CCT | CAG | AGC | 1020 |
| Pro | Pro | Ala | Glu | Asp | Trp | Lys | Pro | Gln | Ser | 340 |
| TCA | CAC | TGG | GGG | GCA | GCC | CTG | AAG | GAT | CTC | 1050 |
| Ser | His | Trp | Gly | Ala | Ala | Leu | Lys | Asp | Leu | 350 |
| CAC | AGA | ATA | TAC | CGC | CCT | ATG | ATT | GGC | AAA | 1080 |
| His | Arg | Ile | Tyr | Arg | Pro | Met | Ile | Gly | Lys | 360 |
| CTC | AAG | TTC | TTT | ATT | GAT | GAA | AAA | TAC | AAA | 1110 |
| Leu | Lys | Phe | Phe | Ile | Asp | Glu | Lys | Tyr | Lys | 370 |
| ATT | GCT | GAT | ACT | TCA | GAA | GGA | GGC | ATC | TAC | 1140 |
| Ile | Ala | Asp | Thr | Ser | Glu | Gly | Gly | Ile | Tyr | 380 |
| CTG | GGG | TTC | TAT | GAG | AAG | CAA | GAA | GTA | GCT | 1170 |
| Leu | Gly | Phe | Tyr | Glu | Lys | Gln | Glu | Val | Ala | 390 |
| GTG | AAG | ACG | TTC | TGT | GAG | GGC | AGC | CCA | CGT | 1200 |
| Val | Lys | Thr | Phe | Cys | Glu | Gly | Ser | Pro | Arg | 400 |
| GCA | CAG | CGG | GAA | GTC | TCT | TGT | CTG | CAA | AGC | 1230 |
| Ala | Gln | Arg | Glu | Val | Ser | Cys | Leu | Gln | Ser | 410 |
| AGC | CGA | GAG | AAC | AGT | CAC | TTG | GTG | ACA | TTC | 1260 |
| Ser | Arg | Glu | Asn | Ser | His | Leu | Val | Thr | Phe | 420 |
| TAT | GGG | AGT | GAG | AGC | CAC | AGG | GGC | CAC | TTG | 1290 |
| Tyr | Gly | Ser | Glu | Ser | His | Arg | Gly | His | Leu | 430 |
| TTT | GTG | TGT | GTC | ACC | CTC | TGT | GAG | CAG | ACT | 1320 |
| Phe | Val | Cys | Val | Thr | Leu | Cys | Glu | Gln | Thr | 440 |
| CTG | GAA | GCG | TGT | TTG | GAT | GTG | CAC | AGA | GGG | 1350 |
| Leu | Glu | Ala | Cys | Leu | Asp | Val | His | Arg | Gly | 450 |
| GAA | GAT | GTG | GAA | AAT | GAG | GAA | GAT | GAA | TTT | 1380 |
| Glu | Asp | Val | Glu | Asn | Glu | Glu | Asp | Glu | Phe | 460 |
| GCC | CGA | AAT | GTC | CTG | TCA | TCT | ATA | TTT | AAG | 1410 |
| Ala | Arg | Asn | Val | Leu | Ser | Ser | Ile | Phe | Lys | 470 |
| GCT | GTT | CAA | GAA | CTA | CAC | TTG | TCC | TGT | GGA | 1440 |
| Ala | Val | Gln | Glu | Leu | His | Leu | Ser | Cys | Gly | 480 |
| TAC | ACC | CAC | CAG | GAT | CTG | CAA | CCA | CAA | AAC | 1470 |
| Tyr | Thr | His | Gln | Asp | Leu | Gln | Pro | Gln | Asn | 490 |
| ATC | TTA | ATA | GAT | TCT | AAG | AAA | GCT | GCT | CAC | 1500 |
| Ile | Leu | Ile | Asp | Ser | Lys | Lys | Ala | Ala | His | 500 |
| CTG | GCA | GAT | TTT | GAT | AAG | AGC | ATC | AAG | TGG | 1530 |
| Leu | Ala | Asp | Phe | Asp | Lys | Ser | Ile | Lys | Trp | 510 |
| GCT | GGA | GAT | CCA | CAG | GAA | GTC | AAG | AGA | GAT | 1560 |
| Ala | Gly | Asp | Pro | Gln | Glu | Val | Lys | Arg | Asp | 520 |
| CTA | GAG | GAC | CTT | GGA | CGG | CTG | GTC | CTC | TAT | 1590 |
| Leu | Glu | Asp | Leu | Gly | Arg | Leu | Val | Leu | Tyr | 530 |
| GTG | GTA | AAG | AAG | GGA | AGC | ATC | TCA | TTT | GAG | 1620 |
| Val | Val | Lys | Lys | Gly | Ser | Ile | Ser | Phe | Glu | 540 |
| GAT | CTG | AAA | GCT | CAA | AGT | AAT | GAA | GAG | GTG | 1650 |
| Asp | Leu | Lys | Ala | Gln | Ser | Asn | Glu | Glu | Val | 550 |
| GTT | CAA | CTT | TCT | CCA | GAT | GAG | GAA | ACT | AAG | 1680 |
| Val | Gln | Leu | Ser | Pro | Asp | Glu | Glu | Thr | Lys | 560 |
| GAC | CTC | ATT | CAT | CGT | CTC | TTC | CAT | CCT | GGG | 1710 |
| Asp | Leu | Ile | His | Arg | Leu | Phe | His | Pro | Gly | 570 |
| GAA | CAT | GTG | AGG | GAC | TGT | CTG | AGT | GAC | CTG | 1740 |
| Glu | His | Val | Arg | Asp | Cys | Leu | Ser | Asp | Leu | 580 |

TABLE 1-continued

Human 2-5A-depedent RNase
ID SEQ NO:1:, ID SEQ NO:2:, ID SEQ NO:3: and ID SEQ NO:4:

| | | | | | | | | | | |
|---|---|---|---|---|---|---|---|---|---|---|
| CTG | GGT | CAT | CCC | TTC | TTT | TGG | ACT | TGG | GAG | 1770 |
| Leu | Gly | His | Pro | Phe | Phe | Trp | Thr | Trp | Glu | 590 |
| AGC | CGC | TAT | AGG | ACG | CTT | CGG | AAT | GTG | GGA | 1800 |
| Ser | Arg | Tyr | Arg | Thr | Leu | Arg | Asn | Val | Gly | 600 |
| AAT | GAA | TCC | GAC | ATC | AAA | ACA | CGA | AAA | TCT | 1830 |
| Asn | Glu | Ser | Asp | Ile | Lys | Thr | Arg | Lys | Ser | 610 |
| GAA | AGT | GAG | ATC | CTC | AGA | CTA | CTG | CAA | CCT | 1860 |
| Glu | Ser | Glu | Ile | Leu | Arg | Leu | Leu | Gln | Pro | 620 |
| GGG | CCT | TCT | GAA | CAT | TCC | AAA | AGT | TTT | GAC | 1890 |
| Gly | Pro | Ser | Glu | His | Ser | Lys | Ser | Phe | Asp | 630 |
| AAG | TGG | ACG | ACT | AAG | ATT | AAT | GAA | TGT | GTT | 1920 |
| Lys | Trp | Thr | Thr | Lys | Ile | Asn | Glu | Cys | Val | 640 |
| ATG | AAA | AAA | ATG | AAT | AAG | TTT | TAT | GAA | AAA | 1950 |
| Met | Lys | Lys | Met | Asn | Lys | Phe | Tyr | Glu | Lys | 650 |
| AGA | GGC | AAT | TTC | TAC | CAG | AAC | ACT | GTG | GGT | 1980 |
| Arg | Gly | Asn | Phe | Tyr | Gln | Asn | Thr | Val | Gly | 660 |
| GAT | CTG | CTA | AAG | TTC | ATC | CGG | AAT | TTG | GGA | 1210 |
| Asp | Leu | Leu | Lys | Phe | Ile | Arg | Asn | Leu | Gly | 670 |
| GAA | CAC | ATT | GAT | GAA | GAA | AAG | CAT | AAA | AAG | 2040 |
| Glu | His | Ile | Asp | Glu | Glu | Lys | His | Lys | Lys | 680 |
| ATG | AAA | TTA | AAA | ATT | GGA | GAC | CCT | TCC | CTG | 2070 |
| Met | Lys | Leu | Lys | Ile | Gly | Asp | Pro | Ser | Leu | 690 |
| TAT | TTT | CAG | AAG | ACA | TTT | CCA | GAT | CTG | GTG | 2100 |
| Tyr | Phe | Gln | Lys | Thr | Phe | Pro | Asp | Leu | Val | 700 |
| ATC | TAT | GTC | TAC | ACA | AAA | CTA | CAG | AAC | ACA | 2130 |
| Ile | Tyr | Val | Tyr | Thr | Lys | Leu | Gln | Asn | Thr | 710 |
| GAA | TAT | AGA | AAG | CAT | TTC | CCC | CAA | ACC | CAC | 2160 |
| Glu | Tyr | Arg | Lys | His | Phe | Pro | Gln | Thr | His | 720 |
| AGT | CCA | AAC | AAA | CCT | CAG | TGT | GAT | GGA | GCT | 2190 |
| Ser | Pro | Asn | Lys | Pro | Gln | Cys | Asp | Gly | Ala | 730 |
| GGT | GGG | GCC | AGT | GGG | TTG | GCC | AGC | CCT | GGG | 2220 |
| Gly | Gly | Ala | Ser | Gly | Leu | Ala | Ser | Pro | Gly | 740 |
| TGC | 2223 | | | t gat ggact gat t t gct ggagt t cagggaact act | | | | | | 2258 |
| Cys | 741 | | | | | | | | | |

| | |
|---|---|
| t at t agct gt agagt cct t ggcaaat cacaacat | 2292 |
| t ct gggcct t t t aact caccaggt t gct t gt gagggat | 2330 |
| gagt t gcat agct gat at gt cagt ccct ggcat cgt g | 2367 |
| t at t ccat at gt ct at aacaaaagcaat at at acccag | 2405 |
| act acact agt ccat aagct t t acccact aact ggga | 2442 |
| ggacat t ct gct aagat t cct t t t gt caat t gcaccaa | 2480 |
| aagaat gagt gcct t gacccct aat gct gcat at gt t | 2517 |
| acaat t ct ct cact t aat t t t cccaat gat ct t gcaaa | 2555 |
| acagggat t at cat ccccat t t aagaact gaggaacc | 2592 |
| t gagact cagagagt gt gagct act ggcccaagat t at | 2630 |
| t caat t t at acct agcact t t at aaat t t at gt ggt g | 2667 |
| t t at t ggt acct ct cat t t gggcacct t aaaact t aac | 2705 |
| t at ct t ccaggget ct t ccagat gaggcccaaaacat | 2742 |
| at at aggggt t ccaggaat ct cat t cat t cat t cagt a | 2780 |
| t t t at t gagcat ct agt at aagt ct gggcact ggat g | 2817 |
| cat gaat t | 2825 |

*It is believed that the original codon number 95, i.e. CTT encoding the amino acid number 95, i.e. leucine, is correct, however the alternative codon in parenthesis shown above codon number 95, i.e. CCT encoding the alternative ainino acid in parenthesis shown below amino acid number 95, i.e. proline may also exist at this position (see page 81).

SEQ ID NO:1: represents the DNA encoding sequence for the human 2-5A-dependent RNase protein. SEQ ID NO:2: represents the amino acid sequence encoded by the DNA sequence designated SEQ ID NO:1:. SEQ ID NO:3: represents the DNA sequence, represented by SEQ ID NO:1:, having the alternative codon number 95, CCT. SEQ ID NO:4: represents the amino acid sequence encoded by SEQ ID NO:3:, having the alternative amino acid number 95, proline.

TABLE 2

Murine 2-5A-dependent RNase (partial)
SEQ ID NO:5 and SEQ ID NO:6:

−163
at t cggcacgaggaaggt gccaat t act agct ccct t ct t t at t cgt gt a ct gat gagat gt cagaagacagaacat aat cagcccaat ccct act ccaa gact ct cat t gt gt cccaaagaaacacacgt gt gcat t t cccaaggaaaa

| ggcat t gaggacc | | | | ATG | GAG | ACC | CCG | GAT | TAT | 18 |
|---|---|---|---|---|---|---|---|---|---|---|
| | | | | Met | Glu | Thr | Pro | Asp | Tyr | 6 |
| AAC | ACA | CCT | CAG | GGT | GGA | ACC | CCA | TCA | GCG | 48 |
| Asn | Thr | Pro | Gln | Gly | Gly | Thr | Pro | Ser | Ala | 16 |
| GGA | AGT | CAG | AGG | ACC | GTT | GTC | GAA | GAT | GAT | 78 |
| Gly | Ser | Gln | Arg | Thr | Val | Val | Glu | Asp | Asp | 26 |
| TCT | TCG | TTG | ATC | AAA | GCT | GTT | CAG | AAG | GGA | 108 |
| Ser | Ser | Leu | Ile | Lys | Ala | Val | Gln | Lys | Gly | 36 |
| GAT | GTT | GTC | AGG | GTC | CAG | CAA | TTG | TTA | GAA | 138 |
| Asp | Val | Val | Arg | Val | Gln | Gln | Leu | Leu | Glu | 46 |
| AAA | GGG | GCT | GAT | GCC | AAT | GCC | TGT | GAA | GAC | 168 |
| Lys | Gly | Ala | Asp | Ala | Asn | Ala | Cys | Glu | Asp | 56 |
| ACC | TGG | GGC | TGG | ACA | CCT | TTG | CAC | AAC | GCA | 198 |
| Thr | Trp | Gly | Trp | Thr | Pro | Leu | His | Asn | Ala | 66 |
| GTG | CAA | GCT | GGC | AGG | GTA | GAC | ATT | GTG | AAC | 228 |
| Val | Gln | Ala | Gly | Arg | Val | Asp | Ile | Val | Asn | 76 |
| CTC | CTG | CTT | AGT | CAT | GGT | GCT | GAC | CCT | CAT | 258 |
| Leu | Leu | Leu | Ser | His | Gly | Ala | Asp | Pro | His | 86 |
| CGG | AGG | AAG | AAG | AAT | GGG | GCC | ACC | CCC | TTC | 288 |
| Arg | Arg | Lys | Lys | Asn | Gly | Ala | Thr | Pro | Phe | 96 |
| ATC | ATT | GCT | GGG | ATC | CAG | GGA | GAT | GTG | AAA | 318 |
| Ile | Ile | Ala | Gly | Ile | Gln | Gly | Asp | Val | Lys | 106 |
| CTG | CTC | GAG | ATT | CTC | CTC | TCT | TGT | GGT | GCA | 348 |
| Leu | Leu | Glu | Ile | Leu | Leu | Ser | Cys | Gly | Ala | 116 |
| GAC | GTC | AAT | GAG | TGT | GAC | GAG | AAC | GGA | TTC | 378 |
| Asp | Val | Asn | Glu | Cys | Asp | Glu | Asn | Gly | Phe | 126 |
| ACG | GCT | TTC | ATG | GAA | GCT | GCT | GAG | CGT | GGT | 408 |
| Thr | Ala | Phe | Met | Glu | Ala | Ala | Glu | Arg | Gly | 136 |
| AAC | GCT | GAA | GCC | TTA | AGA | TTC | CTT | TTT | GCT | 438 |
| Asn | Ala | Glu | Ala | Leu | Arg | Phe | Leu | Phe | Ala | 146 |
| AAG | GGA | GCC | AAT | GTG | AAT | TTG | CGA | CGA | CAG | 468 |
| Lys | Gly | Ala | Asn | Val | Asn | Leu | Arg | Arg | Gln | 156 |
| ACA | ACG | AAG | GAC | AAA | AGG | CGA | TTG | AAG | CAA | 498 |
| Thr | Thr | Lys | Asp | Lys | Arg | Arg | Leu | Lys | Gln | 166 |
| GGA | GGC | GCC | ACA | GCT | CTC | ATG | AGC | GCT | GCT | 528 |
| Gly | Gly | Ala | Thr | Ala | Leu | Met | Ser | Ala | Ala | 176 |
| GAG | AAG | GGC | CAC | CTG | GAA | GTC | CTG | AGA | ATT | 558 |
| Glu | Lys | Gly | His | Leu | Glu | Val | Leu | Arg | Ile | 186 |
| CTC | CTC | AAT | GAC | ATG | AAG | GCA | GAA | GTC | GAT | 588 |
| Leu | Leu | Asn | Asp | Met | Lys | Ala | Glu | Val | Asp | 196 |
| GCT | CGG | GAC | AAC | ATG | GGC | AGA | AAT | GCC | CTG | 618 |
| Ala | Arg | Asp | Asn | Met | Gly | Arg | Asn | Ala | Leu | 206 |
| ATC | CGT | ACT | CTG | CTG | AAC | TGG | GAT | TGT | GAA | 648 |

TABLE 2-continued

Murine 2-5A-dependent RNase (partial)
SEQ ID NO:5 and SEQ ID NO:6:

| Ile | Arg | Thr | Leu | Leu | Asn | Trp | Asp | Cys | Glu | 216 |
|---|---|---|---|---|---|---|---|---|---|---|
| AAT | GTG | GAG | GAG | ATT | ACT | TCA | ATC | CTG | ATT | 678 |
| Asn | Val | Glu | Glu | Ile | Thr | Ser | Ile | Leu | Ile | 226 |
| CAG | CAC | GGG | GCT | GAT | GTT | AAC | GTG | AGA | GGA | 708 |
| Gln | His | Gly | Ala | Asp | Val | Asn | Val | Arg | Gly | 236 |
| GAA | AGA | GGG | AAA | ACA | CCC | CTC | ATC | GCA | GCA | 738 |
| Glu | Arg | Gly | Lys | Thr | Pro | Leu | Ile | Ala | Ala | 246 |
| GTG | GAG | AGG | AAG | CAC | ACA | GGC | TTG | GTG | CAG | 768 |
| Val | Glu | Arg | Lys | His | Thr | Gly | Leu | Val | Gln | 256 |
| ATG | CTC | CTG | AGT | CGG | GAA | GGC | ATA | AAC | ATA | 798 |
| Met | Leu | Leu | Ser | Arg | Glu | Gly | Ile | Asn | Ile | 266 |
| GAT | GCC | AGG | GAT | AAC | GAG | GGC | AAG | ACA | GCT | 828 |
| Asp | Ala | Arg | Asp | Asn | Glu | Gly | Lys | Thr | Ala | 276 |
| CTG | CTA | ATT | GCT | GTT | GAT | AAA | CAA | CTG | AAG | 858 |
| Leu | Leu | Ile | Ala | Val | Asp | Lys | Gln | Leu | Lys | 286 |
| GAA | ATT | GTC | CAG | TTG | CTT | CTT | GAA | AAG | GGA | 888 |
| Glu | Ile | Val | Gln | Leu | Leu | Leu | Glu | Lys | Gly | 296 |
| GCT | GAT | AAG | TGT | GAC | GAT | CTT | GTT | TGG | ATA | 918 |
| Ala | Asp | Lys | Cys | Asp | Asp | Leu | Val | Trp | Ile | 306 |
| GCC | AGG | AGG | AAT | CAT | GAC | TAT | CAC | CTT | GTA | 948 |
| Ala | Arg | Arg | Asn | His | Asp | Tyr | His | Leu | Val | 316 |
| AAG | CTT | CTC | CTC | CCT | TAT | GTA | GCT | AAT | CCT | 978 |
| Lys | Leu | Leu | Leu | Pro | Tyr | Val | Ala | Asn | Pro | 326 |
| GAC | ACC | GAC | CCT | CCT | GCT | GGA | GAC | TGG | TCG | 1008 |
| Asp | Thr | Asp | Pro | Pro | Ala | Gly | Asp | Trp | Ser | 336 |
| CCT | CAC | AGT | TCA | CGT | TGG | GGG | ACA | GCC | TTG | 1038 |
| Pro | His | Ser | Ser | Arg | Trp | Gly | Thr | Ala | Leu | 346 |
| AAA | AGC | CTC | CAC | AGT | ATG | ACT | CGA | CCC | ATG | 1068 |
| Lys | Ser | Leu | His | Ser | Met | Thr | Arg | Pro | Met | 356 |
| ATT | GGC | AAA | CTC | AAG | ATC | TTC | ATT | CAT | GAT | 1098 |
| Ile | Gly | Lys | Leu | Lys | Ile | Phe | Ile | His | Asp | 366 |
| GAC | TAT | AAA | ATT | GCT | GGC | ACT | TCC | GAA | GGG | 1128 |
| Asp | Tyr | Lys | Ile | Ala | Gly | Thr | Ser | Glu | Gly | 376 |
| GCT | GTC | TAC | CTA | GGG | ATC | TAT | GAC | AAT | CGA | 1158 |
| Ala | Val | Tyr | Leu | Gly | Ile | Tyr | Asp | Asn | Arg | 386 |
| GAA | GTG | GCT | GTG | AAG | GTC | TTC | CGT | GAG | AAT | 1188 |
| Glu | Val | Ala | Val | Lys | Val | Phe | Arg | Glu | Asn | 396 |
| AGC | CCA | CGT | GGA | TGT | AAG | GAA | GTC | TCT | TGT | 1218 |
| Ser | Pro | Arg | Gly | Cys | Lys | Glu | Val | Ser | Cys | 406 |
| CTG | CGG | GAC | TGC | GGT | GAC | CAC | AGT | AAC | TTA | 1248 |
| Leu | Arg | Asp | Cys | Gly | Asp | His | Ser | Asn | Leu | 416 |
| GTG | GCT | TTC | TAT | GGA | AGA | GAG | GAC | GAT | AAG | 1278 |
| Val | Ala | Phe | Tyr | Gly | Arg | Glu | Asp | Asp | Lys | 426 |
| GGC | TGT | TTA | TAT | GTG | TGT | GTG | TCC | CTG | TGT | 1308 |
| Gly | Cys | Leu | Tyr | Val | Cys | Val | Ser | Leu | Cys | 436 |
| GAG | TGG | ACA | CTG | GAA | GAG | TTC | CTG | AGG | TTG | 1338 |
| Glu | Trp | Thr | Leu | Glu | Glu | Phe | Leu | Arg | Leu | 446 |

TABLE 2-continued

Murine 2-5A-dependent RNase (partial)
SEQ ID NO:5 and SEQ ID NO:6:

| | | | | | | | | | |
|---|---|---|---|---|---|---|---|---|---|
| CCC | AGA | GAG | GAA | CCT | GTG | GAG | AAC | GGG | GAA | 1368 |
| Pro | Arg | Glu | Glu | Pro | Val | Glu | Asn | Gly | Glu | 456 |
| GAT | AAG | TTT | GCC | CAC | AGC | ATC | CTA | TTA | TCT | 1398 |
| Asp | Lys | Phe | Ala | His | Ser | Ile | Leu | Leu | Ser | 466 |
| ATA | TTT | GAG | GGT | GTT | CAA | AAA | CTA | CAC | TTG | 1428 |
| Ile | Phe | Glu | Gly | Val | Gln | Lys | Leu | His | Leu | 476 |
| CAT | GGA | TAT | TCC | CAT | CAG | GAC | CTG | CAA | CCA | 1458 |
| His | Gly | Tyr | Ser | His | Gln | Asp | Leu | Gln | Pro | 486 |
| CAA | AAC | ATC | TTA | ATA | GAT | TCC | AAG | AAA | GCT | 1488 |
| Gln | Asn | Ile | Leu | Ile | Asp | Ser | Lys | Lys | Ala | 496 |
| GTC | CGG | CTG | GCA | GAT | TTT | GAT | CAG | AGC | ATC | 1518 |
| Val | Arg | Leu | Ala | Asp | Phe | Asp | Gln | Ser | Ile | 506 |
| CGA | TGG | ATG | GGA | GAG | TCA | CAG | ATG | GTC | AGG | 1548 |
| Arg | Trp | Met | Gly | Glu | Ser | Gln | Met | Val | Arg | 516 |
| AGA | GAC | TTG | GAG | GAT | CTT | GGA | CGG | CTG | GTT | 1578 |
| Arg | Asp | Leu | Glu | Asp | Leu | Gly | Arg | Leu | Val | 526 |
| CTC | TAC | GTG | GTA | ATG | AAA | GGT | GAG | ATC | CCC | 1608 |
| Leu | Tyr | Val | Val | Met | Lys | Gly | Glu | Ile | Pro | 536 |
| TTT | GAG | ACA | CTA | AAG | ACT | CAG | AAT | GAT | GAA | 1638 |
| Phe | Glu | Thr | Leu | Lys | Thr | Gln | Asn | Asp | Glu | 546 |
| GTG | CTG | CTT | ACA | ATG | TCT | CCA | GAT | GAG | GAG | 1668 |
| Val | Leu | Leu | Thr | Met | Ser | Pro | Asp | Glu | Glu | 556 |
| ACT | AAG | GAC | CTC | ATT | CAT | TGC | CTG | TTT | TCT | 1698 |
| Thr | Lys | Asp | Leu | Ile | His | Cyc | Leu | Phe | Ser | 566 |
| CCT | GGA | GAA | AAT | GTC | AAG | AAC | TGC | CTG | GTA | 1728 |
| Pro | Gly | Glu | Asn | Val | Lys | Asn | Cys | Leu | Val | 576 |
| GAC | CTG | CTT | GGC | CAT | CCT | TTC | TTT | TGG | ACT | 1758 |
| Asp | Leu | Leu | Gly | His | Pro | Phe | Phe | Trp | Thr | 586 |
| TGG | GAG | AAC | CGC | TAT | AGA | ACA | CTC | CGG | AAT | 1788 |
| Trp | Glu | Asn | Arg | Tyr | Arg | Thr | Leu | Arg | Asn | 596 |
| GTG | GGA | AAT | GAA | TCT | GAC | ATC | AAA | GTA | CGG | 1818 |
| Val | Gly | Asn | Glu | Ser | Asp | Ile | Lys | Val | Arg | 606 |
| AAA | TGT | AAA | AGT | GAT | CTT | CTC | AGA | CTA | CTG | 1848 |
| Lys | Cys | Lys | Ser | Asp | Leu | Leu | Arg | Leu | Leu | 616 |
| CAG | CAT | CAG | ACA | CTT | GAG | CCT | CCC | AGA | AGC | 1878 |
| Gln | His | Gln | Thr | Leu | Glu | Pro | Pro | Arg | Ser | 626 |
| TTT | GAC | CAG | TGG | ACA | TCT | AAG | ATC | GAC | AAA | 1908 |
| Phe | Asp | Gln | Trp | Thr | Ser | Lys | Ile | Asp | Lys | 636 |
| AAT | GTT | ATG | GAT | GAA | ATG | AAT | CAT | TTC | TAC | 1938 |
| Asn | Val | Met | Asp | Glu | Met | Asn | His | Phe | Tyr | 646 |
| GAA | AAG | AGA | AAA | AAA | AAC | CCT | TAT | CAG | GAT | 1968 |
| Glu | Lys | Arg | Lys | Lys | Asn | Pro | Tyr | Gln | Asp | 656 |
| ACT | GTA | GGT | GAT | CTG | CTG | AAG | TTT | ATT | CGG | 1998 |
| Thr | Val | Gly | Asp | Leu | Leu | Lys | Phe | Ile | Arg | 666 |
| AAT | ATA | GGC | GAA | CAC | ATC | AAT | GAG | GAA | AAA | 2028 |
| Asn | Ile | Gly | Glu | His | Ile | Asn | Glu | Glu | Lys | 676 |
| AAG | CGG | GGG | | | | | | | 2037 |
| Lys | Arg | Gly | | | | | | | 679 |

SEQ ID NO:5: represents the DNA sequence encoding Murine 2-5A-dependent RNase (partial). SEQ ID NO:6: represents the amino acid sequence encoded by SEQ ID NO:5.

The present invention may, of course, be carried out in other specific ways than those herein set forth without departing from the spirit and essential characteristics of the invention. For example, the nucleotide sequences disclosed herein may be combined with other nucleotide sequences to generate heterologous nucleotide sequences for introduction into the genomes of plants to form transgenic plants. The present embodiments are, therefore, to be considered in all respects as illustrative and not restrictive and all changes coming within the meaning and equivalency range of the appended claims are intended to be embraced herein.

We claim:

1. A plant transformation vector which comprises a nucleotide sequence which encodes an amino acid sequence having 2-5A-dependent RNase activity.

2. A plant transformation vector of claim 1, said nucleotide sequence comprising the nucleotide sequence identified as SEQ ID NO:1 or SEQ ID NO:3 or any fragment thereof having 2-5A-dependent RNase activity.

3. A plant transformation vector of claim 1, said nucleotide sequence comprising nucleotides selected from the group consisting of nucleotides designated as 1-2037, 1-1968, 1-1858, 1-1546, 1-1422, 1-1210, 1-1095, 1-1028 and 1-884 in SEQ ID NO:5.

4. A plant transformation vector of claim 1, said vector being plasmid pAM943:2-5A-dep. RNase sense.

5. A plant cell containing said plant transformation vector of claim 1.

6. A plant cell of claim 5, said plant transformation vector being plasmid pAM943:2-5A-dep. RNase sense.

7. A plant cell of claim 5, said plant cell being a tobacco plant cell.

8. A bacterial cell containing said plant transformation vector of claim 1.

9. A bacterial cell of claim 8, said bacterial cell being an *Agrobacterium tumefaciens* bacterial cell.

10. An isolated nucleotide sequence having human 2-5A-dependent RNase activity, said nucleotide sequence being identified as SEQ ID NO:3 and comprising:

| | | | | | | | | | | | | | | | |
|---|---|---|---|---|---|---|---|---|---|---|---|---|---|---|---|
| ATG | GAG | AGC | AGG | GAT | CAT | AAC | AAC | CCC | CAG | GAG | GGA | CCC | ACG | TCC | 45 |
| TCC | AGC | GGT | AGA | AGG | GCT | GCA | GTG | GAA | GAC | AAT | CAC | TTG | CTG | ATT | 90 |
| AAA | GCT | GTT | CAA | AAC | GAA | GAT | GTT | GAC | CTG | GTC | CAG | CAA | TTG | CTG | 135 |
| GAA | GGT | GGA | GCC | AAT | GTT | AAT | TTC | CAG | GAA | GAG | GAA | GGG | GGC | TGG | 180 |
| ACA | CCT | CTG | CAT | AAC | GCA | GTA | CAA | ATG | AGC | AGG | GAG | GAC | ATT | GTG | 225 |
| GAA | CTT | CTG | CTT | CGT | CAT | GGT | GCT | GAC | CCT | GTT | CTG | AGG | AAG | AAG | 270 |
| AAT | GGG | GCC | ACG | CCT | TTT | ATC | CTC | GCA | GCG | ATT | GCG | GGG | AGC | GTG | 315 |
| AAG | CTG | CTG | AAA | CTT | TTC | CTT | TCT | AAA | GGA | GCA | GAT | GTC | AAT | GAG | 360 |
| TGT | GAT | TTT | TAT | GGC | TTC | ACA | GCC | TTC | ATG | GAA | GCC | GCT | GTG | TAT | 405 |
| GGT | AAG | GTC | AAA | GCC | CTA | AAA | TTC | CTT | TAT | AAG | AGA | GGA | GCA | AAT | 450 |
| GTG | AAT | TTG | AGG | CGA | AAG | ACA | AAG | GAG | GAT | CAA | GAG | CGG | CTG | AGG | 495 |
| AAA | GGA | GGG | GCC | ACA | GCT | CTC | ATG | GAC | GCT | GCT | GAA | AAA | GGA | CAC | 540 |
| GTA | GAG | GTC | TTG | AAG | ATT | CTC | CTT | GAT | GAG | ATG | GGG | GCA | GAT | GTA | 585 |
| AAC | GCC | TGT | GAC | AAT | ATG | GGC | AGA | AAT | GCC | TTG | ATC | CAT | GCT | CTC | 630 |
| CTG | AGC | TCT | GAC | GAT | AGT | GAT | GTG | GAG | GCT | ATT | ACG | CAT | CTG | CTG | 675 |
| CTG | GAC | CAT | GGG | GCT | GAT | GTC | AAT | GTG | AGG | GGA | GAA | AGA | GGG | AAG | 720 |

```
ACT CCC CTG ATC CTG GCA GTG GAG AAG AAG CAC TTG GGT TTG GTG      765
CAG AGG CTT CTG GAG CAA GAG CAC ATA GAG ATT AAT GAC ACA GAC      810
AGT GAT GGC AAA ACA GCA CTG CTG CTT GCT GTT GAA CTC AAA CTG      855
AAG AAA ATC GCC GAG TTG CTG TGC AAA CGT GGA GCC AGT ACA GAT      900
TGT GGG GAT CTT GTT ATG ACA GCG AGG CGG AAT TAT GAC CAT TCC      945
CTT GTG AAG GTT CTT CTC TCT CAT GGA GCC AAA GAA GAT TTT CAC      990
CCT CCT GCT GAA GAC TGG AAG CCT CAG AGC TCA CAC TGG GGG GCA     1035
GCC CTG AAG GAT CTC CAC AGA ATA TAC CGC CCT ATG ATT GGC AAA     1080
CTC AAG TTC TTT ATT GAT GAA AAA TAC AAA ATT GCT GAT ACT TCA     1125
GAA GGA GGC ATC TAC CTG GGG TTC TAT GAG AAG CAA GAA GTA GCT     1170
GYH AAG ACG TTC TGT GAG GGC AGC CCA CGT GCA CAG CGG GAA GTC     1215
TCT TGT CTG CAA AGC AGG CGA GAG AAC AGT CAC TTG GTG ACA TTC     1260
TAT GGG AGT GAG AGC CAC AGG GGC CAC TTG TTT GTG TGT GTC ACC     1305
CTC TGT GAG CAG ACT CTG GAA GCG TGT TTG GAT GTG CAC AGA GGG     1350
GAA GAT GTG GAA AAT GAG GAA GAT GAA TTT GCC CGA AAT GTC CTG     1395
TCA TCT ATA TTT AAG GCT GTT CAA GAA CTA CAC TTG TCC TGT GGA     1440
TAC ACC CAC CAG GAT CTG CAA CCA CAA AAC ATC TTA ATA GAT TCT     1485
AAG AAA GCT GCT CAC CTG GCA GAT TTT GAT AAG AGC ATC AAG TGG     1530
GCT GGA GAT CCA CAG GAA GTC AAG AGA GAT CTA GAG GAC CTT GGA     1575
CGG CTG GTC CTC TAT GTG GTA AAG AAG GGA AGC ATC TCA TTT GAG     1620
GAT CTG AAA GCT CAA AGT AAT GAA GAG GTG GTT CAA CTT TCT CCA     1665
GAT GAG GAA ACT AAG GAC CTC ATT CAT CGT CTC TTC CAT CCT GGG     1710
GAA CAT GTG AGG GAC TGT CTG AGT GAC CTG CTG GGT CAT CCC TTC     1755
TTT TGG ACT TGG GAG AGC CGC TAT AGG ACG CTT CGG AAT GTG GGA     1800
AAT GAA TCC GAC ATC AAA ACA CGA AAA TCT GAA AGT GAG ATC CTC     1845
AGA CTA CTG CAA CCT GGG CCT TCT GAA CAT TCC AAA AGT TTT GAC     1890
AAG TGG ACG ACT AAG ATT AAT GAA TGT GTT ATG AAA AAA ATG AAT     1935
AAG TTT TAT GAA AAA AGA GGC AAT TTC TAC CAG AAC ACT GTG GGT     1980
GAT CTG CTA AAG TTC ATC CGG AAT TTG GGA GAA CAC ATT GAT GAA     2025
GAA AAG CAT AAA AAG ATG AAA TTA AAA ATT GGA GAC CCT TCC CTG     2G70
TAT TTT CAG AAG ACA TTT CCA GAT CTG GTG ATC TAT GTC TAC ACA     2115
AAA CTA CAG AAC ACA GAA TAT AGA AAG CAT TTC CCC CAA ACC CAC     2160
AGT CCA AAC AAA CCT CAG TGT GAT GGA GCT GGT GGG GCC AGT GGG     2205
TTG GCC AGC CCT GGG TGC                                          2223
``` or a fragment thereof having 2-5A-dependent RNase activity.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2928 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 104..2326

( x i ) SEQUENCE DESCRIPTION: SEQ ID NO:1:

```
AATCCCAACT  TACACTCAAA  GCTTCTTTGA  TTAAGTGCTA  GGAGATAAAT  TTGCATTTTC          60

TCAAGGAAAA  GGCTAAAAGT  GGTAGCAGGT  GGCATTTACC  GTC ATG GAG AGC AGG            115
                                                  Met Glu Ser Arg
                                                   1

GAT CAT AAC AAC CCC CAG GAG GGA CCC ACG TCC TCC AGC GGT AGA AGG                163
Asp His Asn Asn Pro Gln Glu Gly Pro Thr Ser Ser Ser Gly Arg Arg
 5               10                  15                      20

GCT GCA GTG GAA GAC AAT CAC TTG CTG ATT AAA GCT GTT CAA AAC GAA                211
Ala Ala Val Glu Asp Asn His Leu Leu Ile Lys Ala Val Gln Asn Glu
                 25                  30                  35

GAT GTT GAC CTG GTC CAG CAA TTG CTG GAA GGT GGA GCC AAT GTT AAT                259
Asp Val Asp Leu Val Gln Gln Leu Leu Glu Gly Gly Ala Asn Val Asn
             40                  45                  50

TTC CAG GAA GAG GAA GGG GGC TGG ACA CCT CTG CAT AAC GCA GTA CAA                307
Phe Gln Glu Glu Glu Gly Gly Trp Thr Pro Leu His Asn Ala Val Gln
         55                  60                  65

ATG AGC AGG GAG GAC ATT GTG GAA CTT CTG CTT CGT CAT GGT GCT GAC                355
Met Ser Arg Glu Asp Ile Val Glu Leu Leu Leu Arg His Gly Ala Asp
     70                  75                  80

CCT GTT CTG AGG AAG AAG AAT GGG GCC ACG CTT TTT ATC CTC GCA GCG                403
Pro Val Leu Arg Lys Lys Asn Gly Ala Thr Leu Phe Ile Leu Ala Ala
 85                  90                  95                     100

ATT GCG GGG AGC GTG AAG CTG CTG AAA CTT TTC CTT TCT AAA GGA GCA                451
Ile Ala Gly Ser Val Lys Leu Leu Lys Leu Phe Leu Ser Lys Gly Ala
                    105                 110                 115

GAT GTC AAT GAG TGT GAT TTT TAT GGC TTC ACA GCC TTC ATG GAA GCC                499
Asp Val Asn Glu Cys Asp Phe Tyr Gly Phe Thr Ala Phe Met Glu Ala
                120                 125                 130

GCT GTG TAT GGT AAG GTC AAA GCC CTA AAA TTC CTT TAT AAG AGA GGA                547
Ala Val Tyr Gly Lys Val Lys Ala Leu Lys Phe Leu Tyr Lys Arg Gly
            135                 140                 145

GCA AAT GTG AAT TTG AGG CGA AAG ACA AAG GAG GAT CAA GAG CGG CTG                595
Ala Asn Val Asn Leu Arg Arg Lys Thr Lys Glu Asp Gln Glu Arg Leu
        150                 155                 160
```

| | | | | | | | | | | | | | | | | |
|---|---|---|---|---|---|---|---|---|---|---|---|---|---|---|---|---|
| AGG | AAA | GGA | GGG | GCC | ACA | GCT | CTC | ATG | GAC | GCT | GCT | GAA | AAA | GGA | CAC | 643 |
| Arg | Lys | Gly | Gly | Ala | Thr | Ala | Leu | Met | Asp | Ala | Ala | Glu | Lys | Gly | His | |
| 165 | | | | 170 | | | | | 175 | | | | | | 180 | |
| GTA | GAG | GTC | TTG | AAG | ATT | CTC | CTT | GAT | GAG | ATG | GGG | GCA | GAT | GTA | AAC | 691 |
| Val | Glu | Val | Leu | Lys | Ile | Leu | Leu | Asp | Glu | Met | Gly | Ala | Asp | Val | Asn | |
| | | | | 185 | | | | | 190 | | | | | 195 | | |
| GCC | TGT | GAC | AAT | ATG | GGC | AGA | AAT | GCC | TTG | ATC | CAT | GCT | CTC | CTG | AGC | 739 |
| Ala | Cys | Asp | Asn | Met | Gly | Arg | Asn | Ala | Leu | Ile | His | Ala | Leu | Leu | Ser | |
| | | | 200 | | | | | 205 | | | | | 210 | | | |
| TCT | GAC | GAT | AGT | GAT | GTG | GAG | GCT | ATT | ACG | CAT | CTG | CTG | CTG | GAC | CAT | 787 |
| Ser | Asp | Asp | Ser | Asp | Val | Glu | Ala | Ile | Thr | His | Leu | Leu | Leu | Asp | His | |
| | | | 215 | | | | | 220 | | | | | 225 | | | |
| GGG | GCT | GAT | GTC | AAT | GTG | AGG | GGA | GAA | AGA | GGG | AAG | ACT | CCC | CTG | ATC | 835 |
| Gly | Ala | Asp | Val | Asn | Val | Arg | Gly | Glu | Arg | Gly | Lys | Thr | Pro | Leu | Ile | |
| | 230 | | | | | 235 | | | | | 240 | | | | | |
| CTG | GCA | GTG | GAG | AAG | AAG | CAC | TTG | GGT | TTG | GTG | CAG | AGG | CTT | CTG | GAG | 883 |
| Leu | Ala | Val | Glu | Lys | Lys | His | Leu | Gly | Leu | Val | Gln | Arg | Leu | Leu | Glu | |
| 245 | | | | | 250 | | | | | 255 | | | | | 260 | |
| CAA | GAG | CAC | ATA | GAG | ATT | AAT | GAC | ACA | GAC | AGT | GAT | GGC | AAA | ACA | GCA | 931 |
| Gln | Glu | His | Ile | Glu | Ile | Asn | Asp | Thr | Asp | Ser | Asp | Gly | Lys | Thr | Ala | |
| | | | | 265 | | | | | 270 | | | | | 275 | | |
| CTG | CTG | CTT | GCT | GTT | GAA | CTC | AAA | CTG | AAG | AAA | ATC | GCC | GAG | TTG | CTG | 979 |
| Leu | Leu | Leu | Ala | Val | Glu | Leu | Lys | Leu | Lys | Lys | Ile | Ala | Glu | Leu | Leu | |
| | | | 280 | | | | | 285 | | | | | 290 | | | |
| TGC | AAA | CGT | GGA | GCC | AGT | ACA | GAT | TGT | GGG | GAT | CTT | GTT | ATG | ACA | GCG | 1027 |
| Cys | Lys | Arg | Gly | Ala | Ser | Thr | Asp | Cys | Gly | Asp | Leu | Val | Met | Thr | Ala | |
| | | 295 | | | | | 300 | | | | | 305 | | | | |
| AGG | CGG | AAT | TAT | GAC | CAT | TCC | CTT | GTG | AAG | GTT | CTT | CTC | TCT | CAT | GGA | 1075 |
| Arg | Arg | Asn | Tyr | Asp | His | Ser | Leu | Val | Lys | Val | Leu | Leu | Ser | His | Gly | |
| | 310 | | | | | 315 | | | | | 320 | | | | | |
| GCC | AAA | GAA | GAT | TTT | CAC | CCT | CCT | GCT | GAA | GAC | TGG | AAG | CCT | CAG | AGC | 1123 |
| Ala | Lys | Glu | Asp | Phe | His | Pro | Pro | Ala | Glu | Asp | Trp | Lys | Pro | Gln | Ser | |
| 325 | | | | | 330 | | | | | 335 | | | | | 340 | |
| TCA | CAC | TGG | GGG | GCA | GCC | CTG | AAG | GAT | CTC | CAC | AGA | ATA | TAC | CGC | CCT | 1171 |
| Ser | His | Trp | Gly | Ala | Ala | Leu | Lys | Asp | Leu | His | Arg | Ile | Tyr | Arg | Pro | |
| | | | | 345 | | | | | 350 | | | | | 355 | | |
| ATG | ATT | GGC | AAA | CTC | AAG | TTC | TTT | ATT | GAT | GAA | AAA | TAC | AAA | ATT | GCT | 1219 |
| Met | Ile | Gly | Lys | Leu | Lys | Phe | Phe | Ile | Asp | Glu | Lys | Tyr | Lys | Ile | Ala | |
| | | | 360 | | | | | 365 | | | | | 370 | | | |
| GAT | ACT | TCA | GAA | GGA | GGC | ATC | TAC | CTG | GGG | TTC | TAT | GAG | AAG | CAA | GAA | 1267 |
| Asp | Thr | Ser | Glu | Gly | Gly | Ile | Tyr | Leu | Gly | Phe | Tyr | Glu | Lys | Gln | Glu | |
| | | 375 | | | | | 380 | | | | | 385 | | | | |
| GTA | GCT | GTG | AAG | ACG | TTC | TGT | GAG | GGC | AGC | CCA | CGT | GCA | CAG | CGG | GAA | 1315 |
| Val | Ala | Val | Lys | Thr | Phe | Cys | Glu | Gly | Ser | Pro | Arg | Ala | Gln | Arg | Glu | |
| | 390 | | | | | 395 | | | | | 400 | | | | | |
| GTC | TCT | TGT | CTG | CAA | AGC | AGC | CGA | GAG | AAC | AGT | CAC | TTG | GTG | ACA | TTC | 1363 |
| Val | Ser | Cys | Leu | Gln | Ser | Ser | Arg | Glu | Asn | Ser | His | Leu | Val | Thr | Phe | |
| 405 | | | | | 410 | | | | | 415 | | | | | 420 | |
| TAT | GGG | AGT | GAG | AGC | CAC | AGG | GGC | CAC | TTG | TTT | GTG | TGT | GTC | ACC | CTC | 1411 |
| Tyr | Gly | Ser | Glu | Ser | His | Arg | Gly | His | Leu | Phe | Val | Cys | Val | Thr | Leu | |
| | | | | 425 | | | | | 430 | | | | | 435 | | |
| TGT | GAG | CAG | ACT | CTG | GAA | GCG | TGT | TTG | GAT | GTG | CAC | AGA | GGG | GAA | GAT | 1459 |
| Cys | Glu | Gln | Thr | Leu | Glu | Ala | Cys | Leu | Asp | Val | His | Arg | Gly | Glu | Asp | |
| | | | 440 | | | | | 445 | | | | | 450 | | | |
| GTG | GAA | AAT | GAG | GAA | GAT | GAA | TTT | GCC | CGA | AAT | GTC | CTG | TCA | TCT | ATA | 1507 |
| Val | Glu | Asn | Glu | Glu | Asp | Glu | Phe | Ala | Arg | Asn | Val | Leu | Ser | Ser | Ile | |
| | | | 455 | | | | | 460 | | | | | 465 | | | |
| TTT | AAG | GCT | GTT | CAA | GAA | CTA | CAC | TTG | TCC | TGT | GGA | TAC | ACC | CAC | CAG | 1555 |
| Phe | Lys | Ala | Val | Gln | Glu | Leu | His | Leu | Ser | Cys | Gly | Tyr | Thr | His | Gln | |
| | 470 | | | | | 475 | | | | | 480 | | | | | |

```
GAT CTG CAA CCA CAA AAC ATC TTA ATA GAT TCT AAG AAA GCT GCT CAC     1603
Asp Leu Gln Pro Gln Asn Ile Leu Ile Asp Ser Lys Lys Ala Ala His
485                 490                 495                 500

CTG GCA GAT TTT GAT AAG AGC ATC AAG TGG GCT GGA GAT CCA CAG GAA     1651
Leu Ala Asp Phe Asp Lys Ser Ile Lys Trp Ala Gly Asp Pro Gln Glu
                    505                 510                 515

GTC AAG AGA GAT CTA GAG GAC CTT GGA CGG CTG GTC CTC TAT GTG GTA     1699
Val Lys Arg Asp Leu Glu Asp Leu Gly Arg Leu Val Leu Tyr Val Val
                520                 525                 530

AAG AAG GGA AGC ATC TCA TTT GAG GAT CTG AAA GCT CAA AGT AAT GAA     1747
Lys Lys Gly Ser Ile Ser Phe Glu Asp Leu Lys Ala Gln Ser Asn Glu
            535                 540                 545

GAG GTG GTT CAA CTT TCT CCA GAT GAG GAA ACT AAG GAC CTC ATT CAT     1795
Glu Val Val Gln Leu Ser Pro Asp Glu Glu Thr Lys Asp Leu Ile His
550                 555                 560

CGT CTC TTC CAT CCT GGG GAA CAT GTG AGG GAC TGT CTG AGT GAC CTG     1843
Arg Leu Phe His Pro Gly Glu His Val Arg Asp Cys Leu Ser Asp Leu
565                 570                 575                 580

CTG GGT CAT CCC TTC TTT TGG ACT TGG GAG AGC CGC TAT AGG ACG CTT     1891
Leu Gly His Pro Phe Phe Trp Thr Trp Glu Ser Arg Tyr Arg Thr Leu
                585                 590                 595

CGG AAT GTG GGA AAT GAA TCC GAC ATC AAA ACA CGA AAA TCT GAA AGT     1939
Arg Asn Val Gly Asn Glu Ser Asp Ile Lys Thr Arg Lys Ser Glu Ser
                600                 605                 610

GAG ATC CTC AGA CTA CTG CAA CCT GGG CCT TCT GAA CAT TCC AAA AGT     1987
Glu Ile Leu Arg Leu Leu Gln Pro Gly Pro Ser Glu His Ser Lys Ser
            615                 620                 625

TTT GAC AAG TGG ACG ACT AAG ATT AAT GAA TGT GTT ATG AAA AAA ATG     2035
Phe Asp Lys Trp Thr Thr Lys Ile Asn Glu Cys Val Met Lys Lys Met
630                 635                 640

AAT AAG TTT TAT GAA AAA AGA GGC AAT TTC TAC CAG AAC ACT GTG GGT     2083
Asn Lys Phe Tyr Glu Lys Arg Gly Asn Phe Tyr Gln Asn Thr Val Gly
645                 650                 655                 660

GAT CTG CTA AAG TTC ATC CGG AAT TTG GGA GAA CAC ATT GAT GAA GAA     2131
Asp Leu Leu Lys Phe Ile Arg Asn Leu Gly Glu His Ile Asp Glu Glu
                665                 670                 675

AAG CAT AAA AAG ATG AAA TTA AAA ATT GGA GAC CCT TCC CTG TAT TTT     2179
Lys His Lys Lys Met Lys Leu Lys Ile Gly Asp Pro Ser Leu Tyr Phe
                680                 685                 690

CAG AAG ACA TTT CCA GAT CTG GTG ATC TAT GTC TAC ACA AAA CTA CAG     2227
Gln Lys Thr Phe Pro Asp Leu Val Ile Tyr Val Tyr Thr Lys Leu Gln
            695                 700                 705

AAC ACA GAA TAT AGA AAG CAT TTC CCC CAA ACC CAC AGT CCA AAC AAA     2275
Asn Thr Glu Tyr Arg Lys His Phe Pro Gln Thr His Ser Pro Asn Lys
            710                 715                 720

CCT CAG TGT GAT GGA GCT GGT GGG GCC AGT GGG TTG GCC AGC CCT GGG     2323
Pro Gln Cys Asp Gly Ala Gly Gly Ala Ser Gly Leu Ala Ser Pro Gly
725                 730                 735                 740

TGC TGATGGACTG ATTTGCTGGA GTTCAGGGAA CTACTTATTA GCTGTAGAGT          2376
Cys

CCTTGGCAAA TCACAACATT CTGGGCCTTT TAACTCACCA GGTTGCTTGT GAGGGATGAG    2436

TTGCATAGCT GATATGTCAG TCCCTGGCAT CGTGTATTCC ATATGTCTAT AACAAAAGCA    2496

ATATATACCC AGACTACACT AGTCCATAAG CTTTACCCAC TAACTGGGAG ACATTCTGC     2556

TAAGATTCCT TTTGTCAATT GCACCAAAAG AATGAGTGCC TTGACCCCTA ATGCTGCATA    2616

TGTTACAATT CTCTCACTTA ATTTTCCCAA TGATCTTGCA AAACAGGGAT TATCATCCCC    2676

ATTTAAGAAC TGAGGAACCT GAGACTCAGA GAGTGTGAGC TACTGGCCCA AGATTATTCA    2736
```

```
ATTTATACCT AGCACTTTAT AAATTTATGT GGTGTTATTG GTACCTCTCA TTTGGGCACC    2796

TTAAAACTTA ACTATCTTCC AGGGCTCTTC CAGATGAGGC CCAAAACATA TATAGGGGTT    2856

CCAGGAATCT CATTCATTCA TTCAGTATTT ATTGAGCATC TAGTATAAGT CTGGGCACTG    2916

GATGCATGAA TT                                                         2928
```

( 2 ) INFORMATION FOR SEQ ID NO:2:

( i ) SEQUENCE CHARACTERISTICS:
        ( A ) LENGTH: 741 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Ser Arg Asp His Asn Asn Pro Gln Glu Gly Pro Thr Ser Ser
 1               5                  10                  15

Ser Gly Arg Arg Ala Ala Val Glu Asp Asn His Leu Leu Ile Lys Ala
            20                  25                  30

Val Gln Asn Glu Asp Val Asp Leu Val Gln Gln Leu Leu Glu Gly Gly
            35                  40                  45

Ala Asn Val Asn Phe Gln Glu Glu Gly Gly Trp Thr Pro Leu His
    50                  55                  60

Asn Ala Val Gln Met Ser Arg Glu Asp Ile Val Glu Leu Leu Leu Arg
 65                  70                  75                  80

His Gly Ala Asp Pro Val Leu Arg Lys Lys Asn Gly Ala Thr Leu Phe
                85                  90                  95

Ile Leu Ala Ala Ile Ala Gly Ser Val Lys Leu Leu Lys Leu Phe Leu
                100                 105                 110

Ser Lys Gly Ala Asp Val Asn Glu Cys Asp Phe Tyr Gly Phe Thr Ala
                115                 120                 125

Phe Met Glu Ala Ala Val Tyr Gly Lys Val Lys Ala Leu Lys Phe Leu
        130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175

Glu Lys Gly His Val Glu Val Leu Lys Ile Leu Leu Asp Glu Met Gly
                180                 185                 190

Ala Asp Val Asn Ala Cys Asp Asn Met Gly Arg Asn Ala Leu Ile His
            195                 200                 205

Ala Leu Leu Ser Ser Asp Asp Ser Asp Val Glu Ala Ile Thr His Leu
    210                 215                 220

Leu Leu Asp His Gly Ala Asp Val Asn Val Arg Gly Glu Arg Gly Lys
225                 230                 235                 240

Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
                260                 265                 270

Gly Lys Thr Ala Leu Leu Leu Ala Val Glu Leu Lys Leu Lys Lys Ile
            275                 280                 285

Ala Glu Leu Leu Cys Lys Arg Gly Ala Ser Thr Asp Cys Gly Asp Leu
            290                 295                 300

Val Met Thr Ala Arg Arg Asn Tyr Asp His Ser Leu Val Lys Val Leu
305                 310                 315                 320
```

-continued

| | | | | | | | | | | | | | | |
|---|---|---|---|---|---|---|---|---|---|---|---|---|---|---|
| Leu | Ser | His | Gly | Ala | Lys | Glu | Asp | Phe | His | Pro | Pro | Ala | Glu | Asp | Trp |
| | | | | 325 | | | | | 330 | | | | | 335 |
| Lys | Pro | Gln | Ser | Ser | His | Trp | Gly | Ala | Ala | Leu | Lys | Asp | Leu | His | Arg |
| | | | 340 | | | | | 345 | | | | | 350 | | |
| Ile | Tyr | Arg | Pro | Met | Ile | Gly | Lys | Leu | Lys | Phe | Phe | Ile | Asp | Glu | Lys |
| | | 355 | | | | 360 | | | | | | 365 | | | |
| Tyr | Lys | Ile | Ala | Asp | Thr | Ser | Glu | Gly | Ile | Tyr | Leu | Gly | Phe | Tyr |
| 370 | | | | | 375 | | | | 380 | | | | | |
| Glu | Lys | Gln | Glu | Val | Ala | Val | Lys | Thr | Phe | Cys | Glu | Gly | Ser | Pro | Arg |
| 385 | | | | | 390 | | | | | 395 | | | | | 400 |
| Ala | Gln | Arg | Glu | Val | Ser | Cys | Leu | Gln | Ser | Ser | Arg | Glu | Asn | Ser | His |
| | | | | 405 | | | | | 410 | | | | | 415 | |
| Leu | Val | Thr | Phe | Tyr | Gly | Ser | Glu | Ser | His | Arg | Gly | His | Leu | Phe | Val |
| | | | 420 | | | | | 425 | | | | | 430 | | |
| Cys | Val | Thr | Leu | Cys | Glu | Gln | Thr | Leu | Glu | Ala | Cys | Leu | Asp | Val | His |
| | | 435 | | | | | 440 | | | | 445 | | | | |
| Arg | Gly | Glu | Asp | Val | Glu | Asn | Glu | Glu | Asp | Glu | Phe | Ala | Arg | Asn | Val |
| | 450 | | | | | 455 | | | | | 460 | | | | |
| Leu | Ser | Ser | Ile | Phe | Lys | Ala | Val | Gln | Glu | Leu | His | Leu | Ser | Cys | Gly |
| 465 | | | | | 470 | | | | | 475 | | | | | 480 |
| Tyr | Thr | His | Gln | Asp | Leu | Gln | Pro | Gln | Asn | Ile | Leu | Ile | Asp | Ser | Lys |
| | | | | 485 | | | | | 490 | | | | | 495 | |
| Lys | Ala | Ala | His | Leu | Ala | Asp | Phe | Asp | Lys | Ser | Ile | Lys | Trp | Ala | Gly |
| | | | 500 | | | | | 505 | | | | | 510 | | |
| Asp | Pro | Gln | Glu | Val | Lys | Arg | Asp | Leu | Glu | Asp | Leu | Gly | Arg | Leu | Val |
| | | | 515 | | | | 520 | | | | | 525 | | | |
| Leu | Tyr | Val | Val | Lys | Lys | Gly | Ser | Ile | Ser | Phe | Glu | Asp | Leu | Lys | Ala |
| | 530 | | | | | 535 | | | | | 540 | | | | |
| Gln | Ser | Asn | Glu | Glu | Val | Val | Gln | Leu | Ser | Pro | Asp | Glu | Glu | Thr | Lys |
| 545 | | | | | 550 | | | | | 555 | | | | | 560 |
| Asp | Leu | Ile | His | Arg | Leu | Phe | His | Pro | Gly | Glu | His | Val | Arg | Asp | Cys |
| | | | | 565 | | | | | 570 | | | | | 575 | |
| Leu | Ser | Asp | Leu | Leu | Gly | His | Pro | Phe | Phe | Trp | Thr | Trp | Glu | Ser | Arg |
| | | | 580 | | | | | 585 | | | | | 590 | | |
| Tyr | Arg | Thr | Leu | Arg | Asn | Val | Gly | Asn | Glu | Ser | Asp | Ile | Lys | Thr | Arg |
| | | 595 | | | | | 600 | | | | | 605 | | | |
| Lys | Ser | Glu | Ser | Glu | Ile | Leu | Arg | Leu | Leu | Gln | Pro | Gly | Pro | Ser | Glu |
| 610 | | | | | 615 | | | | | 620 | | | | | |
| His | Ser | Lys | Ser | Phe | Asp | Lys | Trp | Thr | Thr | Lys | Ile | Asn | Glu | Cys | Val |
| 625 | | | | | 630 | | | | | 635 | | | | | 640 |
| Met | Lys | Lys | Met | Asn | Lys | Phe | Tyr | Glu | Lys | Arg | Gly | Asn | Phe | Tyr | Gln |
| | | | | 645 | | | | | 650 | | | | | 655 | |
| Asn | Thr | Val | Gly | Asp | Leu | Leu | Lys | Phe | Ile | Arg | Asn | Leu | Gly | Glu | His |
| | | | 660 | | | | | 665 | | | | | 670 | | |
| Ile | Asp | Glu | Glu | Lys | His | Lys | Lys | Met | Lys | Leu | Lys | Ile | Gly | Asp | Pro |
| | | | 675 | | | | 680 | | | | | 685 | | | |
| Ser | Leu | Tyr | Phe | Gln | Lys | Thr | Phe | Pro | Asp | Leu | Val | Ile | Tyr | Val | Tyr |
| | | 690 | | | | | 695 | | | | 700 | | | | |
| Thr | Lys | Leu | Gln | Asn | Thr | Glu | Tyr | Arg | Lys | His | Phe | Pro | Gln | Thr | His |
| 705 | | | | | 710 | | | | | 715 | | | | | 720 |
| Ser | Pro | Asn | Lys | Pro | Gln | Cys | Asp | Gly | Ala | Gly | Gly | Ala | Ser | Gly | Leu |
| | | | | 725 | | | | | 730 | | | | | 735 | |
| Ala | Ser | Pro | Gly | Cys |
| | | | 740 | |

( 2 ) INFORMATION FOR SEQ ID NO:3:

( i ) SEQUENCE CHARACTERISTICS:
        ( A ) LENGTH: 2928 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 104..2326

( x i ) SEQUENCE DESCRIPTION: SEQ ID NO:3:

```
AATCCCAACT TACACTCAAA GCTTCTTTGA TTAAGTGCTA GGAGATAAAT TTGCATTTTC        60

TCAAGGAAAA GGCTAAAAGT GGTAGCAGGT GGCATTTACC GTC ATG GAG AGC AGG        115
                                              Met Glu Ser Arg
                                                1

GAT CAT AAC AAC CCC CAG GAG GGA CCC ACG TCC TCC AGC GGT AGA AGG         163
Asp His Asn Asn Pro Gln Glu Gly Pro Thr Ser Ser Ser Gly Arg Arg
 5           10              15                      20

GCT GCA GTG GAA GAC AAT CAC TTG CTG ATT AAA GCT GTT CAA AAC GAA         211
Ala Ala Val Glu Asp Asn His Leu Leu Ile Lys Ala Val Gln Asn Glu
                 25              30                      35

GAT GTT GAC CTG GTC CAG CAA TTG CTG GAA GGT GGA GCC AAT GTT AAT         259
Asp Val Asp Leu Val Gln Gln Leu Leu Glu Gly Gly Ala Asn Val Asn
             40              45                  50

TTC CAG GAA GAG GAA GGG GGC TGG ACA CCT CTG CAT AAC GCA GTA CAA         307
Phe Gln Glu Glu Glu Gly Gly Trp Thr Pro Leu His Asn Ala Val Gln
         55              60                  65

ATG AGC AGG GAG GAC ATT GTG GAA CTT CTG CTT CGT CAT GGT GCT GAC         355
Met Ser Arg Glu Asp Ile Val Glu Leu Leu Leu Arg His Gly Ala Asp
     70              75                  80

CCT GTT CTG AGG AAG AAG AAT GGG GCC ACG CCT TTT ATC CTC GCA GCG         403
Pro Val Leu Arg Lys Lys Asn Gly Ala Thr Pro Phe Ile Leu Ala Ala
 85              90                  95                     100

ATT GCG GGG AGC GTG AAG CTG CTG AAA CTT TTC CTT TCT AAA GGA GCA         451
Ile Ala Gly Ser Val Lys Leu Leu Lys Leu Phe Leu Ser Lys Gly Ala
             105                 110                 115

GAT GTC AAT GAG TGT GAT TTT TAT GGC TTC ACA GCC TTC ATG GAA GCC         499
Asp Val Asn Glu Cys Asp Phe Tyr Gly Phe Thr Ala Phe Met Glu Ala
         120                 125                 130

GCT GTG TAT GGT AAG GTC AAA GCC CTA AAA TTC CTT TAT AAG AGA GGA         547
Ala Val Tyr Gly Lys Val Lys Ala Leu Lys Phe Leu Tyr Lys Arg Gly
     135                 140                 145

GCA AAT GTG AAT TTG AGG CGA AAG ACA AAG GAG GAT CAA GAG CGG CTG         595
Ala Asn Val Asn Leu Arg Arg Lys Thr Lys Glu Asp Gln Glu Arg Leu
 150                 155                 160

AGG AAA GGA GGG GCC ACA GCT CTC ATG GAC GCT GCT GAA AAA GGA CAC         643
Arg Lys Gly Gly Ala Thr Ala Leu Met Asp Ala Ala Glu Lys Gly His
165             170                 175                 180

GTA GAG GTC TTG AAG ATT CTC CTT GAT GAG ATG GGG GCA GAT GTA AAC         691
Val Glu Val Leu Lys Ile Leu Leu Asp Glu Met Gly Ala Asp Val Asn
             185                 190                 195

GCC TGT GAC AAT ATG GGC AGA AAT GCC TTG ATC CAT GCT CTC CTG AGC         739
Ala Cys Asp Asn Met Gly Arg Asn Ala Leu Ile His Ala Leu Leu Ser
         200                 205                 210

TCT GAC GAT AGT GAT GTG GAG GCT ATT ACG CAT CTG CTG CTG GAC CAT         787
Ser Asp Asp Ser Asp Val Glu Ala Ile Thr His Leu Leu Leu Asp His
     215                 220                 225
```

-continued

| | | | | | | | | | | | | | | | | |
|---|---|---|---|---|---|---|---|---|---|---|---|---|---|---|---|---|
| GGG | GCT | GAT | GTC | AAT | GTG | AGG | GGA | GAA | AGA | GGG | AAG | ACT | CCC | CTG | ATC | 835 |
| Gly | Ala | Asp | Val | Asn | Val | Arg | Gly | Glu | Arg | Gly | Lys | Thr | Pro | Leu | Ile | |
| | 230 | | | | 235 | | | | | 240 | | | | | | |
| CTG | GCA | GTG | GAG | AAG | AAG | CAC | TTG | GGT | TTG | GTG | CAG | AGG | CTT | CTG | GAG | 883 |
| Leu | Ala | Val | Glu | Lys | Lys | His | Leu | Gly | Leu | Val | Gln | Arg | Leu | Leu | Glu | |
| 245 | | | | | 250 | | | | | 255 | | | | | 260 | |
| CAA | GAG | CAC | ATA | GAG | ATT | AAT | GAC | ACA | GAC | AGT | GAT | GGC | AAA | ACA | GCA | 931 |
| Gln | Glu | His | Ile | Glu | Ile | Asn | Asp | Thr | Asp | Ser | Asp | Gly | Lys | Thr | Ala | |
| | | | | 265 | | | | | 270 | | | | | 275 | | |
| CTG | CTG | CTT | GCT | GTT | GAA | CTC | AAA | CTG | AAG | AAA | ATC | GCC | GAG | TTG | CTG | 979 |
| Leu | Leu | Leu | Ala | Val | Glu | Leu | Lys | Leu | Lys | Lys | Ile | Ala | Glu | Leu | Leu | |
| | | | 280 | | | | 285 | | | | | 290 | | | | |
| TGC | AAA | CGT | GGA | GCC | AGT | ACA | GAT | TGT | GGG | GAT | CTT | GTT | ATG | ACA | GCG | 1027 |
| Cys | Lys | Arg | Gly | Ala | Ser | Thr | Asp | Cys | Gly | Asp | Leu | Val | Met | Thr | Ala | |
| | | 295 | | | | | 300 | | | | | 305 | | | | |
| AGG | CGG | AAT | TAT | GAC | CAT | TCC | CTT | GTG | AAG | GTT | CTT | CTC | TCT | CAT | GGA | 1075 |
| Arg | Arg | Asn | Tyr | Asp | His | Ser | Leu | Val | Lys | Val | Leu | Leu | Ser | His | Gly | |
| | 310 | | | | | 315 | | | | | 320 | | | | | |
| GCC | AAA | GAA | GAT | TTT | CAC | CCT | CCT | GCT | GAA | GAC | TGG | AAG | CCT | CAG | AGC | 1123 |
| Ala | Lys | Glu | Asp | Phe | His | Pro | Pro | Ala | Glu | Asp | Trp | Lys | Pro | Gln | Ser | |
| 325 | | | | | 330 | | | | | 335 | | | | | 340 | |
| TCA | CAC | TGG | GGG | GCA | GCC | CTG | AAG | GAT | CTC | CAC | AGA | ATA | TAC | CGC | CCT | 1171 |
| Ser | His | Trp | Gly | Ala | Ala | Leu | Lys | Asp | Leu | His | Arg | Ile | Tyr | Arg | Pro | |
| | | | | 345 | | | | | 350 | | | | | 355 | | |
| ATG | ATT | GGC | AAA | CTC | AAG | TTC | TTT | ATT | GAT | GAA | AAA | TAC | AAA | ATT | GCT | 1219 |
| Met | Ile | Gly | Lys | Leu | Lys | Phe | Phe | Ile | Asp | Glu | Lys | Tyr | Lys | Ile | Ala | |
| | | | 360 | | | | | 365 | | | | | 370 | | | |
| GAT | ACT | TCA | GAA | GGA | GGC | ATC | TAC | CTG | GGG | TTC | TAT | GAG | AAG | CAA | GAA | 1267 |
| Asp | Thr | Ser | Glu | Gly | Gly | Ile | Tyr | Leu | Gly | Phe | Tyr | Glu | Lys | Gln | Glu | |
| | | 375 | | | | | 380 | | | | | 385 | | | | |
| GTA | GCT | GTG | AAG | ACG | TTC | TGT | GAG | GGC | AGC | CCA | CGT | GCA | CAG | CGG | GAA | 1315 |
| Val | Ala | Val | Lys | Thr | Phe | Cys | Glu | Gly | Ser | Pro | Arg | Ala | Gln | Arg | Glu | |
| | 390 | | | | | 395 | | | | | 400 | | | | | |
| GTC | TCT | TGT | CTG | CAA | AGC | AGC | CGA | GAG | AAC | AGT | CAC | TTG | GTG | ACA | TTC | 1363 |
| Val | Ser | Cys | Leu | Gln | Ser | Ser | Arg | Glu | Asn | Ser | His | Leu | Val | Thr | Phe | |
| 405 | | | | | 410 | | | | | 415 | | | | | 420 | |
| TAT | GGG | AGT | GAG | AGC | CAC | AGG | GGC | CAC | TTG | TTT | GTG | TGT | GTC | ACC | CTC | 1411 |
| Tyr | Gly | Ser | Glu | Ser | His | Arg | Gly | His | Leu | Phe | Val | Cys | Val | Thr | Leu | |
| | | | | 425 | | | | | 430 | | | | | 435 | | |
| TGT | GAG | CAG | ACT | CTG | GAA | GCG | TGT | TTG | GAT | GTG | CAC | AGA | GGG | GAA | GAT | 1459 |
| Cys | Glu | Gln | Thr | Leu | Glu | Ala | Cys | Leu | Asp | Val | His | Arg | Gly | Glu | Asp | |
| | | | 440 | | | | | 445 | | | | | 450 | | | |
| GTG | GAA | AAT | GAG | GAA | GAT | GAA | TTT | GCC | CGA | AAT | GTC | CTG | TCA | TCT | ATA | 1507 |
| Val | Glu | Asn | Glu | Glu | Asp | Glu | Phe | Ala | Arg | Asn | Val | Leu | Ser | Ser | Ile | |
| | | 455 | | | | | 460 | | | | | 465 | | | | |
| TTT | AAG | GCT | GTT | CAA | GAA | CTA | CAC | TTG | TCC | TGT | GGA | TAC | ACC | CAC | CAG | 1555 |
| Phe | Lys | Ala | Val | Gln | Glu | Leu | His | Leu | Ser | Cys | Gly | Tyr | Thr | His | Gln | |
| | 470 | | | | | 475 | | | | | 480 | | | | | |
| GAT | CTG | CAA | CCA | CAA | AAC | ATC | TTA | ATA | GAT | TCT | AAG | AAA | GCT | GCT | CAC | 1603 |
| Asp | Leu | Gln | Pro | Gln | Asn | Ile | Leu | Ile | Asp | Ser | Lys | Lys | Ala | Ala | His | |
| 485 | | | | | 490 | | | | | 495 | | | | | 500 | |
| CTG | GCA | GAT | TTT | GAT | AAG | AGC | ATC | AAG | TGG | GCT | GGA | GAT | CCA | CAG | GAA | 1651 |
| Leu | Ala | Asp | Phe | Asp | Lys | Ser | Ile | Lys | Trp | Ala | Gly | Asp | Pro | Gln | Glu | |
| | | | | 505 | | | | | 510 | | | | | 515 | | |
| GTC | AAG | AGA | GAT | CTA | GAG | GAC | CTT | GGA | CGG | CTG | GTC | CTC | TAT | GTG | GTA | 1699 |
| Val | Lys | Arg | Asp | Leu | Glu | Asp | Leu | Gly | Arg | Leu | Val | Leu | Tyr | Val | Val | |
| | | | 520 | | | | | 525 | | | | | 530 | | | |
| AAG | AAG | GGA | AGC | ATC | TCA | TTT | GAG | GAT | CTG | AAA | GCT | CAA | AGT | AAT | GAA | 1747 |
| Lys | Lys | Gly | Ser | Ile | Ser | Phe | Glu | Asp | Leu | Lys | Ala | Gln | Ser | Asn | Glu | |
| | | 535 | | | | | 540 | | | | | 545 | | | | |

```
GAG  GTG  GTT  CAA  CTT  TCT  CCA  GAT  GAG  GAA  ACT  AAG  GAC  CTC  ATT  CAT    1795
Glu  Val  Val  Gln  Leu  Ser  Pro  Asp  Glu  Glu  Thr  Lys  Asp  Leu  Ile  His
     550                      555                      560

CGT  CTC  TTC  CAT  CCT  GGG  GAA  CAT  GTG  AGG  GAC  TGT  CTG  AGT  GAC  CTG    1843
Arg  Leu  Phe  His  Pro  Gly  Glu  His  Val  Arg  Asp  Cys  Leu  Ser  Asp  Leu
565                      570                      575                      580

CTG  GGT  CAT  CCC  TTC  TTT  TGG  ACT  TGG  GAG  AGC  CGC  TAT  AGG  ACG  CTT    1891
Leu  Gly  His  Pro  Phe  Phe  Trp  Thr  Trp  Glu  Ser  Arg  Tyr  Arg  Thr  Leu
                         585                      590                      595

CGG  AAT  GTG  GGA  AAT  GAA  TCC  GAC  ATC  AAA  ACA  CGA  AAA  TCT  GAA  AGT    1939
Arg  Asn  Val  Gly  Asn  Glu  Ser  Asp  Ile  Lys  Thr  Arg  Lys  Ser  Glu  Ser
               600                      605                      610

GAG  ATC  CTC  AGA  CTA  CTG  CAA  CCT  GGG  CCT  TCT  GAA  CAT  TCC  AAA  AGT    1987
Glu  Ile  Leu  Arg  Leu  Leu  Gln  Pro  Gly  Pro  Ser  Glu  His  Ser  Lys  Ser
               615                      620                      625

TTT  GAC  AAG  TGG  ACG  ACT  AAG  ATT  AAT  GAA  TGT  GTT  ATG  AAA  AAA  ATG    2035
Phe  Asp  Lys  Trp  Thr  Thr  Lys  Ile  Asn  Glu  Cys  Val  Met  Lys  Lys  Met
     630                      635                      640

AAT  AAG  TTT  TAT  GAA  AAA  AGA  GGC  AAT  TTC  TAC  CAG  AAC  ACT  GTG  GGT    2083
Asn  Lys  Phe  Tyr  Glu  Lys  Arg  Gly  Asn  Phe  Tyr  Gln  Asn  Thr  Val  Gly
645                      650                      655                      660

GAT  CTG  CTA  AAG  TTC  ATC  CGG  AAT  TTG  GGA  GAA  CAC  ATT  GAT  GAA  GAA    2131
Asp  Leu  Leu  Lys  Phe  Ile  Arg  Asn  Leu  Gly  Glu  His  Ile  Asp  Glu  Glu
                         665                      670                      675

AAG  CAT  AAA  AAG  ATG  AAA  TTA  AAA  ATT  GGA  GAC  CCT  TCC  CTG  TAT  TTT    2179
Lys  His  Lys  Lys  Met  Lys  Leu  Lys  Ile  Gly  Asp  Pro  Ser  Leu  Tyr  Phe
               680                      685                      690

CAG  AAG  ACA  TTT  CCA  GAT  CTG  GTG  ATC  TAT  GTC  TAC  ACA  AAA  CTA  CAG    2227
Gln  Lys  Thr  Phe  Pro  Asp  Leu  Val  Ile  Tyr  Val  Tyr  Thr  Lys  Leu  Gln
               695                      700                      705

AAC  ACA  GAA  TAT  AGA  AAG  CAT  TTC  CCC  CAA  ACC  CAC  AGT  CCA  AAC  AAA    2275
Asn  Thr  Glu  Tyr  Arg  Lys  His  Phe  Pro  Gln  Thr  His  Ser  Pro  Asn  Lys
     710                      715                      720

CCT  CAG  TGT  GAT  GGA  GCT  GGT  GGG  GCC  AGT  GGG  TTG  GCC  AGC  CCT  GGG    2323
Pro  Gln  Cys  Asp  Gly  Ala  Gly  Gly  Ala  Ser  Gly  Leu  Ala  Ser  Pro  Gly
725                      730                      735                      740

TGC  TGATGGACTG  ATTTGCTGGA  GTTCAGGGAA  CTACTTATTA  GCTGTAGAGT                   2376
Cys

CCTTGGCAAA  TCACAACATT  CTGGGCCTTT  TAACTCACCA  GGTTGCTTGT  GAGGGATGAG             2436

TTGCATAGCT  GATATGTCAG  TCCCTGGCAT  CGTGTATTCC  ATATGTCTAT  AACAAAAGCA             2496

ATATATACCC  AGACTACACT  AGTCCATAAG  CTTTACCCAC  TAACTGGGAG  GACATTCTGC             2556

TAAGATTCCT  TTTGTCAATT  GCACCAAAAG  AATGAGTGCC  TTGACCCCTA  ATGCTGCATA             2616

TGTTACAATT  CTCTCACTTA  ATTTTCCCAA  TGATCTTGCA  AAACAGGGAT  TATCATCCCC             2676

ATTTAAGAAC  TGAGGAACCT  GAGACTCAGA  GAGTGTGAGC  TACTGGCCCA  AGATTATTCA             2736

ATTTATACCT  AGCACTTTAT  AAATTTATGT  GGTGTTATTG  GTACCTCTCA  TTTGGGCACC             2796

TTAAAACTTA  ACTATCTTCC  AGGGCTCTTC  CAGATGAGGC  CCAAAACATA  TATAGGGGTT             2856

CCAGGAATCT  CATTCATTCA  TTCAGTATTT  ATTGAGCATC  TAGTATAAGT  CTGGGCACTG             2916

GATGCATGAA  TT                                                                    2928
```

( 2 ) INFORMATION FOR SEQ ID NO:4:

( i ) SEQUENCE CHARACTERISTICS:
        ( A ) LENGTH: 741 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Ser | Arg | Asp | His | Asn | Asn | Pro | Gln | Glu | Gly | Pro | Thr | Ser | Ser |
| 1 | | | | 5 | | | | | 10 | | | | | 15 | |

| Ser | Gly | Arg | Arg | Ala | Ala | Val | Glu | Asp | Asn | His | Leu | Leu | Ile | Lys | Ala |
| | | | 20 | | | | | 25 | | | | | 30 | | |

| Val | Gln | Asn | Glu | Asp | Val | Asp | Leu | Val | Gln | Gln | Leu | Leu | Glu | Gly | Gly |
| | | 35 | | | | | 40 | | | | | 45 | | | |

| Ala | Asn | Val | Asn | Phe | Gln | Glu | Glu | Gly | Gly | Trp | Thr | Pro | Leu | His |
| | 50 | | | | 55 | | | | | | 60 | | | | |

| Asn | Ala | Val | Gln | Met | Ser | Arg | Glu | Asp | Ile | Val | Glu | Leu | Leu | Leu | Arg |
| 65 | | | | | 70 | | | | | 75 | | | | | 80 |

| His | Gly | Ala | Asp | Pro | Val | Leu | Arg | Lys | Lys | Asn | Gly | Ala | Thr | Pro | Phe |
| | | | | 85 | | | | | 90 | | | | | 95 | |

| Ile | Leu | Ala | Ala | Ile | Ala | Gly | Ser | Val | Lys | Leu | Leu | Lys | Leu | Phe | Leu |
| | | | 100 | | | | | 105 | | | | | 110 | | |

| Ser | Lys | Gly | Ala | Asp | Val | Asn | Glu | Cys | Asp | Phe | Tyr | Gly | Phe | Thr | Ala |
| | | | 115 | | | | | 120 | | | | | 125 | | |

| Phe | Met | Glu | Ala | Ala | Val | Tyr | Gly | Lys | Val | Lys | Ala | Leu | Lys | Phe | Leu |
| | 130 | | | | | 135 | | | | | 140 | | | | |

| Tyr | Lys | Arg | Gly | Ala | Asn | Val | Asn | Leu | Arg | Arg | Lys | Thr | Lys | Glu | Asp |
| 145 | | | | | 150 | | | | | 155 | | | | | 160 |

| Gln | Glu | Arg | Leu | Arg | Lys | Gly | Gly | Ala | Thr | Ala | Leu | Met | Asp | Ala | Ala |
| | | | | 165 | | | | | 170 | | | | | 175 | |

| Glu | Lys | Gly | His | Val | Glu | Val | Leu | Lys | Ile | Leu | Leu | Asp | Glu | Met | Gly |
| | | | 180 | | | | | 185 | | | | | 190 | | |

| Ala | Asp | Val | Asn | Ala | Cys | Asp | Asn | Met | Gly | Arg | Asn | Ala | Leu | Ile | His |
| | | 195 | | | | | 200 | | | | | 205 | | | |

| Ala | Leu | Leu | Ser | Ser | Asp | Asp | Ser | Asp | Val | Glu | Ala | Ile | Thr | His | Leu |
| | 210 | | | | | 215 | | | | | 220 | | | | |

| Leu | Leu | Asp | His | Gly | Ala | Asp | Val | Asn | Val | Arg | Gly | Glu | Arg | Gly | Lys |
| 225 | | | | | 230 | | | | | 235 | | | | | 240 |

| Thr | Pro | Leu | Ile | Leu | Ala | Val | Glu | Lys | Lys | His | Leu | Gly | Leu | Val | Gln |
| | | | | 245 | | | | | 250 | | | | | 255 | |

| Arg | Leu | Leu | Glu | Gln | Glu | His | Ile | Glu | Ile | Asn | Asp | Thr | Asp | Ser | Asp |
| | | | | 260 | | | | | 265 | | | | | 270 | |

| Gly | Lys | Thr | Ala | Leu | Leu | Leu | Ala | Val | Glu | Leu | Lys | Leu | Lys | Lys | Ile |
| | | | 275 | | | | | 280 | | | | | 285 | | |

| Ala | Glu | Leu | Leu | Cys | Lys | Arg | Gly | Ala | Ser | Thr | Asp | Cys | Gly | Asp | Leu |
| | 290 | | | | | 295 | | | | | 300 | | | | |

| Val | Met | Thr | Ala | Arg | Arg | Asn | Tyr | Asp | His | Ser | Leu | Val | Lys | Val | Leu |
| 305 | | | | | 310 | | | | | 315 | | | | | 320 |

| Leu | Ser | His | Gly | Ala | Lys | Glu | Asp | Phe | His | Pro | Pro | Ala | Glu | Asp | Trp |
| | | | | 325 | | | | | 330 | | | | | 335 | |

| Lys | Pro | Gln | Ser | Ser | His | Trp | Gly | Ala | Ala | Leu | Lys | Asp | Leu | His | Arg |
| | | | 340 | | | | | 345 | | | | | 350 | | |

| Ile | Tyr | Arg | Pro | Met | Ile | Gly | Lys | Leu | Lys | Phe | Phe | Ile | Asp | Glu | Lys |
| | | 355 | | | | | 360 | | | | | 365 | | | |

| Tyr | Lys | Ile | Ala | Asp | Thr | Ser | Glu | Gly | Gly | Ile | Tyr | Leu | Gly | Phe | Tyr |
| | 370 | | | | | 375 | | | | | 380 | | | | |

| Glu | Lys | Gln | Glu | Val | Ala | Val | Lys | Thr | Phe | Cys | Glu | Gly | Ser | Pro | Arg |
| 385 | | | | | 390 | | | | | 395 | | | | | 400 |

| Ala | Gln | Arg | Glu | Val | Ser | Cys | Leu | Gln | Ser | Ser | Arg | Glu | Asn | Ser | His |
| | | | | 405 | | | | | 410 | | | | | 415 | |

| | | | | | | | | | | | | | | |
|---|---|---|---|---|---|---|---|---|---|---|---|---|---|---|
| Leu | Val | Thr | Phe<br>420 | Tyr | Gly | Ser | Glu<br>425 | Ser | His | Arg | Gly | His<br>430 | Leu | Phe | Val |
| Cys | Val | Thr<br>435 | Leu | Cys | Glu | Gln | Thr<br>440 | Leu | Glu | Ala | Cys | Leu<br>445 | Asp | Val | His |
| Arg | Gly<br>450 | Glu | Asp | Val | Glu | Asn<br>455 | Glu | Glu | Asp | Glu | Phe<br>460 | Ala | Arg | Asn | Val |
| Leu<br>465 | Ser | Ser | Ile | Phe | Lys<br>470 | Ala | Val | Gln | Glu | Leu<br>475 | His | Leu | Ser | Cys | Gly<br>480 |
| Tyr | Thr | His | Gln | Asp<br>485 | Leu | Gln | Pro | Gln | Asn<br>490 | Ile | Leu | Ile | Asp | Ser<br>495 | Lys |
| Lys | Ala | Ala | His<br>500 | Leu | Ala | Asp | Phe | Asp<br>505 | Lys | Ser | Ile | Lys | Trp<br>510 | Ala | Gly |
| Asp | Pro | Gln<br>515 | Glu | Val | Lys | Arg | Asp<br>520 | Leu | Glu | Asp | Leu | Gly<br>525 | Arg | Leu | Val |
| Leu | Tyr<br>530 | Val | Val | Lys | Lys | Gly<br>535 | Ser | Ile | Ser | Phe | Glu<br>540 | Asp | Leu | Lys | Ala |
| Gln<br>545 | Ser | Asn | Glu | Glu | Val<br>550 | Val | Gln | Leu | Ser | Pro<br>555 | Asp | Glu | Glu | Thr | Lys<br>560 |
| Asp | Leu | Ile | His | Arg<br>565 | Leu | Phe | His | Pro | Gly<br>570 | Glu | His | Val | Arg | Asp<br>575 | Cys |
| Leu | Ser | Asp | Leu<br>580 | Leu | Gly | His | Pro | Phe<br>585 | Phe | Trp | Thr | Trp | Glu<br>590 | Ser | Arg |
| Tyr | Arg | Thr<br>595 | Leu | Arg | Asn | Val | Gly<br>600 | Asn | Glu | Ser | Asp | Ile<br>605 | Lys | Thr | Arg |
| Lys | Ser<br>610 | Glu | Ser | Glu | Ile | Leu<br>615 | Arg | Leu | Leu | Gln | Pro<br>620 | Gly | Pro | Ser | Glu |
| His<br>625 | Ser | Lys | Ser | Phe | Asp<br>630 | Lys | Trp | Thr | Thr | Lys<br>635 | Ile | Asn | Glu | Cys | Val<br>640 |
| Met | Lys | Lys | Met | Asn<br>645 | Lys | Phe | Tyr | Glu | Lys<br>650 | Arg | Gly | Asn | Phe | Tyr<br>655 | Gln |
| Asn | Thr | Val | Gly<br>660 | Asp | Leu | Leu | Lys | Phe<br>665 | Ile | Arg | Asn | Leu | Gly<br>670 | Glu | His |
| Ile | Asp | Glu<br>675 | Glu | Lys | His | Lys | Lys<br>680 | Met | Lys | Leu | Lys | Ile<br>685 | Gly | Asp | Pro |
| Ser | Leu<br>690 | Tyr | Phe | Gln | Lys | Thr<br>695 | Phe | Pro | Asp | Leu | Val<br>700 | Ile | Tyr | Val | Tyr |
| Thr<br>705 | Lys | Leu | Gln | Asn | Thr<br>710 | Glu | Tyr | Arg | Lys | His<br>715 | Phe | Pro | Gln | Thr | His<br>720 |
| Ser | Pro | Asn | Lys | Pro<br>725 | Gln | Cys | Asp | Gly | Ala<br>730 | Gly | Gly | Ala | Ser | Gly<br>735 | Leu |
| Ala | Ser | Pro | Gly<br>740 | Cys | | | | | | | | | | | |

( 2 ) INFORMATION FOR SEQ ID NO:5:

( i ) SEQUENCE CHARACTERISTICS:
        ( A ) LENGTH: 2200 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 164..2200

( x i ) SEQUENCE DESCRIPTION: SEQ ID NO:5:

```
ATTCGGCACG AGGAAGGTGC CAATTACTAG CTCCCTTCTT TATTCGTGTA CTGATGAGAT        60

GTCAGAAGAC AGAACATAAT CAGCCCAATC CCTACTCCAA GACTCTCATT GTGTCCCAAA       120

GAAACACACG TGTGCATTTC CCAAGGAAAA GGCATTGAGG ACC ATG GAG ACC CCG         175
                                            Met Glu Thr Pro
                                             1
```

```
GAT TAT AAC ACA CCT CAG GGT GGA ACC CCA TCA GCG GGA AGT CAG AGG         223
Asp Tyr Asn Thr Pro Gln Gly Gly Thr Pro Ser Ala Gly Ser Gln Arg
 5               10                  15                      20

ACC GTT GTC GAA GAT GAT TCT TCG TTG ATC AAA GCT GTT CAG AAG GGA         271
Thr Val Val Glu Asp Asp Ser Ser Leu Ile Lys Ala Val Gln Lys Gly
                 25                  30                  35

GAT GTT GTC AGG GTC CAG CAA TTG TTA GAA AAA GGG GCT GAT GCC AAT         319
Asp Val Val Arg Val Gln Gln Leu Leu Glu Lys Gly Ala Asp Ala Asn
             40                  45                  50

GCC TGT GAA GAC ACC TGG GGC TGG ACA CCT TTG CAC AAC GCA GTG CAA         367
Ala Cys Glu Asp Thr Trp Gly Trp Thr Pro Leu His Asn Ala Val Gln
         55                  60                  65

GCT GGC AGG GTA GAC ATT GTG AAC CTC CTG CTT AGT CAT GGT GCT GAC         415
Ala Gly Arg Val Asp Ile Val Asn Leu Leu Leu Ser His Gly Ala Asp
     70                  75                  80

CCT CAT CGG AGG AAG AAG AAT GGG GCC ACC CCC TTC ATC ATT GCT GGG         463
Pro His Arg Arg Lys Lys Asn Gly Ala Thr Pro Phe Ile Ile Ala Gly
 85                  90                  95                 100

ATC CAG GGA GAT GTG AAA CTG CTC GAG ATT CTC CTC TCT TGT GGT GCA         511
Ile Gln Gly Asp Val Lys Leu Leu Glu Ile Leu Leu Ser Cys Gly Ala
                105                 110                 115

GAC GTC AAT GAG TGT GAC GAG AAC GGA TTC ACG GCT TTC ATG GAA GCT         559
Asp Val Asn Glu Cys Asp Glu Asn Gly Phe Thr Ala Phe Met Glu Ala
            120                 125                 130

GCT GAG CGT GGT AAC GCT GAA GCC TTA AGA TTC CTT TTT GCT AAG GGA         607
Ala Glu Arg Gly Asn Ala Glu Ala Leu Arg Phe Leu Phe Ala Lys Gly
        135                 140                 145

GCC AAT GTG AAT TTG CGA CGA CAG ACA ACG AAG GAC AAA AGG CGA TTG         655
Ala Asn Val Asn Leu Arg Arg Gln Thr Thr Lys Asp Lys Arg Arg Leu
    150                 155                 160

AAG CAA GGA GGC GCC ACA GCT CTC ATG AGC GCT GCT GAG AAG GGC CAC         703
Lys Gln Gly Gly Ala Thr Ala Leu Met Ser Ala Ala Glu Lys Gly His
165                 170                 175                 180

CTG GAA GTC CTG AGA ATT CTC CTC AAT GAC ATG AAG GCA GAA GTC GAT         751
Leu Glu Val Leu Arg Ile Leu Leu Asn Asp Met Lys Ala Glu Val Asp
                185                 190                 195

GCT CGG GAC AAC ATG GGC AGA AAT GCC CTG ATC CGT ACT CTG CTG AAC         799
Ala Arg Asp Asn Met Gly Arg Asn Ala Leu Ile Arg Thr Leu Leu Asn
            200                 205                 210

TGG GAT TGT GAA AAT GTG GAG GAG ATT ACT TCA ATC CTG ATT CAG CAC         847
Trp Asp Cys Glu Asn Val Glu Glu Ile Thr Ser Ile Leu Ile Gln His
        215                 220                 225

GGG GCT GAT GTT AAC GTG AGA GGA GAA AGA GGG AAA ACA CCC CTC ATC         895
Gly Ala Asp Val Asn Val Arg Gly Glu Arg Gly Lys Thr Pro Leu Ile
    230                 235                 240

GCA GCA GTG GAG AGG AAG CAC ACA GGC TTG GTG CAG ATG CTC CTG AGT         943
Ala Ala Val Glu Arg Lys His Thr Gly Leu Val Gln Met Leu Leu Ser
245                 250                 255                 260

CGG GAA GGC ATA AAC ATA GAT GCC AGG GAT AAC GAG GGC AAG ACA GCT         991
Arg Glu Gly Ile Asn Ile Asp Ala Arg Asp Asn Glu Gly Lys Thr Ala
                265                 270                 275

CTG CTA ATT GCT GTT GAT AAA CAA CTG AAG GAA ATT GTC CAG TTG CTT        1039
Leu Leu Ile Ala Val Asp Lys Gln Leu Lys Glu Ile Val Gln Leu Leu
            280                 285                 290
```

```
CTT GAA AAG GGA GCT GAT AAG TGT GAC GAT CTT GTT TGG ATA GCC AGG         1087
Leu Glu Lys Gly Ala Asp Lys Cys Asp Asp Leu Val Trp Ile Ala Arg
        295                 300                 305

AGG AAT CAT GAC TAT CAC CTT GTA AAG CTT CTC CTC CCT TAT GTA GCT         1135
Arg Asn His Asp Tyr His Leu Val Lys Leu Leu Leu Pro Tyr Val Ala
        310                 315                 320

AAT CCT GAC ACC GAC CCT CCT GCT GGA GAC TGG TCG CCT CAC AGT TCA         1183
Asn Pro Asp Thr Asp Pro Pro Ala Gly Asp Trp Ser Pro His Ser Ser
325                 330                 335                 340

CGT TGG GGG ACA GCC TTG AAA AGC CTC CAC AGT ATG ACT CGA CCC ATG         1231
Arg Trp Gly Thr Ala Leu Lys Ser Leu His Ser Met Thr Arg Pro Met
            345                 350                 355

ATT GGC AAA CTC AAG ATC TTC ATT CAT GAT GAC TAT AAA ATT GCT GGC         1279
Ile Gly Lys Leu Lys Ile Phe Ile His Asp Asp Tyr Lys Ile Ala Gly
        360                 365                 370

ACT TCC GAA GGG GCT GTC TAC CTA GGG ATC TAT GAC AAT CGA GAA GTG         1327
Thr Ser Glu Gly Ala Val Tyr Leu Gly Ile Tyr Asp Asn Arg Glu Val
        375                 380                 385

GCT GTG AAG GTC TTC CGT GAG AAT AGC CCA CGT GGA TGT AAG GAA GTC         1375
Ala Val Lys Val Phe Arg Glu Asn Ser Pro Arg Gly Cys Lys Glu Val
        390                 395                 400

TCT TGT CTG CGG GAC TGC GGT GAC CAC AGT AAC TTA GTG GCT TTC TAT         1423
Ser Cys Leu Arg Asp Cys Gly Asp His Ser Asn Leu Val Ala Phe Tyr
405                 410                 415                 420

GGA AGA GAG GAC GAT AAG GGC TGT TTA TAT GTG TGT GTG TCC CTG TGT         1471
Gly Arg Glu Asp Asp Lys Gly Cys Leu Tyr Val Cys Val Ser Leu Cys
                425                 430                 435

GAG TGG ACA CTG GAA GAG TTC CTG AGG TTG CCC AGA GAG GAA CCT GTG         1519
Glu Trp Thr Leu Glu Glu Phe Leu Arg Leu Pro Arg Glu Glu Pro Val
            440                 445                 450

GAG AAC GGG GAA GAT AAG TTT GCC CAC AGC ATC CTA TTA TCT ATA TTT         1567
Glu Asn Gly Glu Asp Lys Phe Ala His Ser Ile Leu Leu Ser Ile Phe
        455                 460                 465

GAG GGT GTT CAA AAA CTA CAC TTG CAT GGA TAT TCC CAT CAG GAC CTG         1615
Glu Gly Val Gln Lys Leu His Leu His Gly Tyr Ser His Gln Asp Leu
        470                 475                 480

CAA CCA CAA AAC ATC TTA ATA GAT TCC AAG AAA GCT GTC CGG CTG GCA         1663
Gln Pro Gln Asn Ile Leu Ile Asp Ser Lys Lys Ala Val Arg Leu Ala
485                 490                 495                 500

GAT TTT GAT CAG AGC ATC CGA TGG ATG GGA GAG TCA CAG ATG GTC AGG         1711
Asp Phe Asp Gln Ser Ile Arg Trp Met Gly Glu Ser Gln Met Val Arg
                505                 510                 515

AGA GAC TTG GAG GAT CTT GGA CGG CTG GTT CTC TAC GTG GTA ATG AAA         1759
Arg Asp Leu Glu Asp Leu Gly Arg Leu Val Leu Tyr Val Val Met Lys
            520                 525                 530

GGT GAG ATC CCC TTT GAG ACA CTA AAG ACT CAG AAT GAT GAA GTG CTG         1807
Gly Glu Ile Pro Phe Glu Thr Leu Lys Thr Gln Asn Asp Glu Val Leu
        535                 540                 545

CTT ACA ATG TCT CCA GAT GAG GAG ACT AAG GAC CTC ATT CAT TGC CTG         1855
Leu Thr Met Ser Pro Asp Glu Glu Thr Lys Asp Leu Ile His Cys Leu
        550                 555                 560

TTT TCT CCT GGA GAA AAT GTC AAG AAC TGC CTG GTA GAC CTG CTT GGC         1903
Phe Ser Pro Gly Glu Asn Val Lys Asn Cys Leu Val Asp Leu Leu Gly
565                 570                 575                 580

CAT CCT TTC TTT TGG ACT TGG GAG AAC CGC TAT AGA ACA CTC CGG AAT         1951
His Pro Phe Phe Trp Thr Trp Glu Asn Arg Tyr Arg Thr Leu Arg Asn
                585                 590                 595

GTG GGA AAT GAA TCT GAC ATC AAA GTA CGG AAA TGT AAA AGT GAT CTT         1999
Val Gly Asn Glu Ser Asp Ile Lys Val Arg Lys Cys Lys Ser Asp Leu
                600                 605                 610
```

```
CTC AGA CTA CTG CAG CAT CAG ACA CTT GAG CCT CCC AGA AGC TTT GAC    2047
Leu Arg Leu Leu Gln His Gln Thr Leu Glu Pro Pro Arg Ser Phe Asp
        615                 620                 625

CAG TGG ACA TCT AAG ATC GAC AAA AAT GTT ATG GAT GAA ATG AAT CAT    2095
Gln Trp Thr Ser Lys Ile Asp Lys Asn Val Met Asp Glu Met Asn His
630                     635                 640

TTC TAC GAA AAG AGA AAA AAA AAC CCT TAT CAG GAT ACT GTA GGT GAT    2143
Phe Tyr Glu Lys Arg Lys Lys Asn Pro Tyr Gln Asp Thr Val Gly Asp
645                 650                 655                 660

CTG CTG AAG TTT ATT CGG AAT ATA GGC GAA CAC ATC AAT GAG GAA AAA    2191
Leu Leu Lys Phe Ile Arg Asn Ile Gly Glu His Ile Asn Glu Glu Lys
            665                 670                 675

AAG CGG GGG                                                        2200
Lys Arg Gly
```

( 2 ) INFORMATION FOR SEQ ID NO:6:

( i ) SEQUENCE CHARACTERISTICS:
        ( A ) LENGTH: 679 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Glu Thr Pro Asp Tyr Asn Thr Pro Gln Gly Gly Thr Pro Ser Ala
 1               5                  10                  15

Gly Ser Gln Arg Thr Val Val Glu Asp Ser Ser Leu Ile Lys Ala
            20                  25                  30

Val Gln Lys Gly Asp Val Val Arg Val Gln Gln Leu Leu Glu Lys Gly
        35                  40                  45

Ala Asp Ala Asn Ala Cys Glu Asp Thr Trp Gly Trp Thr Pro Leu His
50                  55                  60

Asn Ala Val Gln Ala Gly Arg Val Asp Ile Val Asn Leu Leu Leu Ser
65                  70                  75                  80

His Gly Ala Asp Pro His Arg Arg Lys Lys Asn Gly Ala Thr Pro Phe
                85                  90                  95

Ile Ile Ala Gly Ile Gln Gly Asp Val Lys Leu Leu Glu Ile Leu Leu
            100                 105                 110

Ser Cys Gly Ala Asp Val Asn Glu Cys Asp Glu Asn Gly Phe Thr Ala
        115                 120                 125

Phe Met Glu Ala Ala Glu Arg Gly Asn Ala Glu Ala Leu Arg Phe Leu
130                 135                 140

Phe Ala Lys Gly Ala Asn Val Asn Leu Arg Arg Gln Thr Thr Lys Asp
145                 150                 155                 160

Lys Arg Arg Leu Lys Gln Gly Gly Ala Thr Ala Leu Met Ser Ala Ala
                165                 170                 175

Glu Lys Gly His Leu Glu Val Leu Arg Ile Leu Leu Asn Asp Met Lys
            180                 185                 190

Ala Glu Val Asp Ala Arg Asp Asn Met Gly Arg Asn Ala Leu Ile Arg
        195                 200                 205

Thr Leu Leu Asn Trp Asp Cys Glu Asn Val Glu Glu Ile Thr Ser Ile
210                 215                 220

Leu Ile Gln His Gly Ala Asp Val Asn Val Arg Gly Glu Arg Gly Lys
225                 230                 235                 240

Thr Pro Leu Ile Ala Ala Val Glu Arg Lys His Thr Gly Leu Val Gln
                245                 250                 255
```

```
Met Leu Leu Ser Arg Glu Gly Ile Asn Ile Asp Ala Arg Asp Asn Glu
            260                 265                 270

Gly Lys Thr Ala Leu Leu Ile Ala Val Asp Lys Gln Leu Lys Glu Ile
        275                 280                 285

Val Gln Leu Leu Leu Glu Lys Gly Ala Asp Lys Cys Asp Asp Leu Val
    290                 295                 300

Trp Ile Ala Arg Arg Asn His Asp Tyr His Leu Val Lys Leu Leu Leu
305                 310                 315                 320

Pro Tyr Val Ala Asn Pro Asp Thr Asp Pro Ala Gly Asp Trp Ser
                325                 330                 335

Pro His Ser Ser Arg Trp Gly Thr Ala Leu Lys Ser Leu His Ser Met
            340                 345                 350

Thr Arg Pro Met Ile Gly Lys Leu Lys Ile Phe Ile His Asp Asp Tyr
        355                 360                 365

Lys Ile Ala Gly Thr Ser Glu Gly Ala Val Tyr Leu Gly Ile Tyr Asp
    370                 375                 380

Asn Arg Glu Val Ala Val Lys Val Phe Arg Glu Asn Ser Pro Arg Gly
385                 390                 395                 400

Cys Lys Glu Val Ser Cys Leu Arg Asp Cys Gly Asp His Ser Asn Leu
                405                 410                 415

Val Ala Phe Tyr Gly Arg Glu Asp Asp Lys Gly Cys Leu Tyr Val Cys
            420                 425                 430

Val Ser Leu Cys Glu Trp Thr Leu Glu Glu Phe Leu Arg Leu Pro Arg
        435                 440                 445

Glu Glu Pro Val Glu Asn Gly Glu Asp Lys Phe Ala His Ser Ile Leu
    450                 455                 460

Leu Ser Ile Phe Glu Gly Val Gln Lys Leu His Leu His Gly Tyr Ser
465                 470                 475                 480

His Gln Asp Leu Gln Pro Gln Asn Ile Leu Ile Asp Ser Lys Lys Ala
                485                 490                 495

Val Arg Leu Ala Asp Phe Asp Gln Ser Ile Arg Trp Met Gly Glu Ser
            500                 505                 510

Gln Met Val Arg Arg Asp Leu Glu Asp Leu Gly Arg Leu Val Leu Tyr
        515                 520                 525

Val Val Met Lys Gly Glu Ile Pro Phe Glu Thr Leu Lys Thr Gln Asn
    530                 535                 540

Asp Glu Val Leu Leu Thr Met Ser Pro Asp Glu Thr Lys Asp Leu
545                 550                 555                 560

Ile His Cys Leu Phe Ser Pro Gly Glu Asn Val Lys Asn Cys Leu Val
                565                 570                 575

Asp Leu Leu Gly His Pro Phe Phe Trp Thr Trp Glu Asn Arg Tyr Arg
            580                 585                 590

Thr Leu Arg Asn Val Gly Asn Glu Ser Asp Ile Lys Val Arg Lys Cys
        595                 600                 605

Lys Ser Asp Leu Leu Arg Leu Leu Gln His Gln Thr Leu Glu Pro Pro
    610                 615                 620

Arg Ser Phe Asp Gln Trp Thr Ser Lys Ile Asp Lys Asn Val Met Asp
625                 630                 635                 640

Glu Met Asn His Phe Tyr Glu Lys Arg Lys Lys Asn Pro Tyr Gln Asp
                645                 650                 655

Thr Val Gly Asp Leu Leu Lys Phe Ile Arg Asn Ile Gly Glu His Ile
            660                 665                 670

Asn Glu Glu Lys Lys Arg Gly
            675
```

( 2 ) INFORMATION FOR SEQ ID NO:7:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asp Arg Arg Lys Pro Arg Gln Asn Asn Arg Arg Asp Arg Asn Glu Arg
 1               5                  10                  15
Arg Asp Thr Arg Ser Glu Arg Thr Glu Gly Ser Asp Asn Arg Glu Glu
             20                  25                  30
Asn Arg Arg Asn Arg Arg Gln Ala Gln Gln Gln Thr Ala Glu Thr Arg
         35                  40                  45
Glu Ser Arg Gln Gln Ala Glu Val Thr Glu Lys Ala Arg Thr Ala Asp
     50                  55                  60
Glu Gln Gln Ala Pro Arg Arg Glu Arg Ser Arg Arg Arg Asn Asp Asp
 65                  70                  75                  80
Lys Arg Gln Ala Gln Gln Glu Ala Lys Ala Leu Asn Val Glu Glu Gln
                 85                  90                  95
Ser Val Gln Glu Thr Gln Glu Glu Arg Val Arg Pro Val Gln Pro
                100                 105                 110
Arg Arg Lys Gln Arg Gln Leu Asn Gln Lys Val Arg Tyr Glu Gln Ser
             115                 120                 125
Val Ala Glu Glu Ala Val Val Ala Pro Val Val Glu Glu Thr Val Ala
         130                 135                 140
Ala Glu Pro Ile Val Gln Glu Ala Pro Ala Pro Arg Thr Glu Leu Val
145                  150                 155                 160
Lys Val Pro Leu Pro Val Val Ala Gln Thr Ala Pro Glu Gln Gln Glu
                 165                 170                 175
Glu Asn Asn Ala Asp Asn Arg Asp Asn Gly Gly Met Pro Ser
             180                 185                 190
```

( 2 ) INFORMATION FOR SEQ ID NO:8:

( i ) SEQUENCE CHARACTERISTICS:
        ( A ) LENGTH: 2562 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
CAGTTTCTGG  AGCAAATTCA  GTTTGCCTTC  CTGGATTTGT  AAATTGTAAT  GACCTCAAAA      60
CTTTAGCAGT  TCTTCCATCT  GACTCAGGTT  TGCTTCTCTG  GCGGTCTTCA  GAATCAACAT     120
CCACACTTCC  GTGATTATCT  GCGTGCATTT  TGGACAAAGC  TTCCAACCAG  GATACGGGAA     180
GAAGAAATGG  CTGGTGATCT  TTCAGCAGGT  TTCTTCATGG  AGGAACTTAA  TACATACCGT     240
CAGAAGCAGG  GAGTAGTACT  TAAATATCAA  GAACTGCCTA  ATTCAGGACC  TCCACATGAT     300
AGGAGGTTTA  CATTTCAAGT  TATAATAGAT  GGAAGAGAAT  TTCCAGAAGG  TGAAGGTAGA     360
TCAAAGAAGG  AAGCAAAAAA  TGCCGCAGCC  AAATTAGCTG  TTGAGATACT  TAATAAGGAA     420
AAGAAGGCAG  TTAGTCCTTT  ATTATTGACA  ACAACGAATT  CTTCAGAAGG  ATTATCCATG     480
GGGAATTACA  TAGGCCTTAT  CAATAGAATT  GCCCAGAAGA  AAAGACTAAC  TGTAAATTAT     540
```

-continued

```
GAACAGTGTG  CATCGGGGGT  GCATGGGCCA  GAAGGATTTC  ATTATAAATG  CAAAATGGGA   600
CAGAAAGAAT  ATAGTATTGG  TACAGGTTCT  ACTAAACAGG  AAGCAAAACA  ATTGGCCGCT   660
AAACTTGCAT  ATCTTCAGAT  ATTATCAGAA  GAAACCTCAG  TGAAATCTGA  CTACCTGTCC   720
TCTGGTTCTT  TTGCTACTAC  GTGTGAGTCC  CAAAGCAACT  CTTTAGTGAC  CAGCACACTC   780
GCTTCTGAAT  CATCATCTGA  AGGTGACTTC  TCAGCAGATA  CATCAGAGAT  AAATTCTAAC   840
AGTGACAGTT  TAAACAGTTC  TTCGTTGCTT  ATGAATGGTC  TCAGAAATAA  TCAAGGAAG    900
GCAAAAAGAT  CTTTGGCACC  CAGATTTGAC  CTTCCTGACA  TGAAAGAAAC  AAAGTATACT   960
GTGGACAAGA  GGTTTGGCAT  GGATTTTAAA  GAAATAGAAT  TAATTGGCTC  AGGTGGATTT  1020
GGCCAAGTTT  TCAAAGCAAA  ACACAGAATT  GACGGAAAGA  CTTACGTTAT  TAAACGTGTT  1080
AAATATAATA  ACGAGAAGGC  GGAGCGTGAA  GTAAAAGCAT  TGGCAAAACT  TGATCATGTA  1140
AATATTGTTC  ACTACAATGG  CTGTTGGGAT  GGATTTGATT  ATGATCCTGA  GACCAGTGAT  1200
GATTCTCTTG  AGAGCAGTGA  TTATGATCCT  GAGAACAGCA  AAAATAGTTC  AAGGTCAAAG  1260
ACTAAGTGCC  TTTTCATCCA  AATGGAATTC  TGTGATAAAG  GGACCTTGGA  ACAATGGATT  1320
GAAAAAGAA   GAGGCGAGAA  ACTAGACAAA  GTTTTGGCTT  TGGAACTCTT  TGAACAAATA  1380
ACAAAGGGG   TGGATTATAT  ACATTCAAAA  AAATTAATTC  ATAGAGATCT  TAAGCCAAGT  1440
AATATATTCT  TAGTAGATAC  AAAACAAGTA  AAGATTGGAG  ACTTTGGACT  TGTAACATCT  1500
CTGAAAAATG  ATGGAAAGCG  AACAAGGAGT  AGGGGAACTT  TGCGATACAT  GAGCCCAGAA  1560
CAGATTTCTT  CGCAAGACTA  TGGAAAGGAA  GTGGACCTCT  ACGCTTTGGG  GCTAATTCTT  1620
GCTGAACTTC  TTCATGTATG  TGACACTGCT  TTTGAAACAT  CAAAGTTTTT  CACAGACCTA  1680
CGGGATGGCA  TCATCTCAGA  TATATTTGAT  AAAAAAGAAA  AAACTCTTCT  ACAGAAATTA  1740
CTCTCAAAGA  AACCTGAGGA  TCGACCTAAC  ACATCTGAAA  TACTAAGGAC  CTTGACTGTG  1800
TGGAAGAAAA  GCCCAGAGAA  AAATGAACGA  CACACATGTT  AGAGCCCTTC  TGAAAAAGTA  1860
TCCTGCTTCT  GATATGCAGT  TTTCCTTAAA  TTATCTAAAA  TCTGCTAGGG  AATATCAATA  1920
GATATTTACC  TTTTATTTTA  ATGTTTCCTT  TAATTTTTTA  CTATTTTAC   TAATCTTTCT  1980
GCAGAAACAG  AAAGGTTTTC  TTCTTTTTGC  TTCAAAAACA  TTCTTACATT  TTACTTTTTC  2040
CTGGCTCATC  TCTTTATTTT  TTTTTTTTT   TTTTAAAGAC  AGAGTCTCGC  TCTGTTGCCC  2100
AGGCTGGAGT  GCAATGACAC  AGTCTTGGCT  CACTGCAACT  TCTGCCTCTT  GGGTTCAAGT  2160
GATTCTCCTG  CCTCAGCCTC  CTGAGTAGCT  GGATTACAGG  CATGTGCCAC  CCACCCAACT  2220
AATTTTTGTG  TTTTTAATAA  AGACAGGGTT  TCACCATGTT  GGCCAGGCTG  GTCTCAAACT  2280
CCTGACCTCA  AGTAATCCAC  CTGCCTCGGC  CTCCCAAAGT  GCTGGGATTA  CAGGGATGAG  2340
CCACCGCGCC  CAGCCTCATC  TCTTTGTTCT  AAAGATGGAA  AAACCACCCC  CAAATTTTCT  2400
TTTTATACTA  TTAATGAATC  AATCAATTCA  TATCTATTTA  TTAAATTTCT  ACCGCTTTTA  2460
GGCCAAAAAA  ATGTAAGATC  GTTCTCTGCC  TCACATAGCT  TACAAGCCAG  CTGGAGAAAT  2520
ATGGTACTCA  TTAAAAAAAA  AAAAAAAAG   TGATGTACAA  CC                      2562
```

( 2 ) INFORMATION FOR SEQ ID NO:9:

( i ) SEQUENCE CHARACTERISTICS:
        ( A ) LENGTH: 551 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

| Met | Ala | Gly | Asp | Leu | Ser | Ala | Gly | Phe | Phe | Met | Glu | Glu | Leu | Asn | Thr |
| 1 | | | | 5 | | | | | 10 | | | | | 15 | |

| Tyr | Arg | Gln | Lys | Gln | Gly | Val | Val | Leu | Lys | Tyr | Gln | Glu | Leu | Pro | Asn |
| | | | 20 | | | | | 25 | | | | | 30 | | |

| Ser | Gly | Pro | Pro | His | Asp | Arg | Arg | Phe | Thr | Phe | Gln | Val | Ile | Ile | Asp |
| | | 35 | | | | | 40 | | | | | 45 | | | |

| Gly | Arg | Glu | Phe | Pro | Glu | Gly | Glu | Gly | Arg | Ser | Lys | Lys | Glu | Ala | Lys |
| | 50 | | | | | 55 | | | | | 60 | | | | |

| Asn | Ala | Ala | Ala | Lys | Leu | Ala | Val | Glu | Ile | Leu | Asn | Lys | Glu | Lys | Lys |
| 65 | | | | | 70 | | | | | 75 | | | | | 80 |

| Ala | Val | Ser | Pro | Leu | Leu | Leu | Thr | Thr | Thr | Asn | Ser | Ser | Glu | Gly | Leu |
| | | | | 85 | | | | | 90 | | | | | 95 | |

| Ser | Met | Gly | Asn | Tyr | Ile | Gly | Leu | Ile | Asn | Arg | Ile | Ala | Gln | Lys | Lys |
| | | | 100 | | | | | 105 | | | | | 110 | | |

| Arg | Leu | Thr | Val | Asn | Tyr | Glu | Gln | Cys | Ala | Ser | Gly | Val | His | Gly | Pro |
| | | 115 | | | | | 120 | | | | | 125 | | | |

| Glu | Gly | Phe | His | Tyr | Lys | Cys | Lys | Met | Gly | Gln | Lys | Glu | Tyr | Ser | Ile |
| | 130 | | | | | 135 | | | | | 140 | | | | |

| Gly | Thr | Gly | Ser | Thr | Lys | Gln | Glu | Ala | Lys | Gln | Leu | Ala | Ala | Lys | Leu |
| 145 | | | | | 150 | | | | | 155 | | | | | 160 |

| Ala | Tyr | Leu | Gln | Ile | Leu | Ser | Glu | Glu | Thr | Ser | Val | Lys | Ser | Asp | Tyr |
| | | | | 165 | | | | | 170 | | | | | 175 | |

| Leu | Ser | Ser | Gly | Ser | Phe | Ala | Thr | Thr | Cys | Glu | Ser | Gln | Ser | Asn | Ser |
| | | | 180 | | | | | 185 | | | | | 190 | | |

| Leu | Val | Thr | Ser | Thr | Leu | Ala | Ser | Glu | Ser | Ser | Ser | Glu | Gly | Asp | Phe |
| | | 195 | | | | | 200 | | | | | 205 | | | |

| Ser | Ala | Asp | Thr | Ser | Glu | Ile | Asn | Ser | Asn | Ser | Asp | Ser | Leu | Asn | Ser |
| | 210 | | | | | 215 | | | | | 220 | | | | |

| Ser | Ser | Leu | Leu | Met | Asn | Gly | Leu | Arg | Asn | Asn | Gln | Arg | Lys | Ala | Lys |
| 225 | | | | | 230 | | | | | 235 | | | | | 240 |

| Arg | Ser | Leu | Ala | Pro | Arg | Phe | Asp | Leu | Pro | Asp | Met | Lys | Glu | Thr | Lys |
| | | | | 245 | | | | | 250 | | | | | 255 | |

| Tyr | Thr | Val | Asp | Lys | Arg | Phe | Gly | Met | Asp | Phe | Lys | Glu | Ile | Glu | Leu |
| | | | 260 | | | | | 265 | | | | | 270 | | |

| Ile | Gly | Ser | Gly | Gly | Phe | Gly | Gln | Val | Phe | Lys | Ala | Lys | His | Arg | Ile |
| | | 275 | | | | | 280 | | | | | 285 | | | |

| Asp | Gly | Lys | Thr | Tyr | Val | Ile | Lys | Arg | Val | Lys | Tyr | Asn | Asn | Glu | Lys |
| | 290 | | | | | 295 | | | | | 300 | | | | |

| Ala | Glu | Arg | Glu | Val | Lys | Ala | Leu | Ala | Lys | Leu | Asp | His | Val | Asn | Ile |
| 305 | | | | | 310 | | | | | 315 | | | | | 320 |

| Val | His | Tyr | Asn | Gly | Cys | Trp | Asp | Gly | Phe | Asp | Tyr | Asp | Pro | Glu | Thr |
| | | | | 325 | | | | | 330 | | | | | 335 | |

| Ser | Asp | Asp | Ser | Leu | Glu | Ser | Ser | Asp | Tyr | Asp | Pro | Glu | Asn | Ser | Lys |
| | | | 340 | | | | | 345 | | | | | 350 | | |

| Asn | Ser | Ser | Arg | Ser | Lys | Thr | Lys | Cys | Leu | Phe | Ile | Gln | Met | Glu | Phe |
| | | 355 | | | | | 360 | | | | | 365 | | | |

| Cys | Asp | Lys | Gly | Thr | Leu | Glu | Gln | Trp | Ile | Glu | Lys | Arg | Arg | Gly | Glu |
| | 370 | | | | | 375 | | | | | 380 | | | | |

| Lys | Leu | Asp | Lys | Val | Leu | Ala | Leu | Glu | Leu | Phe | Glu | Gln | Ile | Thr | Lys |
| 385 | | | | | 390 | | | | | 395 | | | | | 400 |

| Gly | Val | Asp | Tyr | Ile | His | Ser | Lys | Lys | Leu | Ile | His | Arg | Asp | Leu | Lys |
| | | | | 405 | | | | | 410 | | | | | 415 | |

|     | Pro | Ser | Asn | Ile<br>420 | Phe | Leu | Val | Asp | Thr<br>425 | Lys | Gln | Val | Lys | Ile<br>430 | Gly | Asp |
| --- | --- | --- | --- | --- | --- | --- | --- | --- | --- | --- | --- | --- | --- | --- | --- | --- |
|     | Phe | Gly | Leu<br>435 | Val | Thr | Ser | Leu | Lys<br>440 | Asn | Asp | Gly | Lys | Arg<br>445 | Thr | Arg | Ser |
|     | Lys | Gly<br>450 | Thr | Leu | Arg | Tyr | Met<br>455 | Ser | Pro | Glu | Gln | Ile<br>460 | Ser | Ser | Gln | Asp |
| Tyr<br>465 | Gly | Lys | Glu | Val | Asp<br>470 | Leu | Tyr | Ala | Leu | Gly<br>475 | Leu | Ile | Leu | Ala | Glu<br>480 |
| Leu | Leu | His | Val | Cys<br>485 | Asp | Thr | Ala | Phe | Glu<br>490 | Thr | Ser | Lys | Phe | Phe<br>495 | Thr |
| Asp | Leu | Arg | Asp<br>500 | Gly | Ile | Ile | Ser | Asp<br>505 | Ile | Phe | Asp | Lys | Lys<br>510 | Glu | Lys |
| Thr | Leu | Leu<br>515 | Gln | Lys | Leu | Leu | Ser<br>520 | Lys | Lys | Pro | Glu | Asp<br>525 | Arg | Pro | Asn |
| Thr | Ser<br>530 | Glu | Ile | Leu | Arg | Thr<br>535 | Leu | Thr | Val | Trp | Lys<br>540 | Lys | Ser | Pro | Glu |
| Lys<br>545 | Asn | Glu | Arg | His | Thr<br>550 | Cys |

(2) INFORMATION FOR SEQ ID NO:10:

(i) SEQUENCE CHARACTERISTICS:
        (A) LENGTH: 1650 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
AACTGAAACC  AACAGCAGTC  CAAGCTCAGT  CAGCAGAAGA  GATAAAAGCA  AACAGGTCTG    60
GGAGGCAGTT  CTGTTGCCAC  TCTCTCTCCT  GTCAATGATG  GATCTCAGAA  ATACCCCAGC   120
CAAATCTCTG  ACAAGTTCA   TTGAAGACTA  TCTCTTGCCA  GACACGTGTT  TCCGCATGCA   180
AATCGACCAT  GCCATTGACA  TCATCTGTGG  GTTCCTGAAG  GAAAGGTGCT  TCCGAGGTAG   240
CTCCTACCCT  GTGTGTGTGT  CCAAGGTGGT  AAAGGGTGGC  TCCTCAGGCA  AGGGCACCAC   300
CCTCAGAGGC  CGATCTGACG  CTGACCTGGT  TGTCTTCCTC  AGTCCTCTCA  GCACTTTTCA   360
GGATCAGTTA  AATCGCCGGG  GAGAGTTCAT  CCAGGAAATT  AGGAGACAGC  TGGAAGCCTG   420
TCAAAGAGAG  AGAGCACTTT  CCGTGAAGTT  TGAGGTCCAG  GCTCCACGCT  GGGGCAACCC   480
CCGTGCGCTC  AGCTTCGTAC  TGAGTTCGCT  CCAGCTCGGG  GAGGGGGTGG  AGTTCGATGT   540
GCTGCCTGCC  TTTGATGCCC  TGGGTCAGTT  GACTGGCAGC  TATAAACCTA  ACCCCCAAAT   600
CTATGTCAAG  CTCATCGAGG  AGTGCACCGA  CCTGCAGAAA  GAGGGCGAGT  TCTCCACCTG   660
CTTCACAGAA  CTACAGAGAG  ACTTCCTGAA  GCAGCGCCCC  ACCAAGCTCA  AGAGCCTCAT   720
CCGCCTAGTC  AAGCACTGGT  ACCAAAATTG  TAAGAAGAAG  CTTGGGAAGC  TGCCACCTCA   780
GTATGCCCTG  GAGCTCCTGA  CGGTCTATGC  TTGGGAGCGA  GGGAGCATGA  AAACACATTT   840
CAACACAGCC  AAGGATTTC   GGACGGTCTT  GGAATTAGTC  ATAAACTACC  AGCAACTCTG   900
CATCTACTGG  ACAAAGTATT  ATGACTTTAA  AAACCCCATT  ATTGAAAAGT  ACCTGAGAAG   960
GCAGCTCACG  AAACCCAGGC  CTGTGATCCT  GGACCCGGCG  GACCCTACAG  GAAACTTGGG  1020
TGGTGGAGAC  CCAAAGGGTT  GGAGGCAGCT  GGCACAAGAG  GCTGAGGCCT  GGCTGAATTA  1080
CCCATGCTTT  AAGAATTGGG  ATGGGTCCCC  AGTGAGCTCC  TGGATTCTGC  TGGCTGAAAG  1140
CAACAGTACA  GACGATGAGA  CCGACGATCC  CAGGACGTAT  CAGAAATATG  GTTACATTGG  1200
```

```
AACACATGAG  TACCCTCATT  TCTCTCATAG  ACCCAGCACG  CTCCAGGCAG  CATCCACCCC       1260

ACAGGCAGAA  GAGGACTGGA  CCTGCACCAT  CCTCTGAATG  CCAGTGCATC  TTGGGGGAAA       1320

GGGCTCCAGT  GTTATCTGGA  CCAGTTCCTT  CATTTTCAGG  TGGGACTCTT  GATCCAGAGA       1380

AGACAAAGCT  CCTCAGTGAG  CTGGTGTATA  ATCCAAGACA  GAACCCAAGT  CTCCTGACTC       1440

CTGGCCTTCT  ATGCCCTCTA  TCCTATCATA  GATAACATTC  TCCACAGCCT  CACTTCATTC       1500

CACCTATTCT  CTGAAAATAT  TCCCTGAGAG  AGAACAGAGA  GATTTAGATA  AGAGAATGAA       1560

ATTCCAGCCT  TGACTTTCTT  CTGTGCACCT  GATGGGAGGG  TAATGTCTAA  TGTATTATCA       1620

ATAACAATAA  AAATAAAGCA  AATACCAAAA                                           1650
```

( 2 ) INFORMATION FOR SEQ ID NO:11:

( i ) SEQUENCE CHARACTERISTICS:
        ( A ) LENGTH: 400 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met  Met  Asp  Leu  Arg  Asn  Thr  Pro  Ala  Lys  Ser  Leu  Asp  Lys  Phe  Ile
 1              5                        10                       15

Glu  Asp  Tyr  Leu  Leu  Pro  Asp  Thr  Cys  Phe  Arg  Met  Gln  Ile  Asp  His
               20                       25                       30

Ala  Ile  Asp  Ile  Ile  Cys  Gly  Phe  Leu  Lys  Glu  Arg  Cys  Phe  Arg  Gly
          35                       40                       45

Ser  Ser  Tyr  Pro  Val  Cys  Val  Ser  Lys  Val  Val  Lys  Gly  Gly  Ser  Ser
     50                       55                       60

Gly  Lys  Gly  Thr  Thr  Leu  Arg  Gly  Arg  Ser  Asp  Ala  Asp  Leu  Val  Val
65                       70                       75                       80

Phe  Leu  Ser  Pro  Leu  Thr  Thr  Phe  Gln  Asp  Gln  Leu  Asn  Arg  Arg  Gly
                    85                       90                       95

Glu  Phe  Thr  Gln  Glu  Ile  Arg  Arg  Gln  Leu  Glu  Ala  Cys  Gln  Arg  Glu
               100                      105                      110

Arg  Ala  Leu  Ser  Val  Lys  Phe  Glu  Val  Gln  Ala  Pro  Arg  Trp  Gly  Asn
          115                      120                      125

Pro  Arg  Ala  Leu  Ser  Phe  Val  Leu  Ser  Ser  Leu  Gln  Leu  Gly  Glu  Gly
     130                      135                      140

Val  Glu  Phe  Asp  Val  Leu  Pro  Ala  Phe  Asp  Ala  Leu  Gly  Gln  Leu  Thr
145                      150                      155                      160

Gly  Ser  Tyr  Lys  Pro  Asn  Pro  Gln  Ile  Tyr  Val  Lys  Leu  Ile  Glu  Glu
                    165                      170                      175

Cys  Thr  Asp  Leu  Gln  Lys  Glu  Gly  Glu  Phe  Ser  Thr  Cys  Gly  Thr  Glu
               180                      185                      190

Leu  Gln  Arg  Asp  Phe  Leu  Lys  Gln  Arg  Pro  Thr  Lys  Leu  Lys  Ser  Leu
          195                      200                      205

Ile  Arg  Leu  Val  Lys  His  Trp  Thr  Gln  Asn  Cys  Lys  Lys  Leu  Gly
     210                      215                      220

Lys  Leu  Pro  Pro  Gln  Tyr  Ala  Leu  Glu  Leu  Leu  Thr  Val  Tyr  Ala  Trp
225                      230                      235                      240

Glu  Arg  Gly  Ser  Met  Lys  Thr  His  Phe  Asn  Thr  Ala  Gln  Gly  Phe  Arg
                    245                      250                      255

Thr  Val  Leu  Glu  Leu  Val  Ile  Asn  Tyr  Gln  Gln  Leu  Cys  Ile  Tyr  Trp
               260                      265                      270
```

| | | | | | | | | | | | | | | |
|---|---|---|---|---|---|---|---|---|---|---|---|---|---|---|
| Ile | Lys | Tyr 275 | Tyr | Asp | Phe | Lys | Asn 280 | Pro | Ile | Ile | Glu | Lys 285 | Tyr | Leu | Arg |
| Arg | Gln 290 | Leu | Thr | Lys | Pro | Arg 295 | Pro | Val | Ile | Leu | Lys 300 | Pro | Ala | Asp | Pro |
| Thr 305 | Gly | Asn | Leu | Gly | Gly 310 | Gly | Asp | Pro | Lys | Gly 315 | Trp | Arg | Gln | Leu | Ala 320 |
| Gln | Glu | Ala | Glu | Ala 325 | Trp | Leu | Asn | Tyr | Pro 330 | Cys | Phe | Lys | Asn | Trp 335 | Asp |
| Gly | Ser | Pro | Val 340 | Ser | Ser | Trp | Ile | Leu 345 | Leu | Ala | Glu | Ser | Asn 350 | Ser | Thr |
| Asp | Asp | Glu 355 | Thr | Asp | Asp | Pro | Arg 360 | Thr | Tyr | Gln | Lys | Tyr 365 | Gly | Tyr | Ile |
| Gly | Thr 370 | His | Glu | Tyr | Pro | His 375 | Phe | Ser | His | Arg | Pro 380 | Ser | Thr | Leu | Gln |
| Ala 385 | Ala | Ser | Thr | Pro | Gln 390 | Ala | Glu | Glu | Asp | Trp 395 | Thr | Cys | Thr | Ile | Leu 400 |